United States Patent
Hirvelä et al.

(10) Patent No.: US 10,413,557 B2
(45) Date of Patent: Sep. 17, 2019

(54) PRODRUGS OF 17.BETA.-HSD1-INHIBITORS

(71) Applicant: FORENDO PHARMA LTD, Turku (FI)

(72) Inventors: Leena Hirvelä, Oulu (FI); Pasi Koskimies, Turku (FI); Risto Lammintausta, Turku (FI); Marjo Hakola, Kempele (FI); Maire Eloranta, Oulu (FI)

(73) Assignee: FORENDO PHARMA LTD., Turku (FI)

( * ) Notice: Subject to any disclaimer, the term of this patent is extended or adjusted under 35 U.S.C. 154(b) by 0 days.

(21) Appl. No.: 15/539,184

(22) PCT Filed: Dec. 22, 2015

(86) PCT No.: PCT/FI2015/050930
§ 371 (c)(1),
(2) Date: Jun. 23, 2017

(87) PCT Pub. No.: WO2016/102776
PCT Pub. Date: Jun. 30, 2016

(65) Prior Publication Data
US 2017/0354664 A1    Dec. 14, 2017

(30) Foreign Application Priority Data
Dec. 23, 2014 (FI) .................................... 20146150

(51) Int. Cl.
| C07J 41/00 | (2006.01) |
| A61K 31/58 | (2006.01) |
| C07J 43/00 | (2006.01) |
| C07J 51/00 | (2006.01) |
| A61K 31/566 | (2006.01) |
| A61K 31/5685 | (2006.01) |
| A61K 45/06 | (2006.01) |

(52) U.S. Cl.
CPC ............ *A61K 31/58* (2013.01); *A61K 31/566* (2013.01); *A61K 31/5685* (2013.01); *A61K 45/06* (2013.01); *C07J 41/00* (2013.01); *C07J 43/003* (2013.01); *C07J 51/00* (2013.01); *A61K 2300/00* (2013.01)

(58) Field of Classification Search
None
See application file for complete search history.

(56) References Cited

U.S. PATENT DOCUMENTS

| 2003/0170292 A1 | 9/2003 | Yong et al. |
| 2005/0192263 A1 | 9/2005 | Messinger et al. |
| 2006/0281710 A1 | 12/2006 | Messinger et al. |
| 2017/0081356 A1 | 3/2017 | Hirvelä et al. |
| 2017/0114090 A1 | 4/2017 | Eloranta et al. |
| 2018/0265541 A1 | 9/2018 | Hirvelä et al. |

FOREIGN PATENT DOCUMENTS

| CN | 1878786 A | 12/2006 |
| WO | WO 1999/046279 | 9/1999 |
| WO | WO 2000/007996 | 2/2000 |
| WO | WO 2001/042181 | 6/2001 |
| WO | WO 2003/022835 | 3/2003 |
| WO | WO 2003/033487 | 4/2003 |
| WO | WO 2004/046111 | 6/2004 |
| WO | WO 2004/060488 | 7/2004 |
| WO | WO 2004/085345 | 10/2004 |
| WO | WO 2004/085457 | 10/2004 |

(Continued)

OTHER PUBLICATIONS

Allan et al., "Modification of Estrone at the 6, 16, and 17 Positions: Novel Potent Inhibitors of 17β-Hydroxysteroid Dehydrogenase Type 1", *J. Med. Chem.*, vol. 49, No. 4., pp. 1325-1345, Jan. 2006.
Messinger et al., "Estrone C15 derivatives—A new class of 17β-hydroxysteroid dehydrogenase type 1 inhibitors", *Molecular and Cellular Endocrinology*, vol. 301, pp. 216-224, (2009).
Poirier, Donald, "Inhibitors of 17β-Hydroxysteroid Dehydrogenases", *Current Medicinal Chemistry*, vol. 10, No. 6; pp. 453-477; (2003).
Poirier, Donald, "17β-Hydroxysteroid dehydrogenase inhibitors: a patent review", *Expert Opin. Ther. Patents*, 20(9), pp. 1123-1145; (2010).
Puranen et al., "Site-directed mutagenesis of the putative active site of human 17β-hydroxysteroid dehydrogenase type 1", *Biochem. J.*, 304; pp. 289-293; (1994).
Written Opinion of International Searching Authority for International Application No. PCT/FI2015/050930 (dated Mar. 29, 2016).
Search Report for Finnish Patent Application No. 20146150, dated Aug. 18, 2015, 3 pages.
Chinese Office Action dated Oct. 24, 2018 with translation.

*Primary Examiner* — Samantha L Shterengarts
(74) *Attorney, Agent, or Firm* — Brinks Gilson & Lione

(57) ABSTRACT

The invention relates to compounds of formula (I) and pharmaceutically acceptable salts thereof wherein R1 to R4 are as defined in the claims. The invention further relates to their use as inhibitors of 17β-HSD1 and in treatment or prevention of steroid hormone dependent diseases or disorders, such as steroid hormone dependent diseases or disorders requiring the inhibition of the 17β-HSD1 enzyme and/or requiring the lowering of the endogenous estradiol concentration. The present invention also relates to the preparation of the aforementioned compounds and to pharmaceutical compositions comprising as an active ingredient(s) one or more of the aforementioned compounds or pharmaceutically acceptable salts thereof.

12 Claims, No Drawings

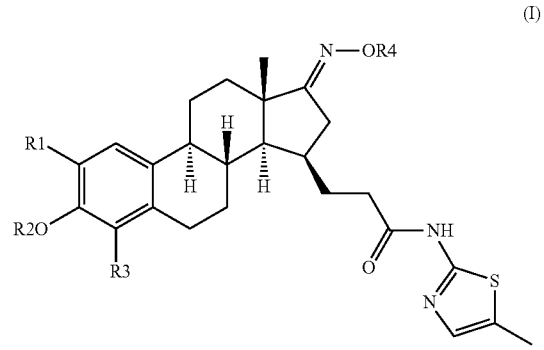

(I)

(56) References Cited

FOREIGN PATENT DOCUMENTS

| WO | WO 2004/110459 | 12/2004 |
|---|---|---|
| WO | WO 2005/032527 | 4/2005 |
| WO | WO 2005/047303 | 5/2005 |
| WO | WO 2005/084295 | 9/2005 |
| WO | WO 2006/003012 | 1/2006 |
| WO | WO 2006/003013 | 1/2006 |
| WO | WO 2006/027347 | 3/2006 |
| WO | WO 2006/125800 | 11/2006 |
| WO | WO 2008/034796 | 3/2008 |
| WO | WO 2008/065100 | 6/2008 |
| WO | WO2014/207309 A1 | 12/2014 |
| WO | WO 2014/207310 | 12/2014 |
| WO | WO2014/207310 A1 | 12/2014 |
| WO | WO2014/207311 A1 | 12/2014 |
| WO | WO2016/102775 A1 | 6/2016 |

PRODRUGS OF 17.BETA.-HSD1-INHIBITORS

FIELD OF THE INVENTION

The present invention relates to novel compounds, to their pharmaceutically acceptable salts, and to their use in therapy for inhibiting 17β-hydroxysteroid dehydrogenases. The invention further relates to pharmaceutical compositions comprising these compounds.

BACKGROUND OF THE INVENTION

17β-hydroxysteroid dehydrogenases (17β-HSDs), also known as 17-ketosteroid reductases (17-KSR) are NAD(H)- and/or NAPD(H)-dependent alcohol oxidoreductase enzymes which catalyse the last and key step in formation of all estrogens and androgens. More specifically 17β-HSDs catalyse the dehydrogenation (oxidation) of 17-hydroxysteroids into corresponding 17-ketosteroids or hydrogenation (reduction) of inactive 17-ketosteroids into corresponding active 17-hydroxysteroids.

As both estrogens and androgens have the highest affinity for their receptors in the 17β-hydroxy form, the 17β-HSD/KSRs regulate the biological activity of the sex hormones. At present, 15 human members of 17β-HSDs have been described (type 1-15). Different types of 17β-HSD/KSRs differ in their substrate and cofactor specificities. The 17KSR activities convert low-activity precursors to more potent forms while 17β-HSD activities decrease the potency of estrogens and androgens and consequently may protect tissues from excessive hormone action.

Each type of 17β-HSD has a selective substrate affinity and a distinctive, although in some cases overlapping, tissue distribution.

Type 1 17β-hydroxysteroid dehydrogenase (17β-HSD1) is most abundantly expressed in the ovarian granulosa cells of the developing follicles in ovaries and in human placenta, both being estrogen biosynthetic tissues. In addition, 17β-HSD1 is expressed in estrogen target tissues, including breast, endometrium and bone. The human 17β-HSD1 is specific to estrogenic substrates and in vivo catalyzes the reduction of estrone to estradiol.

Type 2 17β-hydroxysteroid dehydrogenase (17β-HSD2) on the other hand converts estradiol, testosterone and 5a-dihydrotestosterone to their less active forms estrone, androstenedione and 5a-androstanedione, respectively. Due to its wide and abundant expression in number of various estrogen and androgen target tissues, such as uterus, placenta, liver and the gastrointestinal and urinary tracts, it has been suggested that type 2 enzyme protects tissues from excessive steroid actions.

Estradiol (E2) is about 10 times as potent as estrone (E1) and about 80 times as potent as estratriol (E3) in its estrogenic effect. In contrast to certain other estrogens, estradiol binds well to both estrogen receptors ERα and ERβ, and thus regulates the expression of a variety of genes.

Although both 17β-HSD1 and 17β-HSD2 are present in healthy premenopausal humans, increased ratio of 17β-HSD1 to 17-HSD2 in the tumors of postmenopausal patients with hormone-dependent breast cancer has been shown in several studies. 17HSD1 gene amplification and loss of heterozygosity of 17HSD2 allele are potential mechanisms involved to increased reductive estrogen synthesis pathway in breast tumors. Increased ratio of type 1 enzyme to type 2 enzyme results in an increased level of estradiol that then promotes the proliferation of the cancerous tissue via the estrogen receptors (ER). High levels of estrogen thus support certain cancers such as breast cancer and cancer of the uterine lining i.e. endometrial cancer and uterine cancer.

Similarly it has been suggested that 17β-HSD2 is down-regulated in endometriosis while both aromatase and 17β-HSD1 are expressed or upregulated in comparison with normal endometrium. This again results in the presence of high concentration of estradiol (E2) which drives the proliferation of the tissue. Similar mechanism has been elucidated in uterine leiomyoma (uterine fibroids) and endometrial hyperplasia.

Reduction of the endogenous estradiol concentration in affected tissues will result in reduced or impaired proliferation of 17β-estradiol cells in said tissues and may thus be utilized in prevention and treatment of malign and benign estradiol dependent pathologies. Due to the proposed involvement of 17β-estradiol in a number of malign and benign pathologies, inhibitors of 17β-hydroxysteroid dehydrogenases, that can be used to impair endogenous production of estradiol from estrone, can have therapeutic value in the prevention or the treatment of such disorders or diseases are in great demand.

Some small-molecule inhibitors of 17β-HSD1 enzyme have been identified and reviewed in Poirier D. (2003) Curr Med Chem 10: 453-77 and Poirier D. (2010) Expert Opin. Ther. Patents 20(9): 1123-1145. Further, small molecule inhibitors of 17β-HSD's have been disclosed in WO 2001/42181, WO 2003/022835, WO 2003/033487, WO2004/046111, WO2004/060488, WO 2004/110459, WO 2005/032527, and WO 2005/084295.

WO2004/085457 discloses steroidal compounds capable of inhibiting 17β-hydroxysteroid dehydrogenase. WO2006/003012 discloses 2-substituted D-homo-estriene derivatives suitable for the treatment of estrogen-dependent diseases that can be influenced by the inhibition of the 17β-hydroxysteroid dehydrogenase type 1. Similarly WO2006/003013 presents 2-substituted estratrienones usable for preventing and treating estrogen-dependent diseases influenced by inhibiting 17β-hydroxysteroid dehydrogenase type 1.

15-substituted estradiol analogues acting as locally active estrogens are presented in WO2004/085345. WO2006/027347 discloses 15b-substituted estradiol derivatives having selective estrogenic activity for the treatment or prevention of estrogen receptor-related diseases and physiological conditions. Further, WO2005/047303 discloses 3, 15 substituted estrone derivatives capable of inhibiting the 17β-hydroxysteroid dehydrogenase type 1.

International application WO2008/034796 relates to estratrien triazoles suitable for use in treatment and prevention of steroid hormone dependent diseases or disorders requiring the inhibition of a 17β-hydroxysteroid dehydrogenases such as 17β-HSD type 1, type 2 or type 3 enzyme. Inhibitors of 17β-HSD type 3 enzyme have been disclosed in WO99/46279.

BRIEF DESCRIPTION OF THE INVENTION

An object of the present invention is to provide novel compounds that have improved therapeutic properties useful in treating disorders and diseases associated with increased level of estradiol and/or treatable by inhibition of 17β-HSD1 enzyme. It is further an object of the present invention to provide compounds that show little or no inhibitory effect on 17β-HSD2 enzyme.

The compounds of the invention may act as prodrugs. By virtue of the nature of the masking moieties, when included in the compounds of the present invention, masked biologically active entities can delivered to the patients in need thereof. Moreover, the compounds of the invention will advantageously exhibit better solubility and resultantly better bioavailability in vivo than the corresponding naked biologically active entity.

The present invention accordingly provides novel compounds of formula (I)

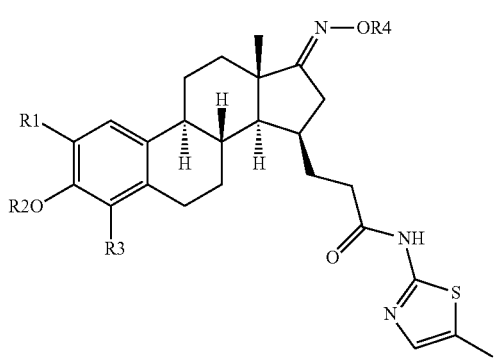

wherein R1, R2, R3 and R4 are as defined in the claims.

The invention also relates to pharmaceutical compositions comprising an effective amount of one or more compound(s) of formula (I).

Further the invention relates to a compound of formula (I) or a pharmaceutically acceptable salt thereof for use as a medicament.

The invention also relates to a compound of formula (I) or a pharmaceutically acceptable salt thereof for use in the treatment of estradiol dependent malign or benign diseases and disorders.

Finally the invention provides a method for the preparation of compounds of formula (I).

DETAILED DESCRIPTION OF THE INVENTION

Compounds of the invention contain steroidal core structure having a defined stereochemistry that is the natural configuration of estrogens.

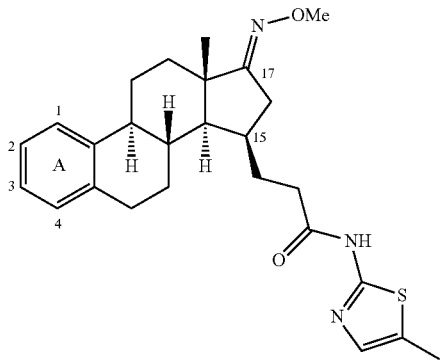

Compounds of the invention bear a methyl thiazolyl side chain at C15 in β-configuration which, together with the specific substitution pattern of the A ring, provides the inventive properties of the compounds of the present invention. Also, the C-17 carbonyl group of the native estrone core is masked as a C-17 ketimine. This particular C-17 moiety enhances the metabolic and/or inhibitory properties of the compounds of the present invention. And in particular the C-3 OH moiety of the active entity is masked with a non-toxic protecting group to advantageously alter the solubility of the compounds.

We have earlier shown that compounds disclosed in PCT/FI2014/050518, the entire contents and disclosures of which are hereby incorporated by reference, are useful in treating disorders and diseases associated with increased level of estradiol and/or treatable by inhibition of 17β-HSD1 enzyme. These compounds show little or no inhibitory effect on 17β-HSD2 enzyme. Particular examples of such compound disclosed in PCT/FI2014/050518 are compounds of formula (VIV)

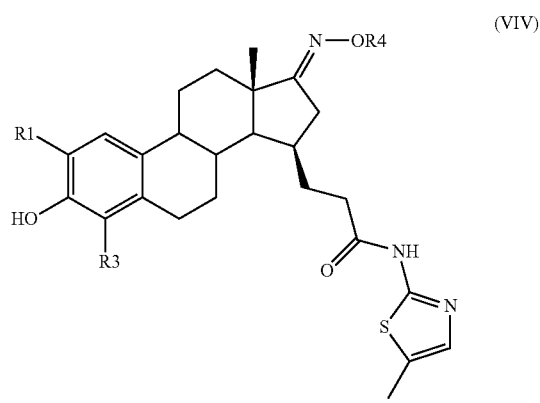

wherein

R1 and R3 are each independently selected from the group consisting of H, halogen, $C_{1-3}$-haloalkyl, $C_{1-3}$-perhaloalkyl, CN, $NO_2$, $N(R')_2$, $(CH_2)_nN(R')_2$, OR', $(CH_2)_nOR'$; and R4 is H or $C_{1-3}$-alkyl.

However, the compounds disclosed in PCT/FI2014/050518 are either poorly soluble or insoluble in water thus limiting routes of administration and/or drug formulation. For example for oral administration the compounds disclosed in PCT/FI2014/050518 would have to be administrated with surfactants which may cause serious side effects to some patients. Thus development of a water-soluble compound is highly desired to improve bioavailability.

The object of the present invention is to provide compounds including a therapeutically active entity of formula (VIV). In an aspect of the present invention the compounds of the invention are water-soluble prodrug compounds. The particular water-soluble compounds may be administered orally without undesirable dissolving aids.

Compounds of the present invention convert to the substantially water-insoluble selective 17β-HSD1 inhibitory compounds following administration to a subject. The compounds of the present invention are hydrolyzed by an esterase in vivo to deliver the active ingredient. The compounds may also have biological activity as such. Accordingly the compounds of the invention may be active entities as such as well as deliver a biologically active parent molecule. The compounds of the present invention, having the structural formula (I) below, itself may show weak or strong in vitro inhibitory activity against 17β-HSD1, while the masked active entity (VIV) has a strong inhibitory activity against 17β-HSD1 but shows little or no inhibitory effect on 17β-HSD2.

The term "alkyl" as used herein and hereafter as such or as part of haloalkyl, perhaloalkyl or alkoxy group is an aliphatic linear, branched or cyclic, especially linear or branched, hydrocarbon group having the indicated number of carbon atoms, for example $C_{1-6}$-alkyl has 1 to 6 carbon atoms in the alkyl moiety and thus, for example, $C_{1-3}$-alkyl includes methyl, ethyl, n-propyl, isopropyl, and $C_{1-6}$-alkyl additionally includes branched and straight chain n-butyl, sec-butyl, iso-butyl, tert-butyl, pentyl and hexyl.

The term "haloalkyl" as used herein and hereafter refers to any of the above alkyl groups where one or more hydrogen atoms are replaced by halogen(s): in particular I, Br, F or Cl. Examples of haloalkyl groups include without limitation chloromethyl, fluoromethyl and —$CH_2CF_3$. The term "perhaloalkyl" is understood to refer to an alkyl group, in which all the hydrogen atoms are replaced by halogen atoms. Preferred examples include trifluoromethyl (—$CF_3$) and trichloromethyl (—$CCl_3$).

The term "halogen" as used herein and hereafter by itself or as part of other groups refers to the Group VIIa elements and includes F, Cl, Br and I.

The term "$C_{3-6}$-cycloalkyl" as used herein and hereafter refers to cycloalkyl groups having 3 to 6 carbon atoms and thus includes cyclopropyl, cyclobutyl, cyclopentyl, and cyclohexyl.

The term "alkenyl" as used herein and hereafter is an unsaturated linear or branched hydrocarbon group having at least one olefinic double bond between any two carbon atoms and having the indicated number of carbon atoms, for example $C_{2-6}$-alkenyl has 2 to 6 carbon atoms in the alkenyl moiety, such as ethenyl, propenyl, butenyl, pentenyl, and hexenyl. Examples of preferred alkenyls groups include, but are not limited to, linear alkenyl groups having a terminal double bond such as vinyl and allyl groups.

The term "optionally substituted" as used herein and hereafter in context of a phenyl group denotes phenyl that is either un-substituted or substituted independently with one or more, in particular 1, 2, or 3, substituent(s) attached at any available atom to produce a stable compound, e.g. phenyl may be substituted once with a denoted substituent attached to o-, p- or m-position of the phenyl ring. In general "substituted" refers to a substituent group as defined herein in which one or more bonds to a hydrogen atom contained therein are replaced by a bond to a non-hydrogen atom unless otherwise denoted. The substituent groups are each independently selected from the group consisting of halogen; $C_{1-4}$-alkyl, in particular methyl; OH; $C_{1-4}$-alkoxy, in particular methoxy; CN; $NO_2$; and acetoxy. Preferably said phenyl is optionally substituted with acetoxy.

"Optional" or "optionally" denotes that the subsequently described event or circumstance may but need not occur, and that the description includes instances where the event or circumstance occurs and instances in which it does not. "Comprises" or "comprising" denotes that the subsequently described set may but need not include other elements.

The expression "pharmaceutically acceptable" represents being useful in the preparation a pharmaceutical composition that is generally safe, non-toxic, and neither biologically nor otherwise undesirable, and includes being useful for both veterinary use as well as human pharmaceutical use.

The term "pharmaceutically acceptable salts" refers to salts which are known to be non-toxic and are commonly used in the pharmaceutical literature. Typically these are acid addition salts or base addition salts of the referred compounds.

The expression "acid addition salt" includes any non-toxic organic and inorganic acid addition salts that compounds of formula (I) can form. Illustrative inorganic acids, which form suitable salts, include, but are not limited to, hydrogen chloride, hydrogen bromide, sulphuric and phosphoric acids. Illustrative organic acids, which form suitable salts, include, but are not limited to, acetic acid, lactic acid, malonic acid, succinic acid, glutaric acid, fumaric acid, malic acid, tartaric acid, citric acid, ascorbic acid, maleic acid, benzoic acid, phenylacetic acid, cinnamic acid, methane sulfonic acid, salicylic acid, and the like. The term "acid addition salt" as used herein also comprises solvates which the compounds and salts thereof are able to form, such as, for example, hydrates, alcoholates, and the like. These salts also include salts useful for the chiral resolution of racemates.

The expression "base addition salt" includes any non-toxic base addition salts that the compound of formula (I) can form. Suitable base salts include, but are not limited to, those derived from inorganic bases such as aluminum, ammonium, calcium, copper, iron, lithium, magnesium, manganese, potassium, sodium, and zinc salts, in particular sodium and ammonium salts. Further examples of organic base addition salt include salts of trialkylamines, such as triethyl amine and trimethyl amine, and choline salts.

The objects of the invention may be achieved by novel compounds having formula (I)

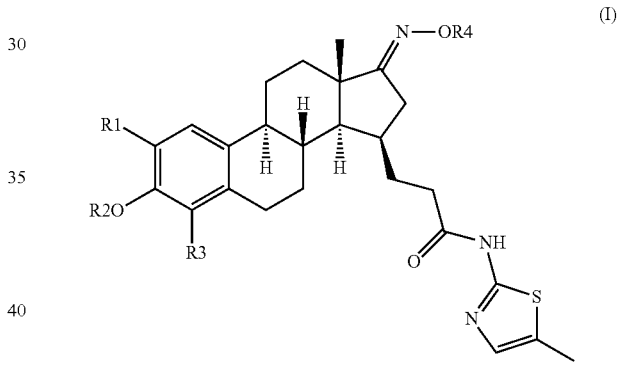

wherein

R1 and R3 are each independently selected from the group consisting of H, halogen, $C_{1-3}$-haloalkyl, $C_{1-3}$-perhaloalkyl, CN, $NO_2$, $N(R')_2$, $(CH_2)_nN(R')_2$, OR', $(CH_2)_nOR'$;

R2 is selected from the group consisting of $SO_2OH$, $SO_2R'''$, $SO_2N(R')_2$, $(CH_2O)_mPO(OR')_2$, $COOR'''$, $C(O)N(R')_2$, $C(O)(CH_2)_nN(R')_2$, $C(O)CH_2NR'C(O)R'$, $C(O)CH_2NR'C(O)OR''$ and $C(O)R'''$;

R4 is H or $C_{1-3}$-alkyl;

whereby

R' is H or $C_{1-6}$-alkyl, $C_{1-3}$-haloalkyl, or $C_{1-3}$-perhaloalkyl, or when part of any $N(R')_2$ both R's together with the nitrogen they are attached to may form a 5 to 6 membered aliphatic or aromatic heterocyclic ring comprising 1 or 2 heteroatoms each independently selected from N and O or a charged $N(R')_3$+ group wherein R' is as defined above;

R'' is $C_{1-6}$-alkyl, $C_{1-3}$-haloalkyl, $C_{1-3}$-perhaloalkyl, or an optionally substituted phenyl;

R''' is $C_{1-6}$-alkyl; $C_{2-6}$-alkenyl; —$(CH_2)_n$—$C_{3-6}$-cycloalkyl; a 5 to 6 membered aliphatic or aromatic heterocyclic ring comprising 1 or 2 heteroatoms each independently selected from N and O, optionally substituted at any N atom by C(O)R' wherein R' is as defined above; or an optionally substituted phenyl;

m is 0 or 1; and n is 1 or 2 provided that when R1 is H, R2 is not C(O)Me, C(O) CH$_2$NMe$_2$, S(O)$_2$NH$_2$, S(O)$_2$NMe$_2$, or S(O)$_2$Me.

In further aspect of the invention R4 is methyl or ethyl, in particular methyl. Compounds of formula (I) wherein R4 is methyl or ethyl, in particular methyl, exhibit show little or no inhibitory effect on 17β-HSD2 enzyme.

In another aspect of the invention R1 and R3 are each independently selected from H, halogen, C$_{1-3}$-haloalkyl, C$_{1-3}$-perhaloalkyl, CN, and NO$_2$, preferably from H, halogen, NO$_2$, and CN. In a particular aspect of the invention R1 and R3 are each independently H or halogen; in particular R1 and R3 are both are H.

In still further aspect of the present invention is provided compound of formula (I) and (Ia), wherein R2 is selected from the group consisting of (CH$_2$O)$_m$PO(OR')$_2$, C(O) (CH$_2$)$_n$ N(R')$_2$, C(O)CH$_2$NR'C(O)R', and C(O)CH$_2$NR'C(O) OR". Preferred are compounds of formula (I) as claimed in any one of claims 1 to 5, wherein R2 is C(O)(CH$_2$)$_n$N(R')$_2$. These compounds exhibit aqueous solubility.

Further preferred are compounds of formula (I), wherein R2 is (CH$_2$O)$_m$PO(OR')$_2$, wherein R' is H, C$_{1-6}$-alkyl, C$_{1-3}$-haloalkyl, or C$_{1-3}$-perhaloalkyl, and m is 0 or 1. These compounds show particularly good aqueous solubility as will be demonstrated below.

In an aspect of the present invention relates to a compound of formula (I) selected from the group consisting of:

Compound 1 Phosphoric acid mono-{(13S,15R)-17-[(E)-methoxyimino]-13-methyl-15-[2-(5-methylthiazol-2-ylcarbamoyl)ethyl-7,8,9,11,12,13,14,15,16,17-decahydro-6H-cyclopenta[a]phenanthren-3-yl} ester;

Compound 2 tert-Butoxycarbonylamino-acetic acid (13S,15R)-13-methyl-17[(E)-methoxyimino]-15-[2-(5-methyl-thiazol-2-ylcarbamoyl)-ethyl]-7,8,9,11,12,13,14,15,16,17-decahydro-6H-cyclopenta[a]phenanthren-3-yl ester;

Compound 3 Aminoacetic acid (13S,15R)-13-methyl-17[(E)-methoxyimino]-15-[2-(5-methyl-thiazol-2-ylcarbamoyl)-ethyl]-7,8,9,11,12,13,14,15,16,17-decahydro-6H-cyclopenta[a]phenanthren-3-yl ester;

Compound 4 Tert-Butoxycarbonyl-methylamino-acetic acid (13S,15R)-13-methyl-17[(E)-methoxyimino]-15-[2-(5-methyl-thiazol-2-ylcarbamoyl)-ethyl]-7,8,9,11,12,13,14,15,16,17-decahydro-6H-cyclopenta[a]phenanthren-3-yl ester;

Compound 5 Methylamino-acetic acid (13S,15R)-13-methyl-17[(E)-methoxyimino]-15-[2-(5-methyl-thiazol-2-ylcarbamoyl)-ethyl]-7,8,9,11,12,13,14,15,16,17-decahydro-6H-cyclopenta[a]phenanthren-3-yl ester;

Compound 6 Morpholin-4-yl-acetic acid (13S,15R)-13-methyl-17[(E)-methoxyimino]-15-[2-(5-methyl-thiazol-2-ylcarbamoyl)-ethyl]-7,8,9,11,12,13,14,15,16,17-decahydro-6H-cyclopenta[a]phenanthren-3-yl ester;

Compound 7 1-(tert-butyl)2-(13S,15R,E)-17-(methoxyimino)-13-methyl-15-(3-((5-methylthiazol-2-yl)amino)-3-oxopropyl)-7,8,9,11,12,13,14,15,16,17-decahydro-6H-cyclopenta[a]phenanthren-3-yl)-pyrrolidine-1,2-dicarboxylate;

Compound 8 (13S,15R,E)-17-(methoxyimino)-13-methyl-15-(3-((5-methylthiazol-2-yl)amino)-3-oxopropyl)-7,8,9,11,12,13,14,15,16,17-decahydro-6H-cyclopenta[a]phenanthren-3-yl prolinate;

Compound 9 di-tert-butyl((((13S,15R,E)-17-(methoxyimino)-13-methyl-15-(3-((5-methylthiazol-2-yl)amino)-3-oxopropyl)-7,8,9,11,12,13,14,15,16,17-decahydro-6H-cyclopenta[a]phenanthren-3-yl)oxy)-methyl) phosphate;

Compound 10 (((13S,15R,E)-17-(methoxyimino)-13-methyl-15-(3-((5-methylthiazol-2-yl)amino)-3-oxopropyl)-7,8,9,11,12,13,14,15,16,17-decahydro-6H-cyclopenta[a]phenanthren-3-yl)oxy)methyl dihydrogen phosphate;

Compound 11 (13S,15R)-2,4-dibromo-13-methyl-15-(3-((5-methyl-thiazol-2-yl)amino)-3-oxopropyl)-17-oxo-7,8,9,11,12,13,14,15,16,17-decahydro-6H-cyclopenta[a]phenanthren-3-yl acetate;

Compound 12 (13S,15R,E)-2,4-dibromo-17-(hydroxyimino)-13-methyl-15-(3-((5-methylthiazol-2-yl)amino)-3-oxopropyl)-7,8,9,11,12,13,14,15,16,17-decahydro-6H-cyclopenta[a]phenanthren-3-yl acetate;

Compound 13 (13S,15R,E)-2,4-dibromo-17-(methoxyimino)-13-methyl-15-(3-((5-methylthiazol-2-yl)amino)-3-oxopropyl)-7,8,9,11,12,13,14,15,16,17-decahydro-6H-cyclopenta[a]phenanthren-3-yl acetate;

Compound 14 (13S,15R,E)-2,4-dibromo-17-(methoxyimino)-13-methyl-15-(3-((5-methylthiazol-2-yl)amino)-3-oxopropyl)-7,8,9,11,12,13,14,15,16,17-decahydro-6H-cyclopenta[a]phenanthren-3-yl dihydrogen phosphate;

Compound 15 (13S,15R,Z)-2,4-dibromo-17-(methoxyimino)-13-methyl-15-(3-((5-methylthiazol-2-yl)amino)-3-oxopropyl)-7,8,9,11,12,13,14,15,16,17-decahydro-6H-cyclopenta[a]phenanthren-3-yl dimethylglycinate;

Compound 16 (13S,15R,E)-2-iodo-17-(methoxyimino)-13-methyl-15-(3-((5-methylthiazol-2-yl)amino)-3-oxopropyl)-7,8,9,11,12,13,14,15,16,17-decahydro-6H-cyclopenta[a]phenanthren-3-yl dimethylglycinate;

Compound 17 (13S,15R,E)-2-iodo-17-(methoxyimino)-13-methyl-15-(3-((5-methylthiazol-2-yl)amino)-3-oxopropyl)-7,8,9,11,12,13,14,15,16,17-decahydro-6H-cyclopenta[a]phenanthren-3-yl dihydrogen phosphate;

Compound 18 (13S,15R,E)-17-(methoxyimino)-13-methyl-15-(3-((5-methylthiazol-2-yl)amino)-3-oxopropyl)-4-nitro-7,8,9,11,12,13,14,15,16,17-decahydro-6H-cyclopenta[a]phenanthren-3-yl dihydrogen phosphate;

Compound 19 (13S,15R,E)-17-(hydroxyimino)-13-methyl-15-(3-((5-methylthiazol-2-yl)amino)-3-oxopropyl)-4-nitro-7,8,9,11,12,13,14,15,16,17-decahydro-6H-cyclopenta[a]phenanthren-3-yl dihydrogen phosphate;

Compound 20 (13S,15R,E)-4-bromo-17-(hydroxyimino)-13-methyl-15-(3-((5-methylthiazol-2-yl)amino)-3-oxopropyl)-7,8,9,11,12,13,14,15,16,17-decahydro-6H-cyclopenta[a]phenanthren-3-yl dihydrogen phosphate;

Compound 21 (13S,15R,E)-2,4-diiodo-17-(methoxyimino)-13-methyl-15-(3-((5-methylthiazol-2-yl)amino)-3-oxopropyl)-7,8,9,11,12,13,14,15,16,17-decahydro-6H-cyclopenta[a]phenanthren-3-yl dimethylglycinate;

Compound 22 (13S,15R,E)-2,4-dibromo-17-(hydroxyimino)-13-methyl-15-(3-((5-methylthiazol-2-yl)amino)-3-oxopropyl)-7,8,9,11,12,13,14,15,16,17-decahydro-6H-cyclopenta[a]phenanthren-3-yl dihydrogen phosphate;

Compound 23 (13S,15R,E)-2,4-diiodo-17-(methoxyimino)-13-methyl-15-(3-((5-methylthiazol-2-yl)amino)-3-oxopropyl)-7,8,9,11,12,13,14,15,16,17-decahydro-6H-cyclopenta[a]phenanthren-3-yl dihydrogen phosphate;

and pharmaceutically acceptable salts thereof.

In a preferred aspect of the present invention relates to a compound of formula (I) selected from the group consisting of:

Compound 1 Phosphoric acid mono-{(13S,15R)-17-[(E)-methoxyimino]-13-methyl-15-[2-(5-methylthiazol-2-ylcarbamoyl)ethyl-7,8,9,11,12,13,14,15,16,17-decahydro-6H-cyclopenta[a]phenanthren-3-yl} ester;

Compound 2 tert-Butoxycarbonylamino-acetic acid (13S,15R)-13-methyl-17[(E)-methoxyimino]-15-[2-(5-methyl-thiazol-2-ylcarbamoyl)-ethyl]-7,8,9,11,12,13,14,15,16,17-decahydro-6H-cyclopenta[a]phenanthren-3-yl ester;

Compound 3 Aminoacetic acid (13S,15R)-13-methyl-17[(E)-methoxyimino]-15-[2-(5-methyl-thiazol-2-ylcarbamoyl)-ethyl]-7,8,9,11,12,13,14,15,16,17-decahydro-6H-cyclopenta[a]phenanthren-3-yl ester;

Compound 4 Tert-Butoxycarbonyl-methylamino-acetic acid (13S,15R)-13-methyl-17[(E)-methoxyimino]-15-[2-(5-methyl-thiazol-2-ylcarbamoyl)-ethyl]-7,8,9,11,12,13,14,15,16,17-decahydro-6H-cyclopenta[a]phenanthren-3-yl ester;

Compound 5 Methylamino-acetic acid (13S,15R)-13-methyl-17[(E)-methoxyimino]-15-[2-(5-methyl-thiazol-2-ylcarbamoyl)-ethyl]-7,8,9,11,12,13,14,15,16,17-decahydro-6H-cyclopenta[a]phenanthren-3-yl ester;

Compound 6 Morpholin-4-yl-acetic acid (13S,15R)-13-methyl-17[(E)-methoxyimino]-15-[2-(5-methyl-thiazol-2-ylcarbamoyl)-ethyl]-7,8,9,11,12,13,14,15,16,17-decahydro-6H-cyclopenta[a]phenanthren-3-yl ester;

Compound 7 1-(tert-butyl)2-(13S,15R,E)-17-(methoxyimino)-13-methyl-15-(3-((5-methylthiazol-2-yl)amino)-3-oxopropyl)-7,8,9,11,12,13,14,15,16,17-decahydro-6H-cyclopenta[a]phenanthren-3-yl)pyrrolidine-1,2-dicarboxylate;

Compound 8 (13S,15R,E)-17-(methoxyimino)-13-methyl-15-(3-((5-methylthiazol-2-yl)amino)-3-oxopropyl)-7,8,9,11,12,13,14,15,16,17-decahydro-6H-cyclopenta[a] phenanthren-3-yl prolinate;

Compound 9 di-tert-butyl(((((13S,15R,E)-17-(methoxyimino)-13-methyl-15-(3-((5-methylthiazol-2-yl)amino)-3-oxopropyl)-7,8,9,11,12,13,14,15,16,17-decahydro-6H-cyclopenta[a]phenanthren-3-yl)oxy)-methyl) phosphate;

Compound 10 (((13S,15R,E)-17-(methoxyimino)-13-methyl-15-(3-((5-methylthiazol-2-yl)amino)-3-oxopropyl)-7,8,9,11,12,13,14,15,16,17-decahydro-6H-cyclopenta[a]phenanthren-3-yl)oxy)methyl dihydrogen phosphate;

Compound 11 (13S,15R,E)-2,4-dibromo-17-(hydroxyimino)-13-methyl-15-(3-((5-methylthiazol-2-yl)amino)-3-oxopropyl)-7,8,9,11,12,13,14,15,16,17-decahydro-6H-cyclopenta[a]phenanthren-3-yl acetate;

Compound 12 (13S,15R,E)-2,4-dibromo-17-(methoxyimino)-13-methyl-15-(3-((5-methylthiazol-2-yl)amino)-3-oxopropyl)-7,8,9,11,12,13,14,15,16,17-decahydro-6H-cyclopenta[a]phenanthren-3-yl dihydrogen phosphate;

Compound 13 (13S,15R,Z)-2,4-dibromo-17-(methoxyimino)-13-methyl-15-(3-((5-methylthiazol-2-yl)amino)-3-oxopropyl)-7,8,9,11,12,13,14,15,16,17-decahydro-6H-cyclopenta[a]phenanthren-3-yl dimethylglycinate;

Compound 14 (13S,15R,E)-2-iodo-17-(methoxyimino)-13-methyl-15-(3-((5-methylthiazol-2-yl)amino)-3-oxopropyl)-7,8,9,11,12,13,14,15,16,17-decahydro-6H-cyclopenta[a]phenanthren-3-yl dimethylglycinate;

Compound 15 (13S,15R,E)-2-iodo-17-(methoxyimino)-13-methyl-15-(3-((5-methylthiazol-2-yl)amino)-3-oxopropyl)-7,8,9,11,12,13,14,15,16,17-decahydro-6H-cyclopenta[a]phenanthren-3-yl dimethylglycinate;

Compound 16 (13S,15R,E)-2-iodo-17-(methoxyimino)-13-methyl-15-(3-((5-methylthiazol-2-yl)amino)-3-oxopropyl)-7,8,9,11,12,13,14,15,16,17-decahydro-6H-cyclopenta[a]phenanthren-3-yl dihydrogen phosphate;

Compound 17 (13S,15R,E)-17-(methoxyimino)-13-methyl-15-(3-((5-methylthiazol-2-yl)amino)-3-oxopropyl)-4-nitro-7,8,9,11,12,13,14,15,16,17-decahydro-6H-cyclopenta[a]phenanthren-3-yl dihydrogen phosphate;

Compound 18 (13S,15R,E)-17-(hydroxyimino)-13-methyl-15-(3-((5-methylthiazol-2-yl)amino)-3-oxopropyl)-4-nitro-7,8,9,11,12,13,14,15,16,17-decahydro-6H-cyclopenta[a]phenanthren-3-yl dihydrogen phosphate;

Compound 19 (13S,15R,E)-4-bromo-17-(hydroxyimino)-13-methyl-15-(3-((5-methylthiazol-2-yl)amino)-3-oxopropyl)-7,8,9,11,12,13,14,15,16,17-decahydro-6H-cyclopenta[a]phenanthren-3-yl dihydrogen phosphate;

Compound 20 (13S,15R,E)-2,4-diiodo-17-(methoxyimino)-13-methyl-15-(3-((5-methylthiazol-2-yl)amino)-3-oxopropyl)-7,8,9,11,12,13,14,15,16,17-decahydro-6H-cyclopenta[a]phenanthren-3-yl dimethylglycinate;

Compound 21 (13S,15R,E)-2,4-dibromo-17-(hydroxyimino)-13-methyl-15-(3-((5-methylthiazol-2-yl)amino)-3-oxopropyl)-7,8,9,11,12,13,14,15,16,17-decahydro-6H-cyclopenta[a]phenanthren-3-yl dihydrogen phosphate;

Compound 22 (13S,15R,E)-2,4-diiodo-17-(methoxyimino)-13-methyl-15-(3-((5-methylthiazol-2-yl)amino)-3-oxopropyl)-7,8,9,11,12,13,14,15,16,17-decahydro-6H-cyclopenta[a]phenanthren-3-yl dihydrogen phosphate;

and pharmaceutically acceptable salts thereof.

In another aspect of the present invention relates to a compound of formula (I) selected from the group consisting of:

Compound 1 Phosphoric acid mono-{(13S,15R)-17[(E)-methoxyimino]-13-methyl-15-[2-(5-methylthiazol-2-ylcarbamoyl)ethyl-7,8,9,11,12,13,14,15,16,17-decahydro-6H-cyclopenta[a]phenanthren-3-yl} ester;

Compound 1a Phosphoric acid mono-{(13S,15R)-17-[(E)-methoxyimino]-13-methyl-15-[2-(5-methylthiazol-2-ylcarbamoyl)ethyl-7,8,9,11,12,13,14,15,16,17-decahydro-6H-cyclopenta[a]phenanthren-3-yl} ester disodium salt Compound 2 tert-Butoxycarbonylamino-acetic acid (13S,15R)-13-methyl-17[(E)-methoxyimino]-15-[2-(5-methyl-thiazol-2-ylcarbamoyl)-ethyl]-7,8,9,11,12,13,14,15,16,17-decahydro-6H-cyclopenta[a]phenanthren-3-yl ester;

Compound 3a Aminoacetic acid (13S,15R)-13-methyl-17[(E)-methoxyimino]-15-[2-(5-methyl-thiazol-2-ylcarbamoyl)-ethyl]-7,8,9,11,12,13,14,15,16,17-decahydro-6H-cyclopenta[a]phenanthren-3-yl ester trifluoroacetate;

Compound 3b Aminoacetic acid (13S,15R)-13-methyl-17[(E)-methoxyimino]-15-[2-(5-methyl-thiazol-2-ylcarbamoyl)-ethyl]-7,8,9,11,12,13,14,15,16,17-decahydro-6H-cyclopenta[a]phenanthren-3-yl ester hydrochloride;

Compound 4 Tert-Butoxycarbonyl-methylamino-acetic acid (13S,15R)-13-methyl-17[(E)-methoxyimino]-15-[2-(5-methyl-thiazol-2-ylcarba-moyl)-ethyl]-7,8,9,11,12,13,14,15,16,17-decahydro-6H-cyclopenta[a]phenanthren-3-yl ester;

Compound 5a Methylamino-acetic acid (13S,15R)-13-methyl-17[(E)-methoxyimino]-15-[2-(5-methyl-thiazol-2-ylcarbamoyl)-ethyl]-7,8,9,11,12,13,14,15,16,17-decahydro-6H-cyclopenta[a]phenanthren-3-yl ester hydrochloride;

Compound 6 Morpholin-4-yl-acetic acid (13S,15R)-13-methyl-17[(E)-methoxyimino]-15-[2-(5-methyl-thiazol-2-ylcarbamoyl)-ethyl]-7,8,9,11,12,13,14,15,16,17-decahydro-6H-cyclopenta[a]phenanthren-3-yl ester;

Compound 7 1-(tert-butyl)2-(13S,15R,E)-17-(methoxyimino)-13-methyl-15-(3-((5-methylthiazol-2-yl)amino)-3-oxopropyl)-7,8,9,11,12,13,14,15,16,17-decahydro-6H-cyclopenta[a]phenanthren-3-yl) pyrrolidine-1,2-dicarboxylate;

Compound 8a (13S,15R,E)-17-(methoxyimino)-13-methyl-15-(3-((5-methylthiazol-2-yl)amino)-3-oxopropyl)-7,8,9,11,12,13,14,15,16,17-decahydro-6H-cyclopenta[a] phenanthren-3-yl prolinate trifluoroacetate;

Compound 8b (13S,15R,E)-17-(methoxyimino)-13-methyl-15-(3-((5-methylthiazol-2-yl)amino)-3-oxopropyl)-7,8,9,11,12,13,14,15,16,17-decahydro-6H-cyclopenta[a] phenanthren-3-yl prolinate hydrochloride;

Compound 9 di-tert-butyl(((((13S,15R,E)-17-(methoxyimino)-13-methyl-15-(3-((5-methylthiazol-2-yl)amino)-3-oxopropyl)-7,8,9,11,12,13,14,15,16,17-decahydro-6H-cyclopenta[a]phenanthren-3-yl)oxy)-methyl) phosphate;

Compound 10 (((13S,15R,E)-17-(methoxyimino)-13-methyl-15-(3-((5-methylthiazol-2-yl)amino)-3-oxopropyl)-7,8,9,11,12,13,14,15,16,17-decahydro-6H-cyclopenta[a]phenanthren-3-yl)oxy)methyl dihydrogen phosphate;

Compound 10a (((13S,15R,E)-17-(methoxyimino)-13-methyl-15-(3-((5-methylthiazol-2-yl)amino)-3-oxopropyl)-7,8,9,11,12,13,14,15,16,17-decahydro-6H-cyclopenta[a]phenanthren-3-yl)oxy)-methyl dihydrogen phosphate disodium salt;

Compound 11 (13S,15R,E)-2,4-dibromo-17-(hydroxyimino)-13-methyl-15-(3-((5-methylthiazol-2-yl)amino)-3-oxopropyl)-7,8,9,11,12,13,14,15,16,17-decahydro-6H-cyclopenta[a]phenanthren-3-yl acetate;

Compound 12 (13S,15R,E)-2,4-dibromo-17-(methoxyimino)-13-methyl-15-(3-((5-methylthiazol-2-yl)amino)-3-oxopropyl)-7,8,9,11,12,13,14,15,16,17-decahydro-6H-cyclopenta[a]phenanthren-3-yl acetate;

Compound 13 (13S,15R,E)-2,4-dibromo-17-(methoxyimino)-13-methyl-15-(3-((5-methylthiazol-2-yl)amino)-3-oxopropyl)-7,8,9,11,12,13,14,15,16,17-decahydro-6H-cyclopenta[a]phenanthren-3-yl dihydrogen phosphate;

Compound 14 (13S,15R,Z)-2,4-dibromo-17-(methoxyimino)-13-methyl-15-(3-((5-methylthiazol-2-yl)amino)-3-oxopropyl)-7,8,9,11,12,13,14,15,16,17-decahydro-6H-cyclopenta[a]phenanthren-3-yl dimethylglycinate;

Compound 14a (13S,15R,Z)-2,4-dibromo-17-(methoxyimino)-13-methyl-15-(3-((5-methylthiazol-2-yl)amino)-3-oxopropyl)-7,8,9,11,12,13,14,15,16,17-decahydro-6H-cyclopenta[a]phenanthren-3-yl dimethylglycinate hydrochloride;

Compound 15 (13S,15R,E)-2-iodo-17-(methoxyimino)-13-methyl-15-(3-((5-methylthiazol-2-yl)amino)-3-oxopropyl)-7,8,9,11,12,13,14,15,16,17-decahydro-6H-cyclopenta[a]phenanthren-3-yl dimethylglycinate;

Compound 16 (13S,15R,E)-2-iodo-17-(methoxyimino)-13-methyl-15-(3-((5-methylthiazol-2-yl)amino)-3-oxopropyl)-7,8,9,11,12,13,14,15,16,17-decahydro-6H-cyclopenta[a]phenanthren-3-yl dihydrogen phosphate;

Compound 16a (13S,15R,E)-2-iodo-17-(methoxyimino)-13-methyl-15-(3-((5-methylthiazol-2-yl)amino)-3-oxopropyl)-7,8,9,11,12,13,14,15,16,17-decahydro-6H-cyclopenta[a]phenanthren-3-yl dihydrogen phosphate disodium salt;

Compound 17 (13S,15R,E)-17-(methoxyimino)-13-methyl-15-(3-((5-methylthiazol-2-yl)amino)-3-oxopropyl)-4-nitro-7,8,9,11,12,13,14,15,16,17-decahydro-6H-cyclopenta[a]phenanthren-3-yl dihydrogen phosphate;

Compound 17a Disodium (13S,15R,E)-17-(methoxyimino)-13-methyl-15-(3-((5-methylthiazol-2-yl)amino)-3-oxopropyl)-4-nitro-7,8,9,11,12,13,14,15,16,17-decahydro-6H-cyclopenta[a]phenanthren-3-yl dihydrogen phosphate;

Compound 18 (13S,15R,E)-17-(hydroxyimino)-13-methyl-15-(3-((5-methylthiazol-2-yl)amino)-3-oxopropyl)-4-nitro-7,8,9,11,12,13,14,15,16,17-decahydro-6H-cyclopenta[a]phenanthren-3-yl dihydrogen phosphate;

Compound 19 (13S,15R,E)-4-bromo-17-(hydroxyimino)-13-methyl-15-(3-((5-methylthiazol-2-yl)amino)-3-oxopropyl)-7,8,9,11,12,13,14,15,16,17-decahydro-6H-cyclopenta[a]phenanthren-3-yl dihydrogen phosphate;

Compound 19a Sodium (13S,15R,E)-4-bromo-17-(hydroxyimino)-13-methyl-15-(3-((5-methylthiazol-2-yl)amino)-3-oxopropyl)-7,8,9,11,12,13,14,15,16,17-decahydro-6H-cyclopenta[a]phenanthren-3-yl phosphate;

Compound 20 (13S,15R,E)-2,4-diiodo-17-(methoxyimino)-13-methyl-15-(3-((5-methylthiazol-2-yl)amino)-3-oxopropyl)-7,8,9,11,12,13,14,15,16,17-decahydro-6H-cyclopenta[a]phenanthren-3-yl dimethylglycinate; and Compound 21 (13S,15R,E)-2,4-dibromo-17-(hydroxyimino)-13-methyl-15-(3-((5-methylthiazol-2-yl)amino)-3-oxopropyl)-7,8,9,11,12,13,14,15,16,17-decahydro-6H-cyclopenta[a]phenanthren-3-yl dihydrogen phosphate;

Compound 22 (13S,15R,E)-2,4-diiodo-17-(methoxyimino)-13-methyl-15-(3-((5-methylthiazol-2-yl)amino)-3-oxopropyl)-7,8,9,11,12,13,14,15,16,17-decahydro-6H-cyclopenta[a]phenanthren-3-yl dihydrogen phosphate.

EXAMPLES OF THE THERAPEUTICALLY ACTIVE ENTITIES OF FORMULA (VII)

Representative examples of the active species liberated by the compounds of formula (I) are shown in Table 1.

TABLE 1

| # | Compound |
|---|---|
| VIV-1 | 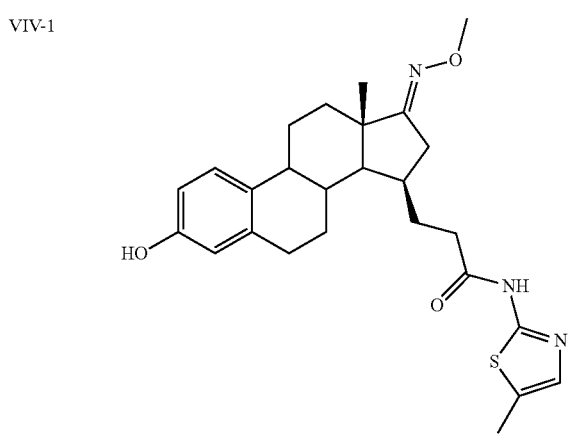 |
| VIV-2 | 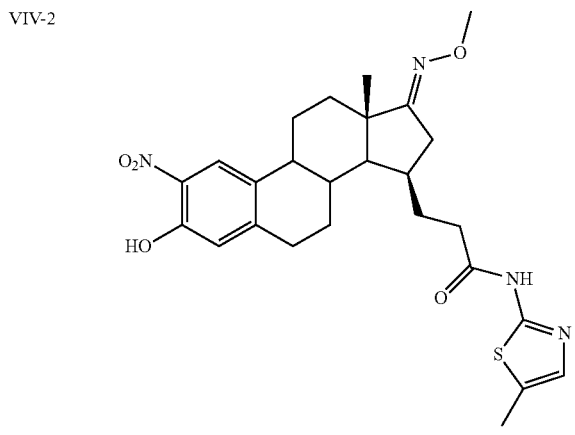 |

TABLE 1-continued
| # | Compound |
|---|---|
| VIV-3 | 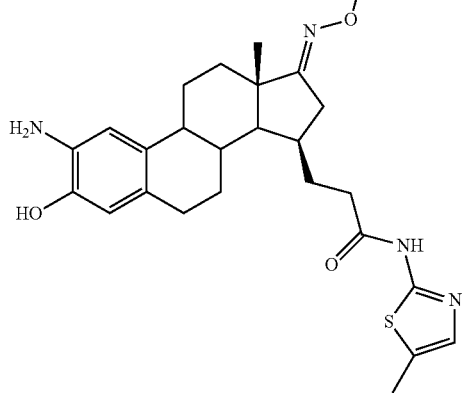 |
| VIV-4 | 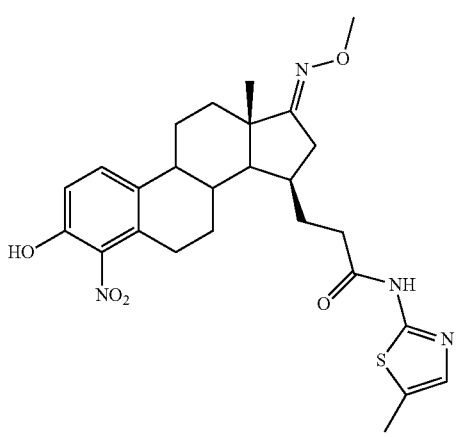 |
| VIV-5 | 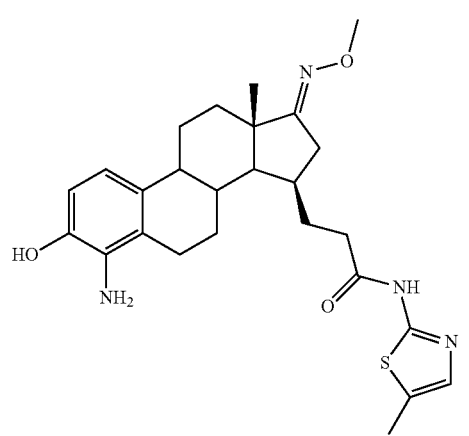 [SMILES: CO/N=C1\C[C@@H](CCC(=O)Nc2ncc(C)s2)C2C3CCc4c(ccc(O)c4N)C3CC[C@]12C] |
| VIV-6 | 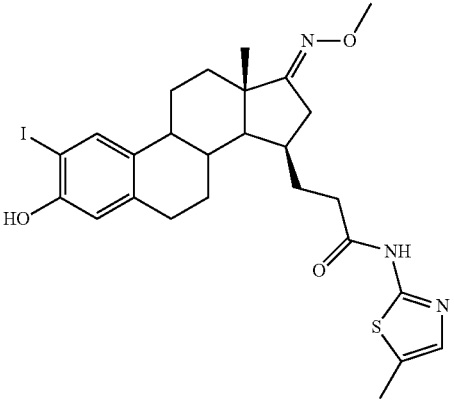 [SMILES: CO/N=C1\C[C@@H](CCC(=O)Nc2ncc(C)s2)C2C3CCc4cc(O)c(I)cc4C3CC[C@]12C] |
| VIV-7 | 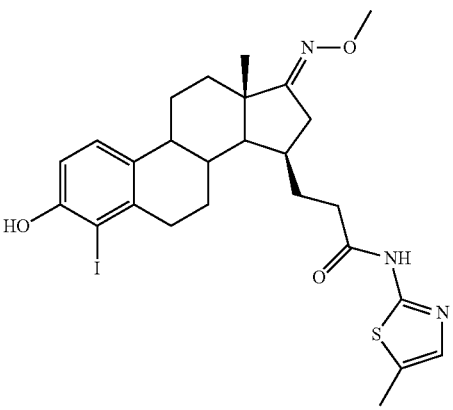 [SMILES: CO/N=C1\C[C@@H](CCC(=O)Nc2ncc(C)s2)C2C3CCc4c(ccc(O)c4I)C3CC[C@]12C] |
| VIV-8 | 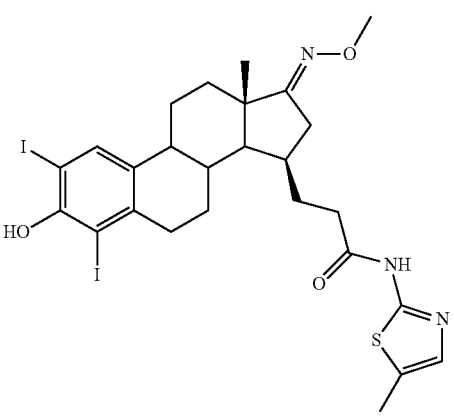 [SMILES: CO/N=C1\C[C@@H](CCC(=O)Nc2ncc(C)s2)C2C3CCc4c(cc(I)c(O)c4I)C3CC[C@]12C] |

TABLE 1-continued

| # | Compound |
|---|---|
| VIV-9 | (structure: 2-bromo-3-hydroxy estra-derivative with 17-methoxyimino and 15-propanamide-N-(5-methylthiazol-2-yl)) |
| VIV-10 | (structure: 4-bromo-3-hydroxy estra-derivative with 17-methoxyimino and 15-propanamide-N-(5-methylthiazol-2-yl)) |
| VIV-11 | (structure: 2,4-dibromo-3-hydroxy estra-derivative with 17-methoxyimino and 15-propanamide-N-(5-methylthiazol-2-yl)) |
| VIV-12 | (structure: 2-chloro-3-hydroxy estra-derivative with 17-methoxyimino and 15-propanamide-N-(5-methylthiazol-2-yl)) |
| VIV-13 | (structure: 4-chloro-3-hydroxy estra-derivative with 17-methoxyimino and 15-propanamide-N-(5-methylthiazol-2-yl)) |
| VIV-14 | (structure: 2,4-dichloro-3-hydroxy estra-derivative with 17-methoxyimino and 15-propanamide-N-(5-methylthiazol-2-yl)) |

TABLE 1-continued

| # | Compound |
|---|---|
| VIV-15 | (structure: estradiol-derived core with 4-F, 3-OH, 17-N-OMe oxime, and 15-CH2CH2C(O)NH-(5-methylthiazol-2-yl) side chain) |
| VIV-16 | (structure: 2-F, 3-OH analog) |
| VIV-17 | (structure: 2-Br, 3-OH, 4-F analog) |
| VIV-18 | (structure: 2-F, 3-OH, 4-Br analog) |
| VIV-19 | (structure: 2-CN, 3-OH analog) |
| VIV-20 | (structure: 3-OH, 4-CN analog) |

TABLE 1-continued
| # | Compound |
|---|---|
| VIV-21 | 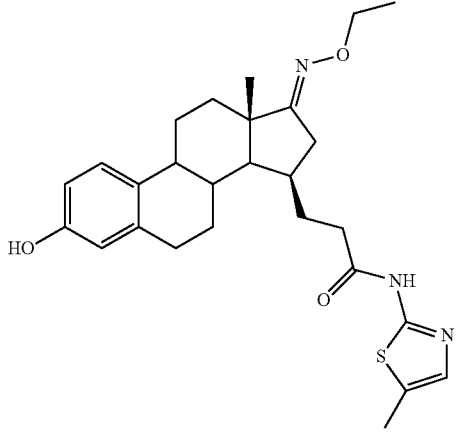 [SMILES: CCO/N=C1\C[C@@H](CCC(=O)Nc2ncc(C)s2)C2C3CCc4cc(O)ccc4C3CC[C@]12C] |
| VIV-22 | 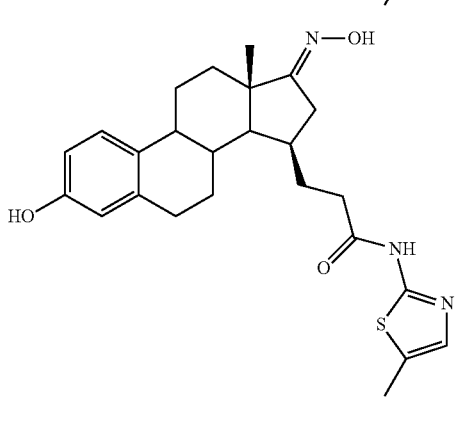 |
| VIV-23 | 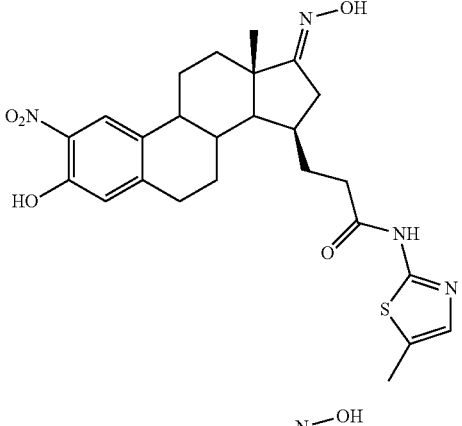 |
| VIV-24 | 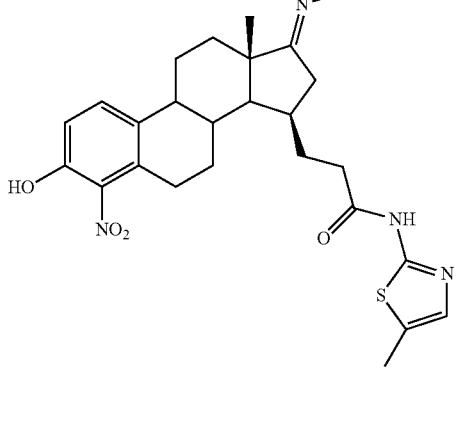 |
| VIV-25 | 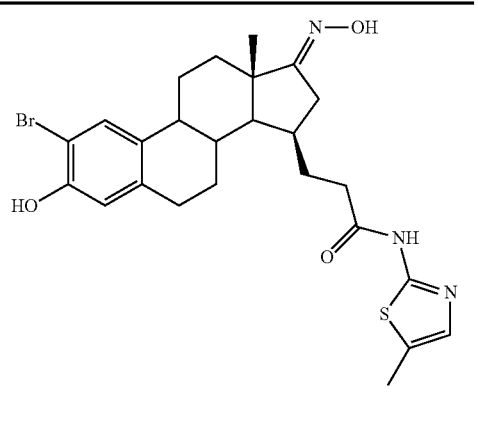 |
| VIV-26 | 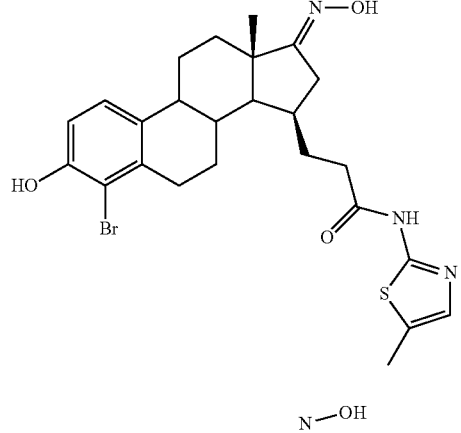 |
| VIV-27 | 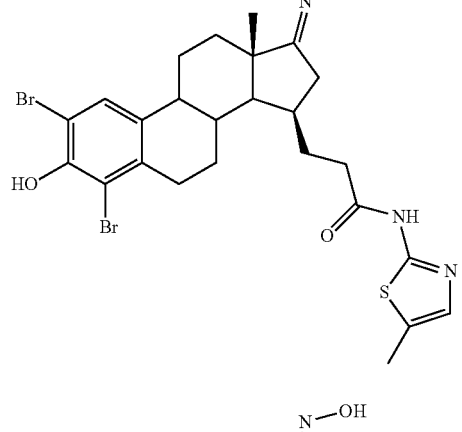 |
| VIV-28 | 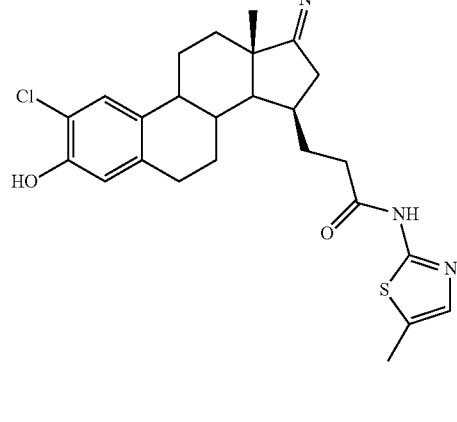 |

TABLE 1-continued
| # | Compound |
|---|---|
| VIV-29 | 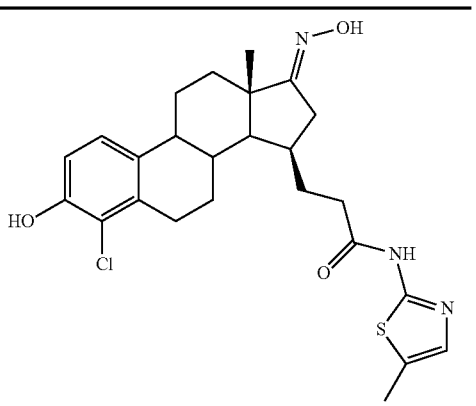 |
| VIV-30 | 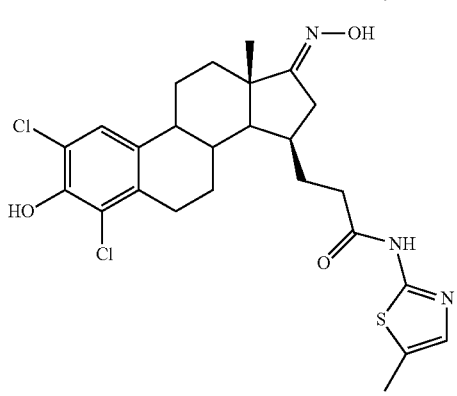 [SMILES: Cc1cnc(NC(=O)CC[C@@H]2C/C(=N\O)[C@@]3(C)CCC4c5cc(Cl)c(O)c(Cl)c5CCC4C23)s1] |
TABLE 1-continued
| # | Compound |
|---|---|
| VIV-31 | 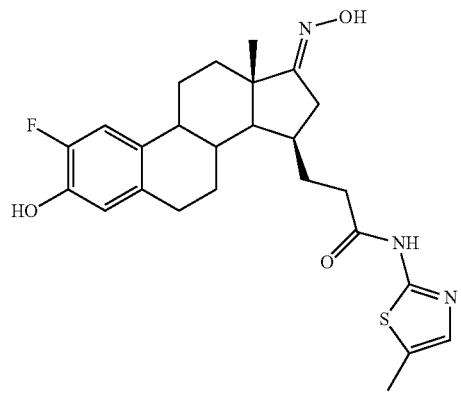 [SMILES: Cc1cnc(NC(=O)CC[C@@H]2C/C(=N\O)[C@@]3(C)CCC4c5cc(F)c(O)cc5CCC4C23)s1] |
EXAMPLES OF THE INVENTION
Representative examples of compounds of formula (I) are shown in Table 2.
TABLE 2
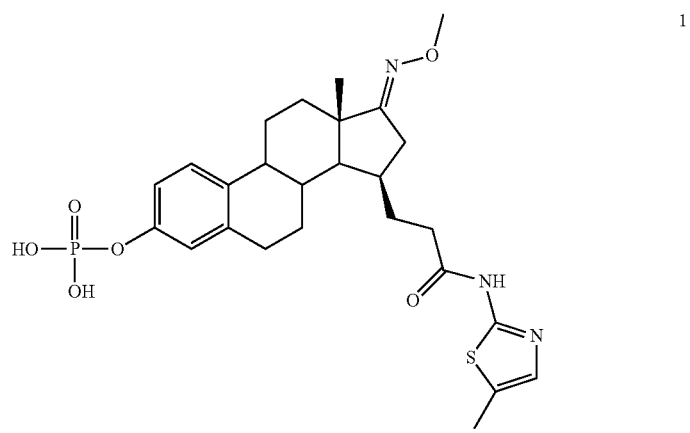
1

TABLE 2-continued
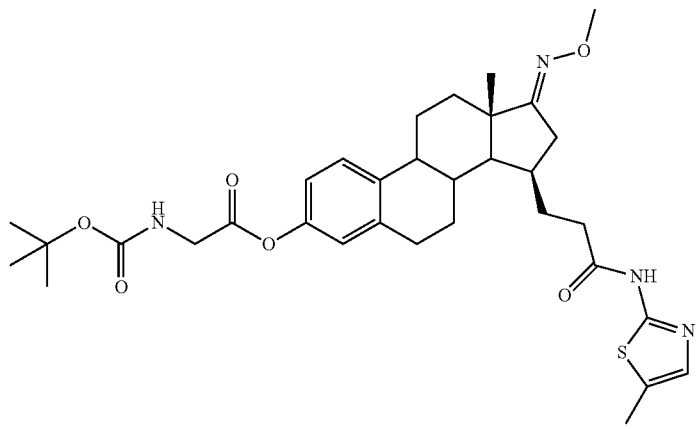 [SMILES: CO/N=C1\C[C@@H](CCC(=O)Nc2ncc(C)s2)C2C3CCc4cc(OC(=O)CNC(=O)OC(C)(C)C)ccc4C3CC[C@]12C]
2
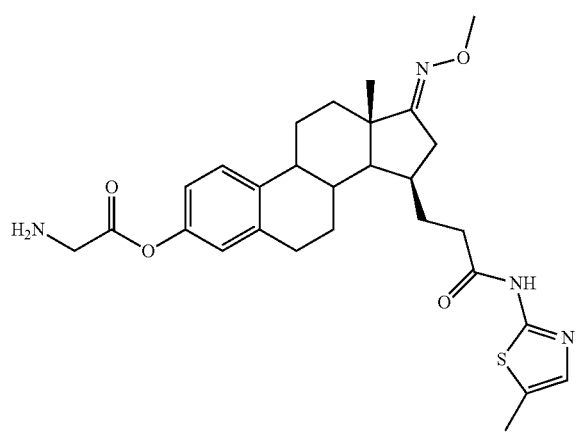 [SMILES: CO/N=C1\C[C@@H](CCC(=O)Nc2ncc(C)s2)C2C3CCc4cc(OC(=O)CN)ccc4C3CC[C@]12C]
3
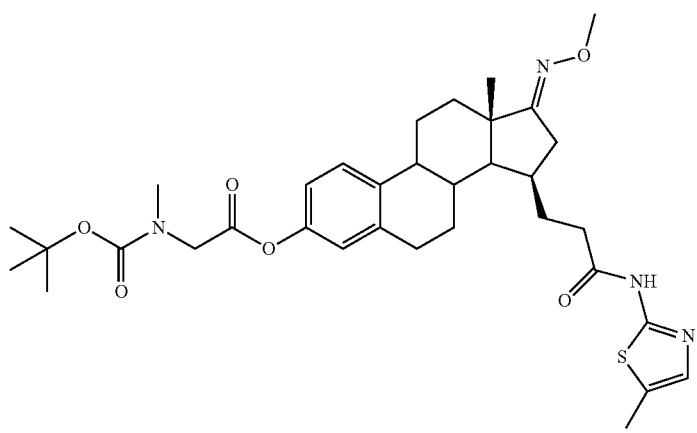 [SMILES: CO/N=C1\C[C@@H](CCC(=O)Nc2ncc(C)s2)C2C3CCc4cc(OC(=O)CN(C)C(=O)OC(C)(C)C)ccc4C3CC[C@]12C]
4

TABLE 2-continued
| | |
|---|---|
| 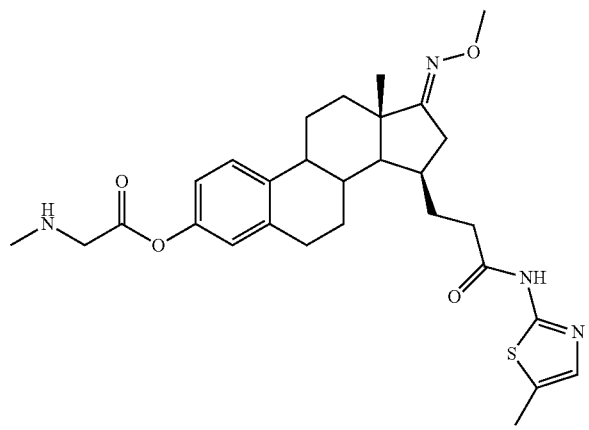 [SMILES: CNCC(=O)Oc1ccc2c(c1)CCC1C2CC[C@]2(C)/C(=N/OC)C[C@@H](CCC(=O)Nc3ncc(C)s3)C12] | 5 |
| 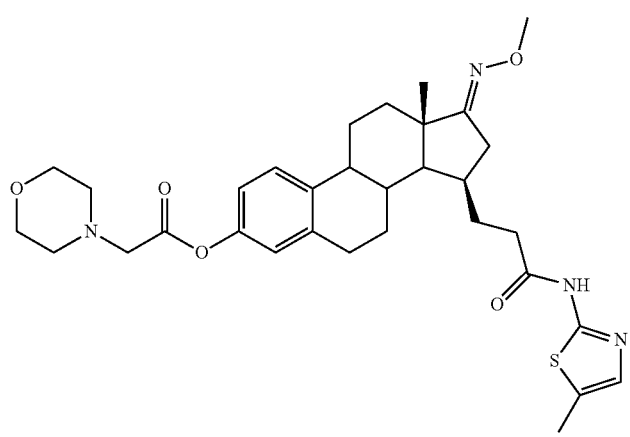 [SMILES: CO/N=C1\C[C@@H](CCC(=O)Nc2ncc(C)s2)C2C3CCc4cc(OC(=O)CN5CCOCC5)ccc4C3CC[C@]12C] | 6 |
| 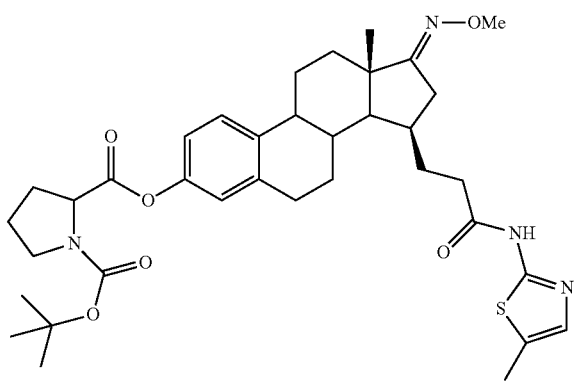 [SMILES: CO/N=C1\C[C@@H](CCC(=O)Nc2ncc(C)s2)C2C3CCc4cc(OC(=O)C5CCCN5C(=O)OC(C)(C)C)ccc4C3CC[C@]12C] | 7 |
| 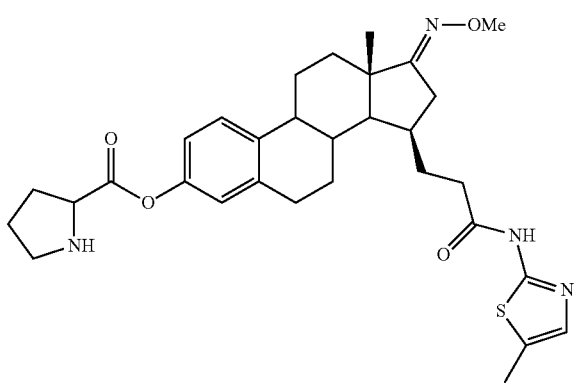 [SMILES: CO/N=C1\C[C@@H](CCC(=O)Nc2ncc(C)s2)C2C3CCc4cc(OC(=O)C5CCCN5)ccc4C3CC[C@]12C] | 8 |

TABLE 2-continued
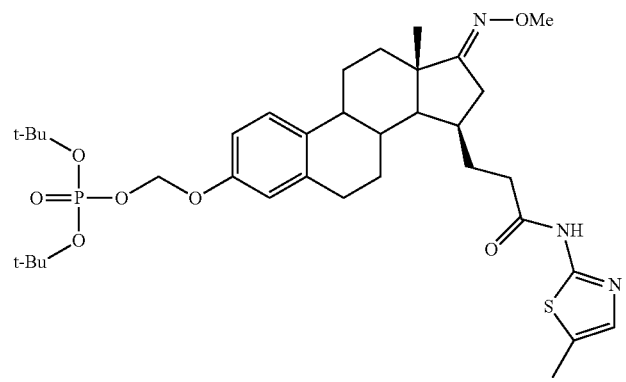 [SMILES: CO/N=C1\C[C@@H](CCC(=O)Nc2ncc(C)s2)C2C3CCc4cc(OCOP(=O)(OC(C)(C)C)OC(C)(C)C)ccc4C3CC[C@]12C]
9
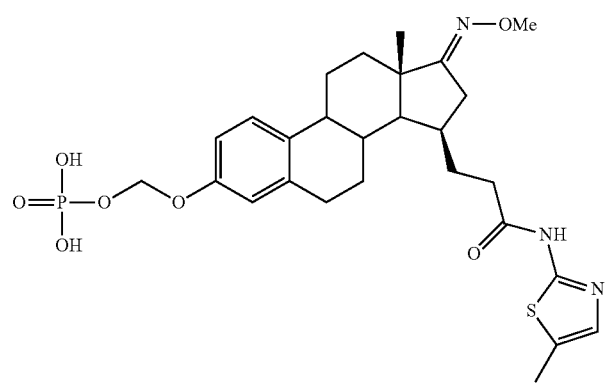 [SMILES: CO/N=C1\C[C@@H](CCC(=O)Nc2ncc(C)s2)C2C3CCc4cc(OCOP(=O)(O)O)ccc4C3CC[C@]12C]
10
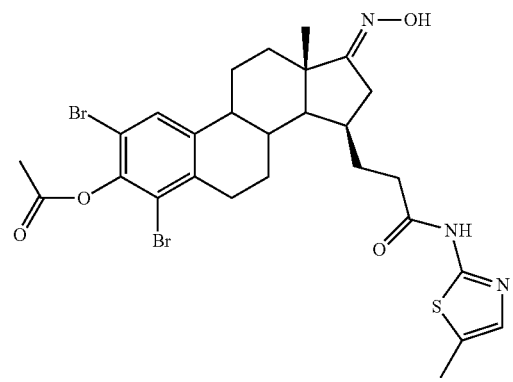 [SMILES: CC(=O)Oc1c(Br)cc2c(c1Br)CCC1C2CC[C@]2(C)/C(=N/O)C[C@@H](CCC(=O)Nc3ncc(C)s3)C12]
11
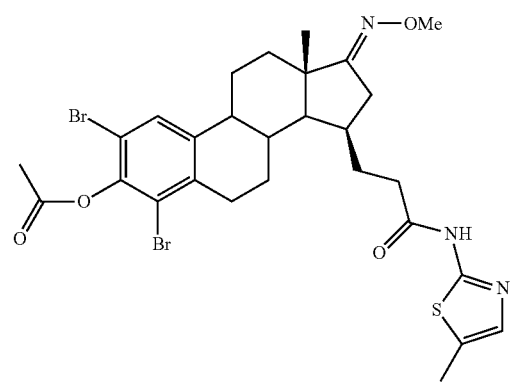 [SMILES: CO/N=C1\C[C@@H](CCC(=O)Nc2ncc(C)s2)C2C3CCc4c(cc(Br)c(OC(C)=O)c4Br)C3CC[C@]12C]
12

TABLE 2-continued
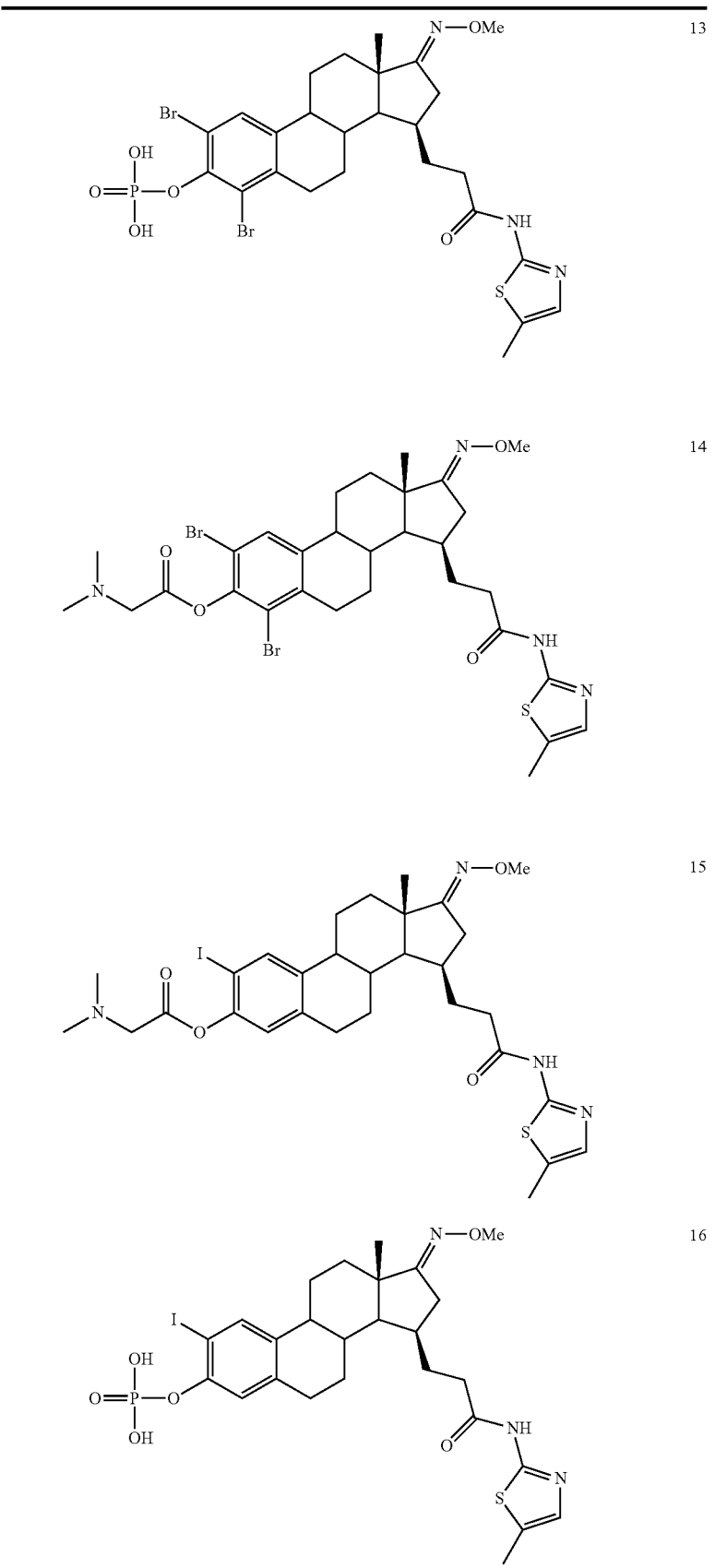

TABLE 2-continued
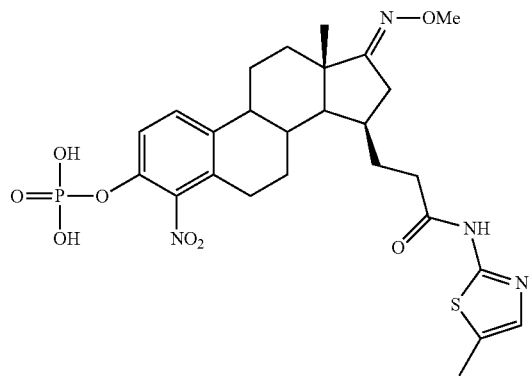 [SMILES: CO/N=C1\C[C@@H](CCC(=O)Nc2ncc(C)s2)C2C3CCc4c(ccc(OP(=O)(O)O)c4[N+](=O)[O-])C3CC[C@]12C] 17
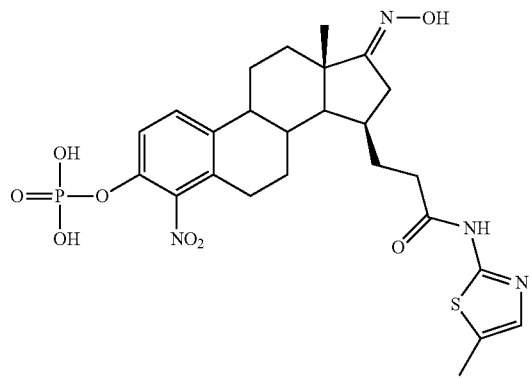 [SMILES: Cc1cnc(NC(=O)CC[C@@H]2C/C(=N\O)[C@@]3(C)CCC4c5ccc(OP(=O)(O)O)c([N+](=O)[O-])c5CCC4C23)s1] 18
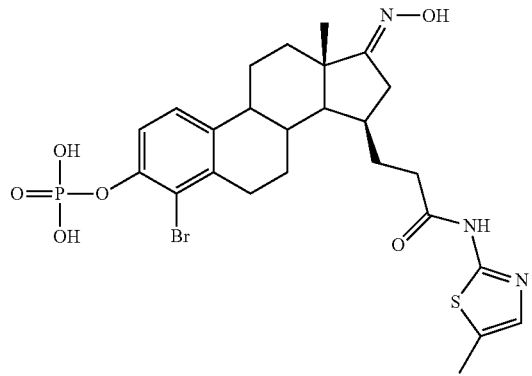 [SMILES: Cc1cnc(NC(=O)CC[C@@H]2C/C(=N\O)[C@@]3(C)CCC4c5ccc(OP(=O)(O)O)c(Br)c5CCC4C23)s1] 19
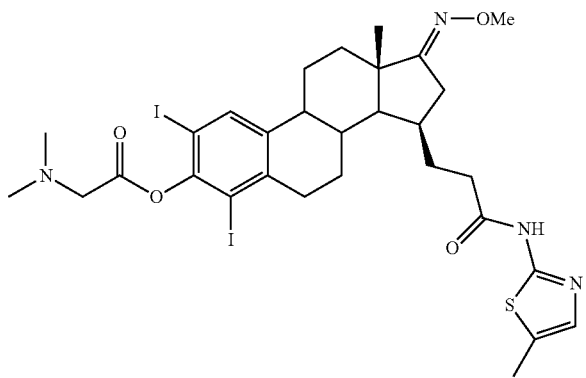 [SMILES: CO/N=C1\C[C@@H](CCC(=O)Nc2ncc(C)s2)C2C3CCc4c(cc(I)c(OC(=O)CN(C)C)c4I)C3CC[C@]12C] 20

TABLE 2-continued

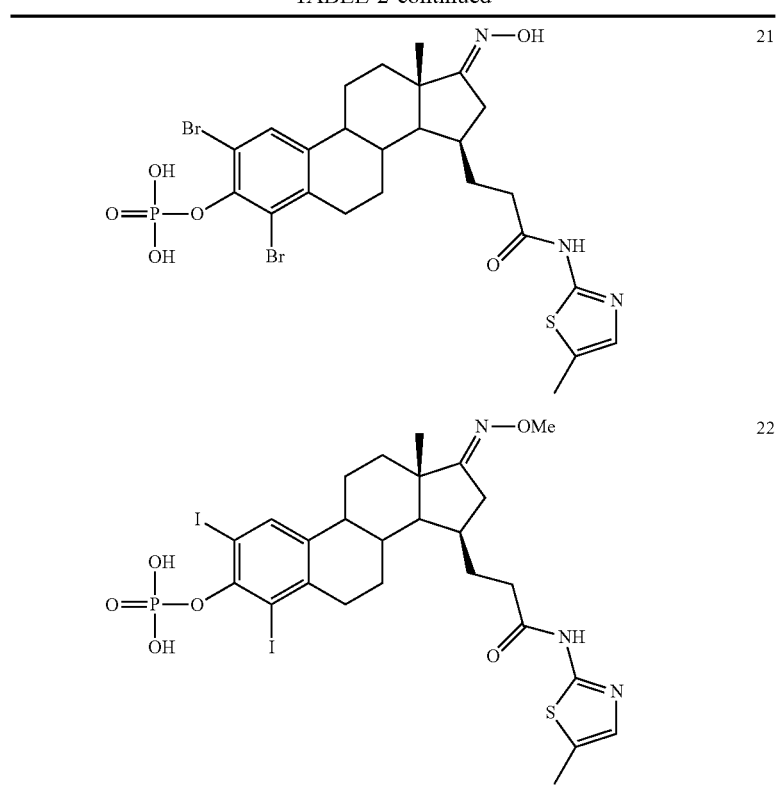

General Preparation Methods

Compounds of the present invention may be prepared by methods known in the art. The following examples illustrate the preparation of compounds of formula (I).

General Information

Commercial grade reagents and solvents were used without further purification. Thin-layer chromatography (TLC) was performed on Merck-plates; pre-coated aluminium sheets. Visualization of plates was done the following techniques: 1) ultraviolet illumination (254 nm), 2) dipping the plate into anisaldehyde or vanilline solution followed by heating. 1H-NMR spectra were measured with a Bruker DPX (200 MHz) spectrometer with the solvent as indicated.

Compounds of the invention may be prepared from the corresponding C-17 carbonyl derivatives wherein R2 is H, followed by required derivatization of the C3-OH group.

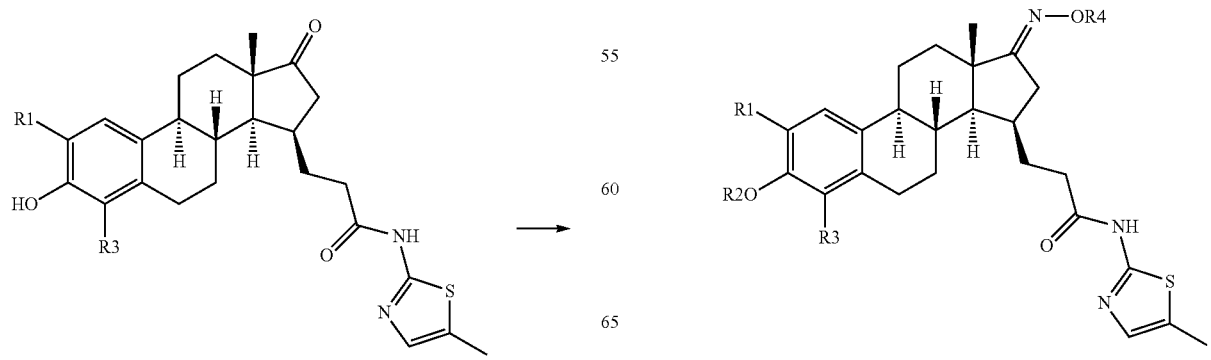

Preparation of Synthesis Starting Materials and Precursors
Compound VII

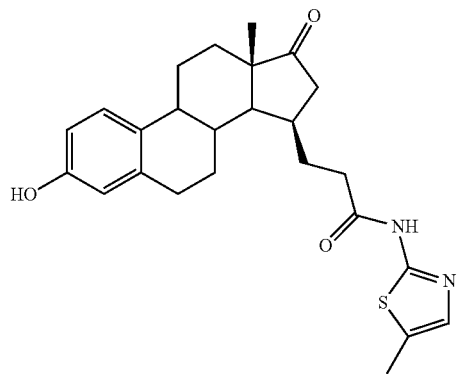 [SMILES: Cc1cnc(NC(=O)CC[C@@H]2CC(=O)[C@@]3(C)CCC4c5ccc(O)cc5CCC4C23)s1]

Compound VII may be synthesized as disclosed in Messinger et al. Mol Cell Endocrinol. 2009 (301) 216-224. The detailed synthesis of compound VII starting from estrone has been described in the Solvay Pharmaceuticals' PCT applications WO2005/047303 and WO2006/125800.

Benzyl-C15-C16-dehydroestrone II was prepared in five steps from estrone according to previously described methods. The compound II was treated with an allylic Grignard reagent in the presence of cuprous iodide and lithium chloride in temperature −78° C. Hydroboration by borane tetrahydrofuran complex at room temperature to compound III and following hydrogen peroxide oxidation in alkaline conditions produced diol IV in over 90% yields. Jones oxidation in acetone-water afforded acid V, which was debenzylated by hydrogenation to compound VI by using Pd/C as a catalyst. The final step was the amide formation affording the β-thiazole VII.

The synthesis of the key precursor i.e. the phenolic thiazole VII-1 from estrone is shown below.

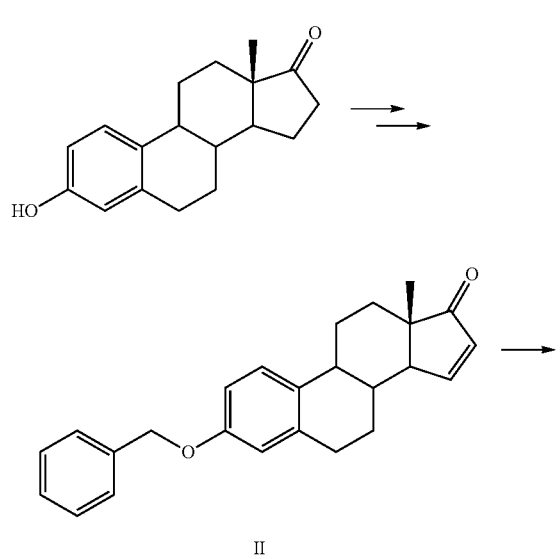

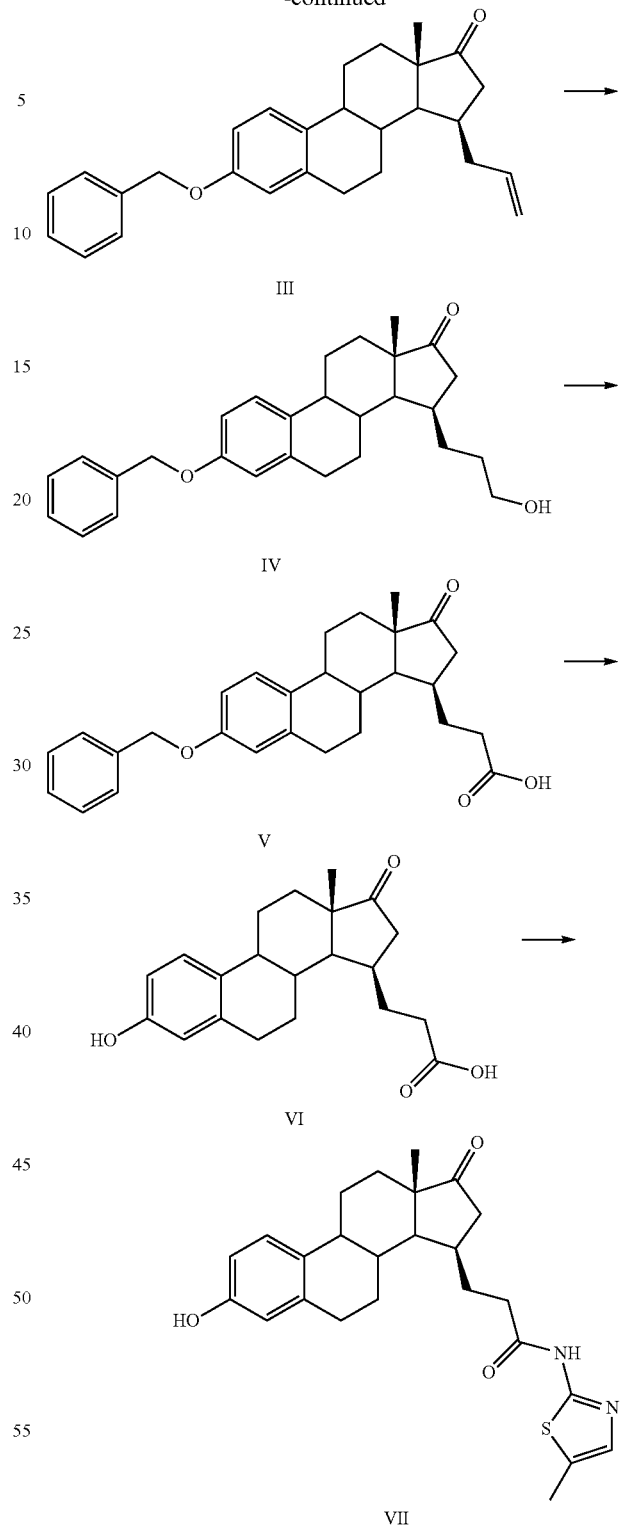

Preparation of C-17 Carbonyl Compounds
Nitration of the Compound VII

The reaction vessel was charged with the compound VII (1.32 g, 3 mmol) and ethanol (45 ml) under nitrogen atmosphere. Tetrahydrofuran (THF) (30 ml) and ferric nitrate (600 mg, 1.5 mmol) were added. After stirring the reaction mixture for 4 h at 60° C., the solvents were evaporated. HPLC of the crude reaction mixture showed 45% of 2-nitro-isomer VIII-1 and 35% of 4-nitroisomer VIII-2. Purification by flash chromatography gave 358 mg of VIII-1 and 284 mg of VIII-2. In addition, the product mixture contained ca. 5% of 2,4-dinitro derivative VIII-3.

Compound VIII-1

3-((13S,15R)-3-hydroxy-13-methyl-2-nitro-17-oxo-7,8,9,11,12,13,14,15,16,17-decahydro-6H-cyclopenta[a]phenanthren-15-yl)-N-(5-methylthiazol-2-yl)propanamide

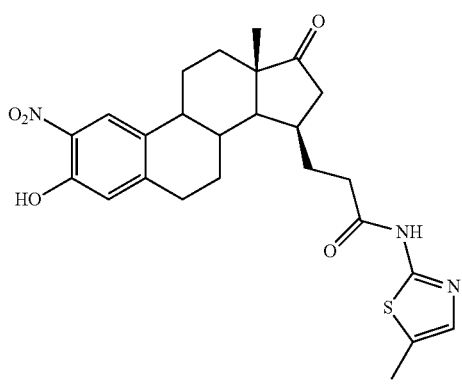 [SMILES: Cc1cnc(NC(=O)CC[C@@H]2CC(=O)[C@@]3(C)CCC4c5cc([N+](=O)[O-])c(O)cc5CCC4C23)s1]

$^1$H-NMR (CDCl$_3$): 1.07 (s, 3H), 1.30-2.75 (m, 19H), 2.9-3.05 (m, 2H), 6.89 (s, 1H), 7.05 (s, 1H), 7.98 (s, 1H). MS m/z (TOF ES$^+$): 506 (M+Na).

Compound VIII-2

3-((13S,15R)-3-hydroxy-13-methyl-4-nitro-17-oxo-7,8,9,11,12,13,14,15,16,17-decahydro-6H-cyclopenta[a]phenanthren-15-yl)-N-(5-methylthiazol-2-yl)propanamide

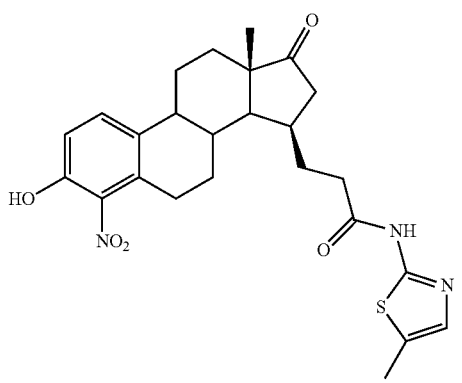 [SMILES: Cc1cnc(NC(=O)CC[C@@H]2CC(=O)[C@@]3(C)CCC4c5ccc(O)c([N+](=O)[O-])c5CCC4C23)s1]

$^1$H-NMR (CDCl$_3$): 1.08 (s, 3H), 1.3-3.4 (m, 21H), 6.96 (d, 1H), 7.05 (s, 1H), 7.45 (d, 1H). MS m/z (TOF ES$^+$): 506 (M+Na)

Compound VIII-3

3-((13S,15R)-3-hydroxy-13-methyl-2,4-dinitro-17-oxo-7,8,9,11,12,13,14,15,16,17-decahydro-6H-cyclopenta[a]phenanthren-15-yl)-N-(5-methylthiazol-2-yl)propanamide

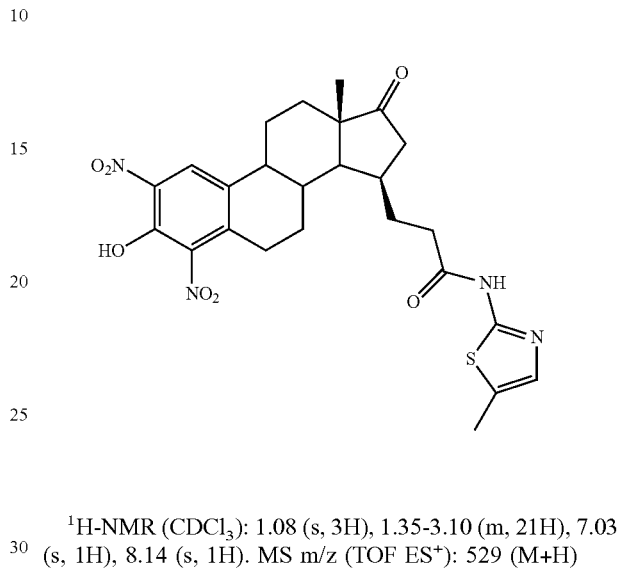

$^1$H-NMR (CDCl$_3$): 1.08 (s, 3H), 1.35-3.10 (m, 21H), 7.03 (s, 1H), 8.14 (s, 1H). MS m/z (TOF ES$^+$): 529 (M+H)

2- and 4 Aminoderivatives

Compound VIII-4

3-((13S,15R)-2-amino-3-hydroxy-13-methyl-17-oxo-7,8,9,11,12,13,14,15,16,17-decahydro-6H-cyclopenta[a]phenanthren-15-yl)-N-(5-methylthiazol-2-yl)propanamide

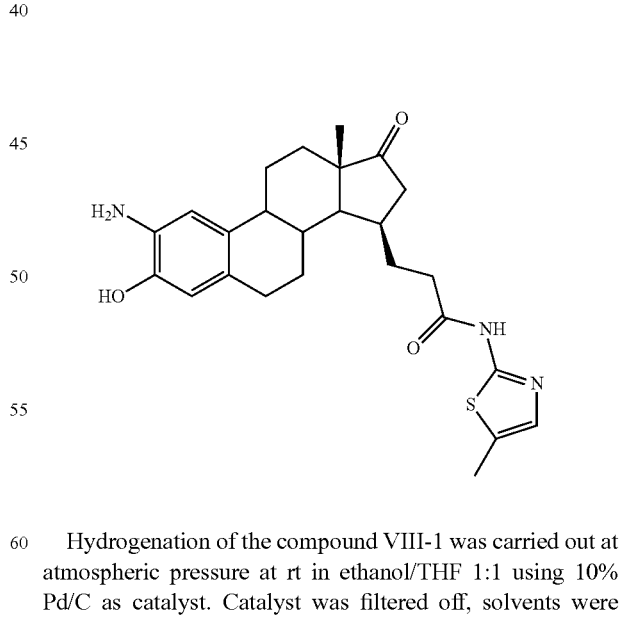

Hydrogenation of the compound VIII-1 was carried out at atmospheric pressure at rt in ethanol/THF 1:1 using 10% Pd/C as catalyst. Catalyst was filtered off, solvents were evaporated and product purified by flash chromatography.

$^1$H-NMR (CDCl$_3$+MeOH-d$_4$): 1.06 (s, 3H), 1.30-2.65 (m, 19H), 2.80-2.95 (m, 2H), 6.50 (s, 1H), 6.69 (s, 1H), 7.03 (s, 1H). MS m/z (TOF ES$^+$): 454 (M+H)

Compound VIII-5

3-((13S,15R)-4-amino-3-hydroxy-13-methyl-17-oxo-7,8,9,11,12,13,14,15,16,17-decahydro-6H-cyclopenta[a]phenanthren-15-yl)-N-(5-methylthiazol-2-yl)propanamide

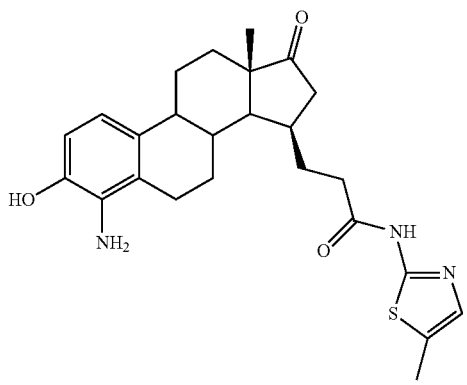 [SMILES: Cc1cnc(NC(=O)CC[C@@H]2CC(=O)[C@@]3(C)CCC4c5ccc(O)c(N)c5CCC4C23)s1]

Prepared according to method used for the compound VIII-4 using the compound VIII-2 as a starting material.

$^1$H-NMR (CDCl$_3$+MeOH-d$_4$): 1.03 (s, 3H), 1.35-2.65 (m, 19H), 2.75-3.00 (m, 2H), 6.63 (s, 2H), 7.03 (s, 1H). MS m/z (TOF ES$^+$): 476 (M+Na).

Halogenation of the Aromatic Ring

Compound VIII-6

3-((13S,15R)-3-hydroxy-2,4-diiodo-13-methyl-17-oxo-7,8,9,11,12,13,14,15,16,17-decahydro-6H-cyclopenta[a]phenanthren-15-yl)-N-(5-methylthiazol-2-yl)propanamide

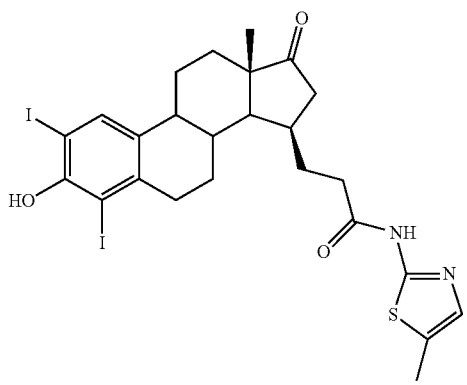 [SMILES: Cc1cnc(NC(=O)CC[C@@H]2CC(=O)[C@@]3(C)CCC4c5cc(I)c(O)c(I)c5CCC4C23)s1]

The compound VII (44 mg, 0.1 mmol) was dissolved into DCM and the mixture was stirred in ice bath. 45 mg (0.2 mmol) of N-iodosuccinimide (NIS) was added and reaction mixture was stirred for 10 min at 0° C. and then reaction was allowed to warm to rt. Water was added after 20 min, the precipitated product was filtered, washed first with water and finally with heptane. Trituration with DCM gave 40% of pure di-iododerivative VIII-6.

MS m/z (TOF ES$^+$): 691 (M+1), 713 (M+Na).

Compound VIII-7

3-((13S,15R)-3-hydroxy-4-iodo-13-methyl-17-oxo-7,8,9,11,12,13,14,15,16,17-decahydro-6H-cyclopenta[a]phenanthren-15-yl)-N-(5-methylthiazol-2-yl)propanamide

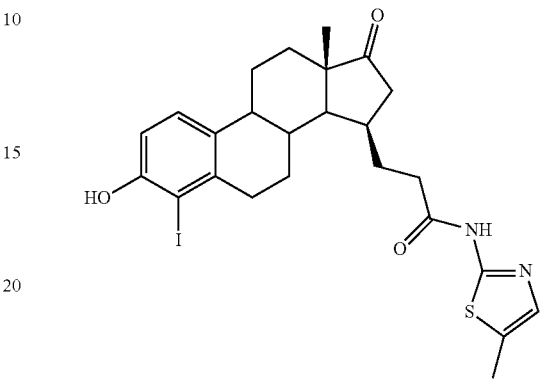

The compound VIII-5 (23 mg, 0.05 mmol) was dissolved into a mixture of 0.5 ml of THF and 0.5 ml of 2N HCl and the solution chilled to 0° C. An ice-cold solution of NaNO$_2$ (5 mg) was added and stirring continued 15 min. Then 30 mg of KI in 50 ul of water was added and the reaction mixture was stirred at 80° C. for 1 h. Water was added into cooled reaction mixture and product was extracted with ethyl acetate, organic phases were washed with water and dried. After evaporation the product was purified by preparative TLC giving 7 mg of pure VIII-7.

$^1$H-NMR (CDCl$_3$): 1.04 (s, 3H), 1.30-2.95 (m, 21H), 6.84 (d, 1H), 7.06 (s, 1H), 7.19 (d, 1H). MS m/z (TOF ES$^+$): 565 (M+H)

Compound VIII-8

3-((13S,15R)-3-hydroxy-2-iodo-13-methyl-17-oxo-7,8,9,11,12,13,14,15,16,17-decahydro-6H-cyclopenta[a]phenanthren-15-yl)-N-(5-methylthiazol-2-yl)propanamide

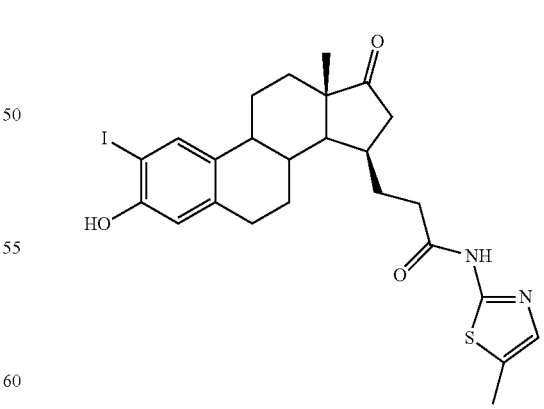

Prepared using the same method as for the compound VIII-7 using the compound VIII-4 as a starting material $^1$H-NMR (CDCl$_3$): 1.05 (s, 3H), 1.28-2.75 (m, 19H), 2.75-2.90 (m, 2H), 6.74 (s, 1H), 7.05 (s, 1H), 7.51 (s, 1H). MS m/z (TOF ES$^+$): 587 (M+Na)

Compounds VIII-9 to VIII-11

The reaction vessel was charged with VII (2.97 g) in DCM (140 ml) and methanol (20 ml). This solution was added dropwise to the solution of tetrabutylammonium tribromide in DCM/MeOH (v/v 1:1, 10 ml) during 30 minutes by stirring at 0-5° C. After 60 minutes the HPLC analysis showed the formation of three products with traces of unreacted starting material; 41% the monobromide VIII-9, 38% monobromide VIII-10 and 16% dibromide VIII-11.

Compound VIII-9

3-((13S,15R)-2-bromo-3-hydroxy-13-methyl-17-oxo-7,8,9,11,12,13,14,15,16,17-decahydro-6H-cyclopenta[a]phenanthren-15-yl)-N-(5-methylthiazol-2-yl)propanamide

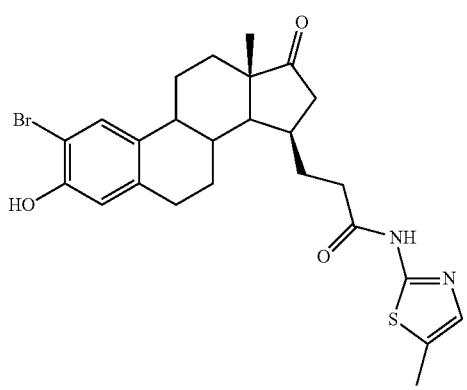 [SMILES: Cc1cnc(NC(=O)CC[C@@H]2CC(=O)[C@@]3(C)CCC4c5cc(Br)c(O)cc5CCC4C23)s1]

$^1$H-NMR (DMSO-d$_6$): 0.96 (s, 3H, -Me), 1.35-2.40 (m, 21H), 2.75 (m, 2H), 6.67 (s, 1H), 7.11 (s, 1H), 7.27 (s, 1H), 9.89 (s, 1H), 11.92 (s, 1H).

Compound VIII-10

3-((13S,15R)-4-bromo-3-hydroxy-13-methyl-17-oxo-7,8,9,11,12,13,14,15,16,17-decahydro-6H-cyclopenta[a]phenanthren-15-yl)-N-(5-methylthiazol-2-yl)propanamide

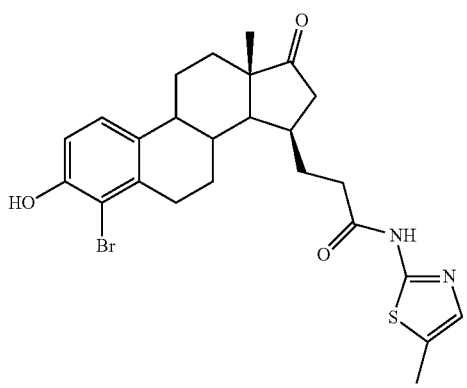 [SMILES: Cc1cnc(NC(=O)CC[C@@H]2CC(=O)[C@@]3(C)CCC4c5ccc(O)c(Br)c5CCC4C23)s1]

$^1$H-NMR (DMSO-d$_6$): 0.95 (s, 3H, -Me), 1.35-2.40 (m, 21H), 2.83 (m, 2H), 6.78 (d, 1H), 7.11 (m, 2H), 7.27 (s, 1H), 9.89 (s, 1H), 11.92 (s, 1H).

Compound VIII-11

3-((13S,15R)-2,4-dibromo-3-hydroxy-13-methyl-17-oxo-7,8,9,11,12,13,14,15,16,17-decahydro-6H-cyclopenta[a]phenanthren-15-yl)-N-(5-methylthiazol-2-yl)propanamide

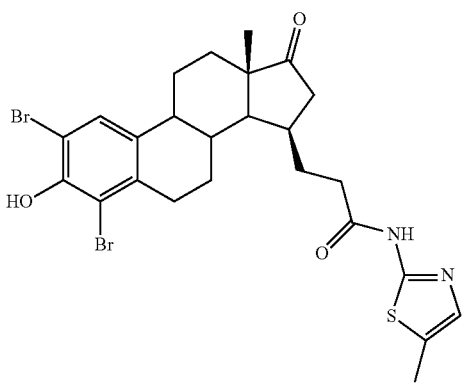 [SMILES: Cc1cnc(NC(=O)CC[C@@H]2CC(=O)[C@@]3(C)CCC4c5cc(Br)c(O)c(Br)c5CCC4C23)s1]

The compound VII (1.0 g, 2.3 mmol) was dissolved in DCM (13 ml), the mixture was cooled to 8° C. and N-bromosuccinimide (NBS) (1.0 g, 5.6 mmol) was added. Reaction mixture was warmed to rt and stirring was continued for 2.5 h. Water was added and precipitated product was filtered, yielding 1.2 g of crystalline dibromide VIII-11.

$^1$H-NMR (DMSO-d$_6$): 0.95 (s, 3H), 1.22-2.32 (m, 19H), 2.79 (m, 2H), 7.12 (s, 1H), 7.40 (s, 1H), 9.55 (s, 1H), 11.92 (s, 1H). MS m/z (TOF ES$^+$): 617/619/621 (M+Na).

Compound VIII-12

3-((13S,15R)-4-chloro-3-hydroxy-13-methyl-17-oxo-7,8,9,11,12,13,14,15,16,17-decahydro-6H-cyclopenta[a]phenanthren-15-yl)-N-(5-methylthiazol-2-yl)propanamide

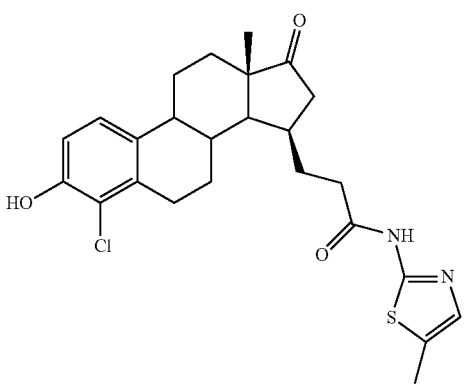 [SMILES: Cc1cnc(NC(=O)CC[C@@H]2CC(=O)[C@@]3(C)CCC4c5ccc(O)c(Cl)c5CCC4C23)s1]

0.5 mmol of the amine compound VIII-5 in 3 ml 2N HCl and 1 ml THF was chilled stirring at 0° C. Solution of 50 mg of NaNO$_2$ in 0.5 ml of water was added dropwise and mixture was stirred for 15 min at this temperature. Then ice bath was removed and preheated solution of 250 mg of CuCl in 5 ml of 2N HCl was added at 80° C. and reaction mixture was kept 2 h at this temperature. After cooling water was added, pH was adjusted to pH 3 and extracted with ethyl acetate, washed with water and brine, dried with Na$_2$SO$_4$ and evaporated. After flash chromatography 85 mg (36%) of the 4-chloro compound VIII-12 was obtained.

¹H-NMR (CDCl₃): 1.05 (s, 3H), 1.30-3.10 (m, 21H), 6.86 (d, 1H), 7.05 (s, 1H), 7.13 (d, 1H). MS m/z (TOF ES⁺): 473/475 (M+H).

Compound VIII-13

3-((13S,15R)-2-chloro-3-hydroxy-13-methyl-17-oxo-7,8,9,11,12,13,14,15,16,17-decahydro-6H-cyclopenta[a]phenanthren-15-yl)-N-(5-methylthiazol-2-yl)propanamide

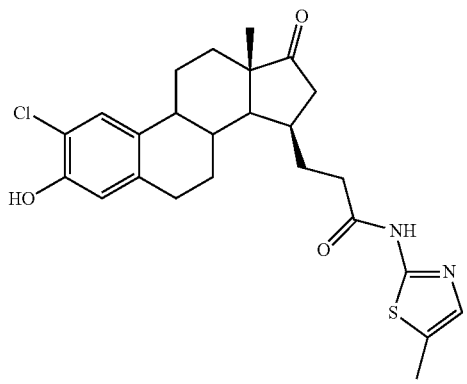 [SMILES: Cc1cnc(NC(=O)CC[C@@H]2CC(=O)[C@@]3(C)CCC4c5cc(Cl)c(O)cc5CCC4C23)s1]

Prepared from the compound VIII-4 by the same method as for the compound VIII-12 in 0.4 mmol scale giving the desired product in 28% yield.

¹H-NMR (CDCl₃+MeOH-d₄): 1.06 (s, 3H), 1.20-2.65 (m, 19H), 2.75-3.05 (m, 2H), 6.70 (s, 1H), 7.03 (s, 1H), 7.18 (s, 1H). MS m/z (TOF ES+): 495/497 (M+Na).

Compound VIII-14

3-((13S,15R)-2,4-dichloro-3-hydroxy-13-methyl-17-oxo-7,8,9,11,12,13,14,15,16,17-decahydro-6H-cyclopenta[a]phenanthren-15-yl)-N-(5-methylthiazol-2-yl)propanamide

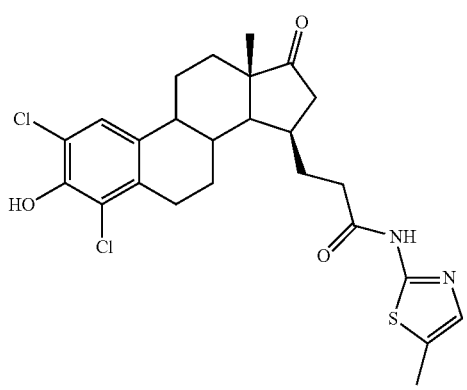 [SMILES: Cc1cnc(NC(=O)CC[C@@H]2CC(=O)[C@@]3(C)CCC4c5cc(Cl)c(O)c(Cl)c5CCC4C23)s1]

The reaction vessel was charged with the compound VII (4 g) and dry DCM (150 ml) at 0° C. under argon atmosphere. Diethylamine (1.4 ml, 150 mol-%) was added dropwise, followed by sulfuryl chloride (1.1 ml, 150 mol-%). After 30 minutes at 0° C. water was added to the reaction mixture. The organic phase was separated, dried over Na₂SO₄ and the solvent was evaporated. The residue was purified by column chromatography using DCM/acetone 98:2 as an eluent.

¹H-NMR (DMSO-d₆): 0.96 (s, 3H), 1.35-2.40 (m, 21H), 2.80 (m, 2H), 7.12 (s, 1H), 7.23 (s, 1H), 9.75 (s, 1H), 11.92 (s, 1H).

Fluorides

Fluorides were prepared from the corresponding amines via thermolysis of their diazonium fluoborate salts in 0.05-0.3 mmol scale.

Compound VIII-15

3-((13S,15R)-4-fluoro-3-hydroxy-13-methyl-17-oxo-7,8,9,11,12,13,14,15,16,17-decahydro-6H-cyclopenta[a]phenanthren-15-yl)-N-(5-methylthiazol-2-yl)propanamide

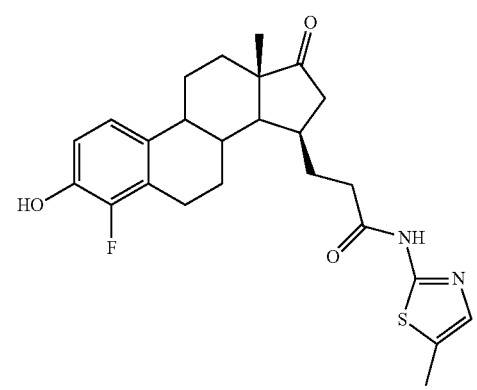

A mixture of the compound VIII-5 (91 mg, 0.2 mmol), ethanol (2 ml) and 48% tetrafluoroboric acid (0.5 ml) in water was chilled to 0° C. stirring in ice bath. A solution of NaNO₂ (20 mg) in 0.2 ml of water was added and stirring continued for 1 h at 0° C. Fluoroborate salt was precipitated by adding diethyl ether until there was no more salt coming out the solution. Ether was decanted and precipitated material was washed twice with diethyl ether and dried in vacuum. The dried fluoroborate salt was heated in a flask at 120-130° C. in a good hood for a couple of hours. The remaining material was treated with DCM and filtered. The solvent was evaporated and the product was purified by flash chromatography affording 22 mg of the 4-fluoride VIII-15.

¹H-NMR (CDCl₃): 1.04 (s, 3H), 1.30-3.05 (m, 21H), 6.75-6.98 (m, 2H), 7.05 (br s, 1H). MS m/z (TOF ES+): 479 (M+Na).

Compound VIII-16

3-((13S,15R)-2-fluoro-3-hydroxy-13-methyl-17-oxo-7,8,9,11,12,13,14,15,16,17-decahydro-6H-cyclopenta[a]phenanthren-15-yl)-N-(5-methylthiazol-2-yl)propanamide

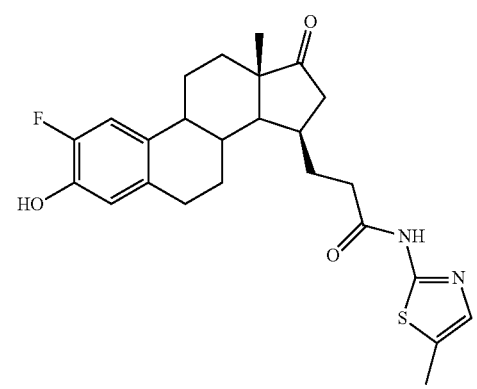 [SMILES: Cc1cnc(NC(=O)CC[C@@H]2CC(=O)[C@@]3(C)CCC4c5cc(F)c(O)cc5CCC4C23)s1]

Prepared from the compound VIII-4 using the method used for the compound VIII-15. The catechol VIII-17 was isolated as a by-product.

¹H-NMR (CDCl₃): 1.05 (s, 3H), 1.30-2.70 (m, 19H), 2.75-2.90 (m, 2H), 6.73 (d, J=10 Hz, 1H), 6.97 (d, J=14 Hz, 1H), 7.05 (br s, 1H). MS m/z (TOF ES⁺): 479 (M+Na).

Compound VIII-17

3-((13S,15R)-2,3-dihydroxy-13-methyl-17-oxo-7,8,9,11,12,13,14,15,16,17-decahydro-6H-cyclopenta[a]phenanthren-15-yl)-N-(5-methylthiazol-2-yl)propanamide

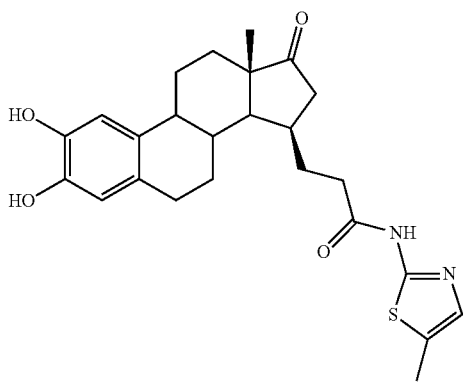 [SMILES: Cc1cnc(NC(=O)CC[C@@H]2CC(=O)[C@@]3(C)CCC4c5cc(O)c(O)cc5CCC4C23)s1]

¹H-NMR (CDCl₃+MeOH-d₄): 1.07 (s, 3H), 1.20-2.70 (m, 21H), 7.07 (s, 1H), 7.16 (s, 1H), 7.31 (s, 1H). MS m/z (TOF ES⁺): 477 (M+Na).

Compound VIII-18

3-{(13S,15R)-2-Bromo-4-fluoro-3-hydroxy-13-methyl-17-oxo-7,8,9,11,12,13,14,15,16,17-decahydro-6H-cyclopenta[a]phenanthren-15-yl}-N-(5-methylthiazol-2-yl)propanamide

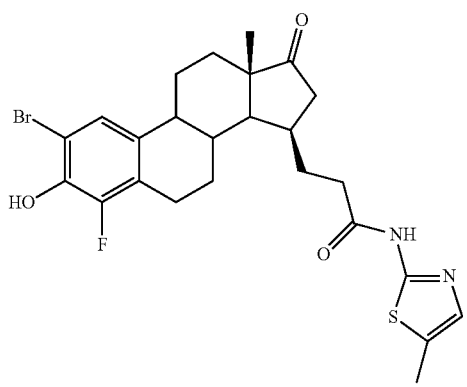 [SMILES: Cc1cnc(NC(=O)CC[C@@H]2CC(=O)[C@@]3(C)CCC4c5cc(Br)c(O)c(F)c5CCC4C23)s1]

The starting material, the compound VIII-15 was brominated by using NBS (120 mol-%) in DCM at 0° C.

¹H-NMR (CDCl₃): 1.05 (s, 3H), 1.26-2.99 (m, 21H), 7.05 (s, 1H), 7.12 (s, 1H). MS m/z (TOF ES+): 557/559 (M+Na).

Compound VIII-19

3-{(13S,15R)-4-Bromo-2-fluoro-3-hydroxy-13-methyl-17-oxo-7,8,9,11,12,13,14,15,16,17-decahydro-6H-cyclopenta[a]phenanthren-15-yl}-N-(5-methylthiazol-2-yl)propanamide

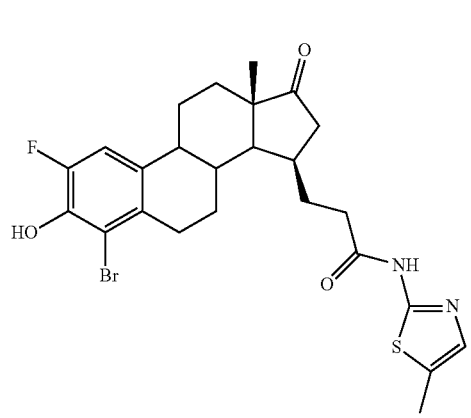 [SMILES: Cc1cnc(NC(=O)CC[C@@H]2CC(=O)[C@@]3(C)CCC4c5cc(F)c(O)c(Br)c5CCC4C23)s1]

The starting material, the compound VIII-16 was brominated by using NBS (120 mol-%) in DCM at 0° C.

¹H-NMR (CDCl₃): 1.04 (s, 3H), 1.36-2.97 (m, 21H), 6.99 (d, 1H), 7.05 (br s, 1H). MS m/z (TOF ES⁺): 535/537 (M+H).

Further Aromatic Modifications of Fluorides

Compound VIII-20

3-((13S,15R)-4-fluoro-3-hydroxy-13-methyl-2-nitro-17-oxo-7,8,9,11,12,13,14,15,16,17-decahydro-6H-cyclopenta[a]phenanthren-15-yl)-N-(5-methylthiazol-2-yl)propanamide

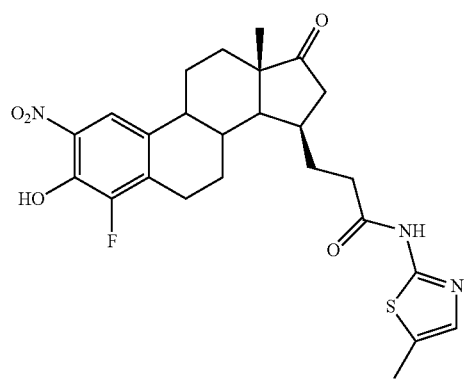 [SMILES: Cc1cnc(NC(=O)CC[C@@H]2CC(=O)[C@@]3(C)CCC4c5cc([N+](=O)[O-])c(O)c(F)c5CCC4C23)s1]

150 mg of the compound VIII-15 was added into a suspension of 55 mg of silica and 55 μl water in a solution of 1.4 ml THF and 1.4 ml DCM and stirred at rt. 340 mg of Silica-sulfuric acid (prepared by adding dropwise 8.0 g of sulphuric acid to 10 g of silica gel, and stirred for 30 minutes at rt) was added, followed by 32 mg of sodium nitrite. Stirring was continued at rt and reaction was monitored by TLC and HPLC. After the reaction was completed silica was filtered off, washed with DCM and finally with DCM-methanol. Solvents were evaporated and the product was purified by flash chromatography giving 40 mg of the compound VIII-20.

¹H-NMR (CDCl₃): 1.07 (s, 3H), 1.30-3.20 (m, 21H), 7.05 (s, 1H), 7.82 (s, 1H). MS m/z (TOF ES+): 502 (M+H).

Compound VIII-21

3-((13S,15R)-2-amino-4-fluoro-3-hydroxy-13-methyl-17-oxo-7,8,9,11,12,13,14,15,16,17-decahydro-6H-cyclopenta[a]phenanthren-15-yl)-N-(5-methylthiazol-2-yl)propanamide

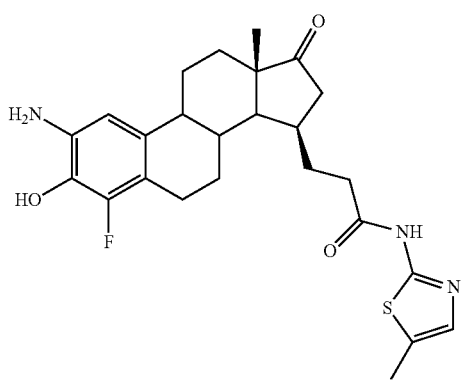

Prepared by hydrogenation of the compound VIII-20 in ethanol con-taining 20% of THF with Pd/C at 25-30° C.

¹H-NMR (CDCl₃): 1.06 (s, 3H), 1.30-2.50 (m, 21H), 6.48 (s, 1H), 6.58 (s, 1H). MS m/z (TOF ES+): 494 (M+Na).

Compound VIII-22

3-((13S,15R)-4-chloro-3-hydroxy-13-methyl-2-nitro-17-oxo-7,8,9,11,12,13,14,15,16,17-decahydro-6H-cyclopenta[a]phenanthren-15-yl)-N-(5-methylthiazol-2-yl)propanamide

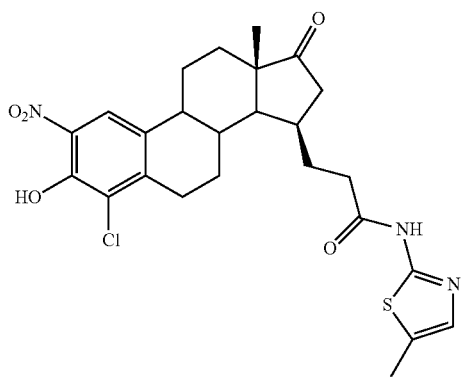 [SMILES: Cc1cnc(NC(=O)CC[C@@H]2CC(=O)[C@@]3(C)CCC4c5cc([N+](=O)[O-])c(O)c(Cl)c5CCC4C23)s1]

Prepared from the compound VIII-12 as described for the compound VIII-20 above.

¹H-NMR (CDCl₃): 1.07 (s, 3H), 1.35-3.20 (m, 21H), 7.05 (s, 1H), 7.99 (s, 1H). MS m/z (TOF ES+): 518/520 (M+H).

Compound VIII-23

3-((13S,15R)-2-amino-4-chloro-3-hydroxy-13-methyl-17-oxo-7,8,9,11,12,13,14,15,16,17-decahydro-6H-cyclopenta[a]phenanthren-15-yl)-N-(5-methylthiazol-2-yl)propanamide

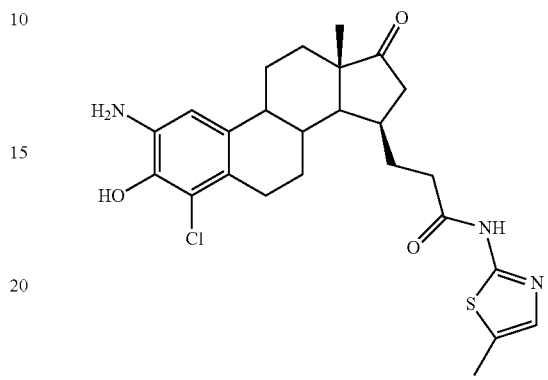

Prepared by hydrogenation of the compound VIII-22 in ethanol containing 20% of THF with Pd/C catalyst at 25-30° C.

¹H-NMR (CDCl₃+MeOH-d₄): 1.05 (s, 3H), 1.35-3.00 (m, 21H), 6.64 (s, 1H), 7.04 (s, 1H). MS m/z (TOF ES+): 510/512 (M+Na).

Compound VIII-24

3-((13S,15R)-2-cyano-3-hydroxy-13-methyl-17-oxo-7,8,9,11,12,13,14,15,16,17-decahydro-6H-cyclopenta[a]phenanthren-15-yl)-N-(5-methylthiazol-2-yl)propanamide

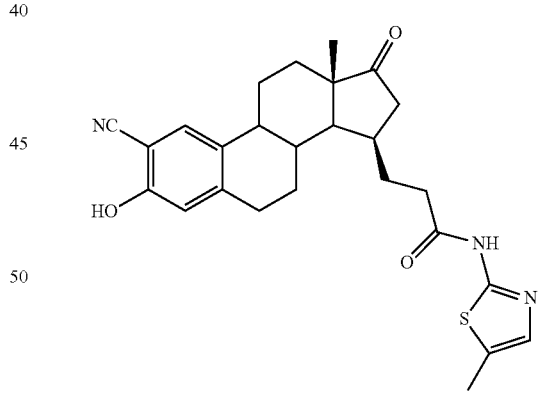

The C-2 bromide VIII-9 (50 mg, 100 mol-%) and copper (I)cyanide (230 mol-%) were dissolved in dry DMF (5 ml) and refluxed under nitrogen for six hours. The reaction mixture was cooled and FeCl₃ (5000 mol-%) in conc. HCl (500 µl) was added, and stirred at 55-60° C. for 30 minutes. The reaction mixture was cooled, diluted with water. The product was extracted with EtOAc, washed with water, sat. NaHCO₃-solution until pH was 8, and finally with brine. Purification by chromatography.

¹H-NMR (CDCl3+MeOH-d₄): 1.05 (s, 3H), 1.40-2.65 (m, 19H), 2.89 (m, 2H), 6.70 (s, 1H), 7.06 (s, 1H), 7.36 (s, 1H).

Compound VIII-25

3-((13S,15R)-4-cyano-3-hydroxy-13-methyl-17-oxo-7,8,9,11,12,13,14,15,16,17-decahydro-6H-cyclopenta[a]phenanthren-15-yl)-N-(5-methylthiazol-2-yl)propanamide

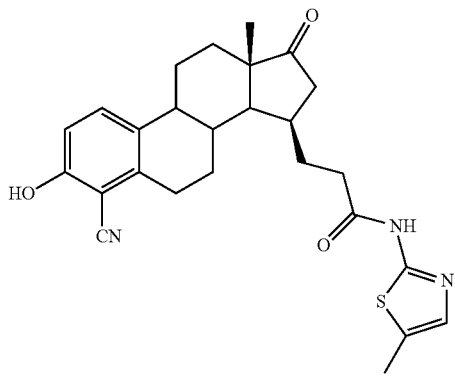

Prepared according to method used for the compound VIII-24 using the C-4 bromide VIII-10 as a starting material.
$^1$H-NMR (CDCl3+MeOH-d$_4$): 1.03 (s, 3H), 1.22-2.56 (m, 19H), 3.05 (m, 2H), 6.76 (d, 1H), 7.06 (s, 1H), 7.31 (s, 1H). MS m/z (TOF ES$^+$): 464 (M+1).

Compound VIII-26

(13S,15R)-2,4-dibromo-13-methyl-15-(3-((5-methylthiazol-2-yl)-amino)-3-oxopropyl)-17-oxo-7,8,9,11,12,13,14,15,16,17-decahydro-6H-cyclopenta[a]phenanthren-3-yl dihydrogen phosphate

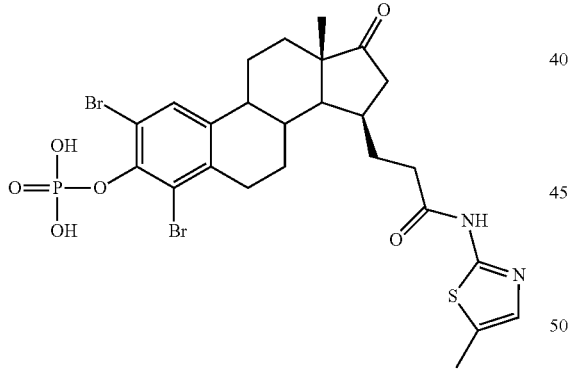

VIII-11 (150 mg, 0.25 mmol, 100 mol-%) was dissolved in dry THF (3 ml) and pyridine (1.5 ml), DMAP (31 mg, 0.25 mmol, 100 mol-%) was added. Phosphorus oxychloride (70 µl, 0.76 mmol, 300 mol-%) was added dropwise under nitrogen. The mixture was stirred at rt for 5.5 h. The mixture was cooled with an ice bath, water (2 ml) was added and the mixture was stirred at rt for 1 h and left standing overnight. The solvents were evaporated, water (3 ml) was added and the mixture was left to precipitate overnight. The precipitate was filtered and washed with water, 2N HCl and water. The precipitate was then co-evaporated with toluene and ethanol affording 115 mg of the product.
$^1$H-NMR (DMSO-d$_6$): 0.96 (s, 3H), 1.10-2.90 (m, 23H), 7.11 (s, 1H), 7.51 (s, 1H), 11.91 (br s, 1H). $^{31}$P-NMR (DMSO-d6): -7.38. MS m/z (TOF ES$^+$): 677 (M+1).

Compound VIII-27

(13S,15R)-13-methyl-15-(3-((5-methylthiazol-2-yl)amino)-3-oxopropyl)-4-nitro-17-oxo-7,8,9,11,12,13,14,15,16,17-decahydro-6H-cyclopenta[a]-phenanthren-3-yl dihydrogen phosphate

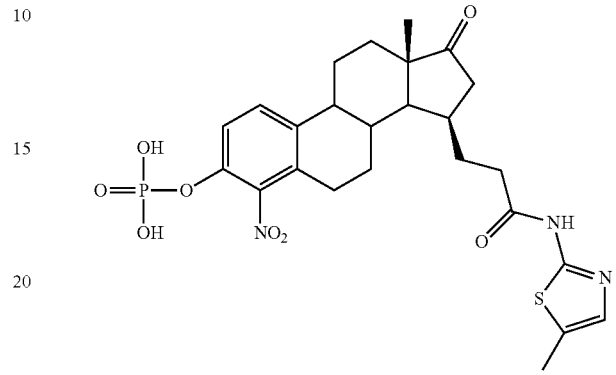

VIII-4 (150 mg, 0.342 mmol, 100 mol-%) was dissolved in dry THF (2 ml) and pyridine (1 ml), DMAP (42 mg, 0.342 mmol, 100 mol-%) was added. Phosphorus oxychloride (96 µl, 1.026 mmol, 300 mol-%) was added dropwise under nitrogen and the mixture was stirred in rt for 3.5 h. The mixture was cooled with an ice bath, cold water (2 ml) was added, stirred for 1 h and the solvents were evaporated. Water (3 ml) was added and the mixture was triturated for few 25 minutes. The precipitate was filtered and washed with water, 2N HCl and water. Amount of the product 119 mg, yield 62%.
$^1$H-NMR (DMSO-d$_6$): 0.97 (s, 3H), 1.10-3.00 (m, 21H), 7.1 (s, 1H), 7.40-7.47 (m, 2H), 11.90 (br s, 1H). $^{31}$P-NMR (DMSO-d6): -6.70.

Compound VIII-28

(13S,15R)-4-bromo-13-methyl-15-(3-((5-methylthiazol-2-yl)amino)-3-oxopropyl)-17-oxo-7,8,9,11,12,13,14,15,16,17-decahydro-6H-cyclopenta[a]-phenanthren-3-yl dihydrogen phosphate

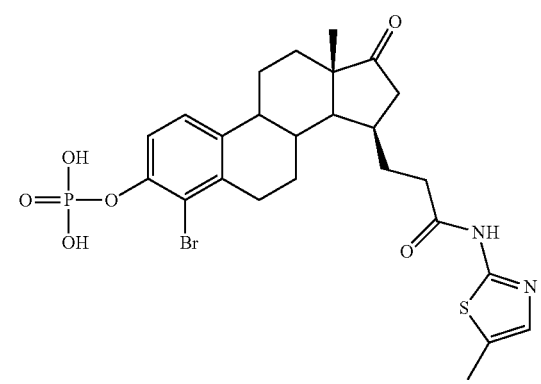 [SMILES: Cc1cnc(NC(=O)CC[C@@H]2CC(=O)[C@@]3(C)CCC4c5ccc(OP(=O)(O)O)c(Br)c5CCC4C23)s1]

VIII-10 (120 mg, 0.23 mmol, 100 mol-%) was dissolved in dry THF (2 ml) and pyridine (1 ml), DMAP (28 mg, 0.23 mmol, 100 mol-%) was added. Phosphorus oxychloride (65 µl, 0.70 mmol, 300 mol-%) was added dropwise under nitrogen and the mixture was stirred in rt for 2.5 h. The mixture was cooled with an ice bath, cold water (2 ml) was added, stirred for 1 h and the solvents were evaporated. Water (3 ml) was added and the mixture was left to precipitate overnight. The precipitate was filtered and washed with water, 2N HCl and water. The precipitate was co-evaporated with toluene and ethanol, affording 109 mg of the crude product. Yield 79%.

$^1$H-NMR (DMSO-$d_6$): 0.97 (s, 3H), 1.10-3.00 (m, 21H), 6.90-7.50 (m, 3H), 11.90 (br s, 1H). $^{31}$P-NMR (DMSO-d6): −6.72.

Compound VIII-29

(13S,15R)-2,4-dibromo-13-methyl-15-(3-((5-methyl-thiazol-2-yl)-amino)-3-oxopropyl)-17-oxo-7,8,9,11,12,13,14,15,16,17-decahydro-6H-cyclopenta[a]phenanthren-3-yl acetate

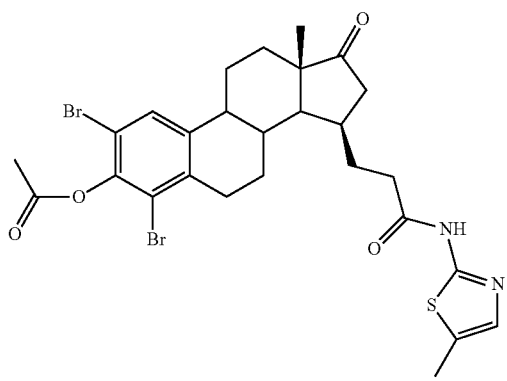 [SMILES: CC(=O)Oc1c(Br)cc2c(c1Br)CCC1C2CC[C@]2(C)C(=O)C[C@@H](CCC(=O)Nc3ncc(C)s3)C12]

VIII-11 (100 mg, 0.17 mmol, 100 mol-%) and DMAP (6 mg, 0.050 mmol, 30 mol-%) were suspended in dry DCM (3 ml). Pyridine (165 µl, 2.01 mmol, 1200 mol-%) and acetic anhydride (79 µl, 0.84 mmol, 500 mol-%) were added under nitrogen and the mixture was stirred overnight at rt. The mixture was diluted with DCM (3 ml) and washed with water, 2N HCl, water and brine. Drying with Na$_2$SO$_4$ and evaporating the solvent afforded 88 mg of the crude product. Yield 82%.

$^1$H-NMR (DMSO-$d_6$): 0.96 (s, 3H), 1.10-2.90 (m, 21H), 2.37 (s, 3H), 7.11 (s, 1H), 7.61 (s, 1H), 11.91 (brs, 1H).

Synthesis of C-17 Methyloximes

General Method for the Preparation of C-17 Methyl Oximes:

Ketone (0.3 mmol) was dissolved in a mixture of ethanol (3 ml) and THF (2 ml) under nitrogen atmosphere. Pyridine (1.5 mmol) and methoxylamine hydrochloride (0.9 mmol) were added to this solution. The reaction mixture was refluxed for 1-2 h. Solvents were evaporated. Water was added and the product was either filtered or extracted with ethyl acetate, washed with dilute hydrochloric acid and finally with water. Oximes were purified further by flash-chromatography if required.

Compound VIV-1

3-{(13S,15R)-3-Hydroxy-17-[(E)-methoxyimino]-13-methyl-7,8,9,11,12,13,14,15,16,17-decahydro-6H-cyclopenta[a]phenanthren-15-yl}-N-(5-methyl-thiazol-2-yl)propanamide

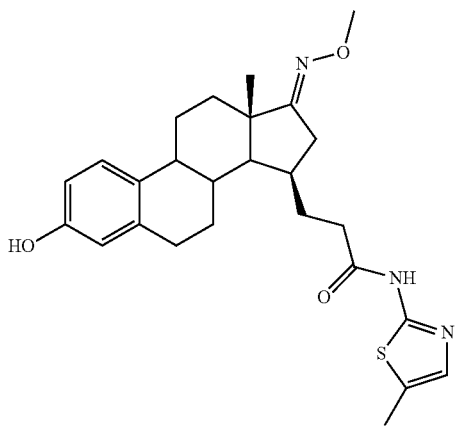 [SMILES: CO/N=C1\C[C@@H](CCC(=O)Nc2ncc(C)s2)C2C3CCc4cc(O)ccc4C3CC[C@]12C]

To a suspension of VII (700 mg, 100 mol-%) and EtOH (abs.) (30 ml) was added methoxyl amine hydrochloride (670 mg, 500 mol-%) followed by pyridine (1.52 g, 1200 mol-%). The resulting solution was refluxed 3 hours and the solvent was evaporated. Water was added to the residue. The aqueous layer was extracted with EtOAc. The combined organic layers were washed with water and brine, dried over Na$_2$SO$_4$, filtered and evaporated. The crude product was triturated with heptane. The yield of the product 73 was 700 mg (94%).

$^1$H-NMR (CDCl$_3$): 1.09 (s, 3H), 1.15-2.90 (m, 21H), 3.84 (s, 3H), 6.57-6.66 (m, 2H), 7.00-7.15 (m, 2H). MS m/z (TOF ES$^+$): 490 (M+Na).

Compound VIV-2

3-{(13S,15R)-3-Hydroxy-17-[(E)-methoxyimino]-13-methyl-2-nitro-7,8,9,11,12,13,14,15,16,17-deca-hydro-6H-cyclopenta[a]phenanthren-15-yl}-N-(5-methylthiazol-2-yl)propanamide

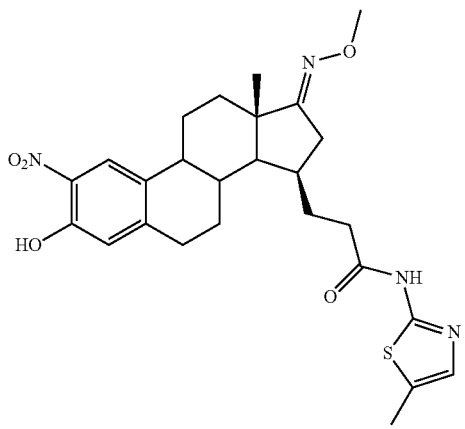 [SMILES: CO/N=C1\C[C@@H](CCC(=O)Nc2ncc(C)s2)C2C3CCc4cc(O)c([N+](=O)[O-])cc4C3CC[C@]12C]

Prepared by the method as described for the compound VIV-1 using the compound VIII-1 as a starting material.

¹H-NMR (CDCl₃): 1.11 (s, 3H), 1.40-3.05 (m, 21H), 3.85 (s, 3H), 6.87 (s, 1H), 7.07 (s, 1H), 7.98 (s, 1H) 10.57 (br s, 1H), 11.91 (br s, 1H). MS m/z (TOF ES⁺): 513 (M+H).

Compound VIV-3

3-{(13S,15R)-2-Amino-3-hydroxy-17-[(E)-methoxyimino]-13-methyl-7,8,9,11,12,13,14,15,16,17-decahydro-6H-cyclopenta[a]phenanthren-15-yl}-N-(5-methylthiazol-2-yl)propanamide

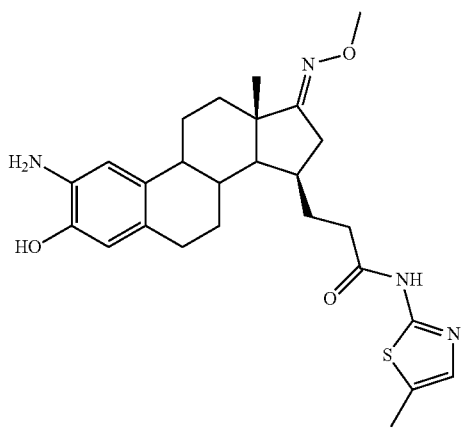

Prepared by the method as described for the compound VIV-1 using the compound VIII-4 as a starting material.

¹H-NMR (CDCl₃): 1.04 (s, 3H), 1.25-2.90 (m, 21H), 3.84 (s, 3H), 6.47 (s, 1H), 6.68 (s, 1H), 7.05 (s, 1H). MS m/z (TOF ES⁺): 505 (M+Na).

Compound VIV-4

3-{(13S,15R)-3-Hydroxy-17-[(E)-methoxyimino]-13-methyl-4-nitro-7,8,9,11,12,13,14,15,16,17-decahydro-6H-cyclopenta[a]phenanthren-15-yl}-N-(5-methylthiazol-2-yl)propanamide

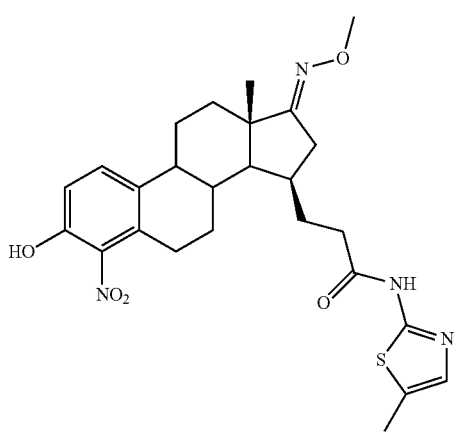 [SMILES: CO/N=C1\C[C@@H](CCC(=O)Nc2ncc(C)s2)C2C3CCc4c(ccc(O)c4N)C3CC[C@]12C]

Prepared by the method as described for the compound VIV-1 using the compound VIII-2 as a starting material.

¹H-NMR (CDCl₃): 1.12 (s, 3H), 1.20-3.35 (m, 21H), 6.96 (d, 1H), 7.07 (s, 1H), 7.48 (d, 1H). MS m/z (TOF ES⁺): 535 (M+Na).

Compound VIV-5

3-{(13S,15R)-4-Amino-3-hydroxy-17-[(E)-methoxyimino]-13-methyl-7,8,9,11,12,13,14,15,16,17-decahydro-6H-cyclopenta[a]phenanthren-15-yl}-N-(5-methylthiazol-2-yl)propanamide

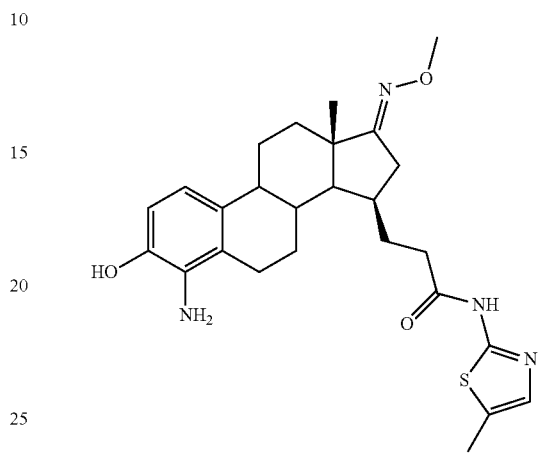

Prepared by the method as described for the compound VIV-1 using the compound VIII-5 as a starting material.

¹H-NMR (CDCl₃): 1.04 (s, 3H), 1.20-2.95 (m, 21H), 3.84 (s, 3H), 6.58 (AB, 2H), 7.08 (s, 1H). MS m/z (TOF ES⁺): 505 (M+Na).

Compound VIV-6

3-{(13S,15R)-3-Hydroxy-2-iodo-17-[(E)-methoxyimino]-13-methyl-7,8,9,11,12,13,14,15,16,17-decahydro-6H-cyclopenta[a]phenanthren-15-yl}-N-(5-methylthiazol-2-yl)propanamide

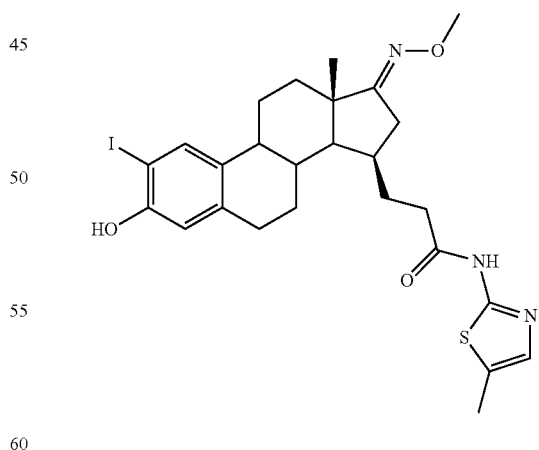

Prepared by the method as described for the compound VIV-1 using the compound VIII-18 as a starting material.

¹H-NMR (CDCl₃): 1.09 (s, 3H), 1.20-2.90 (m, 21H), 3.84 (s, 3H), 6.72 (s, 1H), 7.07 (s, 1H), 7.51 (s, 1H). MS m/z (TOF ES⁺): 616 (M+Na).

Compound VIV-7

3-{(13S,15R)-3-Hydroxy-4-iodo-17-[(E)-methoxyimino]-13-methyl-7,8,9,11,12,13,14,15,16,17-decahydro-6H-cyclopenta[a]phenanthren-15-yl}-N-(5-methylthiazol-2-yl)propanamide

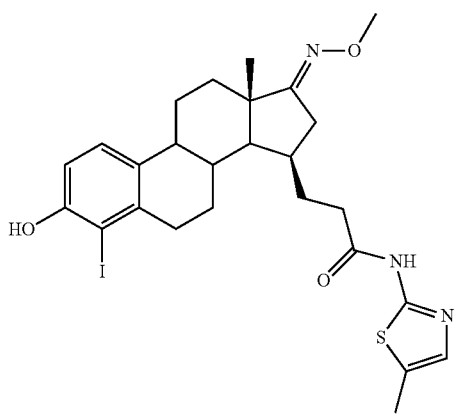 [SMILES: CO/N=C1\C[C@@H](CCC(=O)Nc2ncc(C)s2)C2C3CCc4c(ccc(O)c4I)C3CC[C@]12C]

Prepared by the method as described for the compound VIV-1 using the compound VIII-7 as a starting material.

$^1$H-NMR (CDCl$_3$): 1.09 (s, 3H), 1.30-2.95 (m, 21H), 3.85 (s, 3H), 6.83 (d, 1H), 7.08 (s, 1H), 7.19 (d, 1H). MS m/z (TOF ES$^+$): 616 (M+Na).

Compound VIV-8

3-{(13S,15R)-3-Hydroxy-2,4-diiodo-17-[(E)-methoxyimino]-13-methyl-7,8,9,11,12,13,14,15,16,17-decahydro-6H-cyclopenta[a]phenanthren-15-yl}-N-(5-methylthiazol-2-yl)propanamide

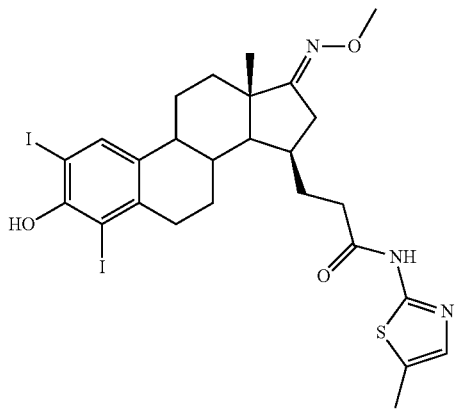 [SMILES: CO/N=C1\C[C@@H](CCC(=O)Nc2ncc(C)s2)C2C3CCc4c(cc(I)c(O)c4I)C3CC[C@]12C]

Prepared by the method as described for the compound VIV-1 using the compound VIII-6 as a starting material in 45% yield.

$^1$H-NMR (CDCl$_3$): 1.09 (s, 3H), 1.23-2.96 (m, 21H), 3.85 (s, 3H), 7.61 (s, 1H), 7.08 (s, 1H). MS m/z (TOF ES$^+$): 720 (M+1).

Compound VIV-9

3-{(13S,15R)-2-Bromo-3-hydroxy-17-[(E)-methoxyimino]-13-methyl-7,8,9,11,12,13,14,15,16,17-decahydro-6H-cyclopenta[a]phenanthren-15-yl}-N-(5-methylthiazol-2-yl)-propanamide

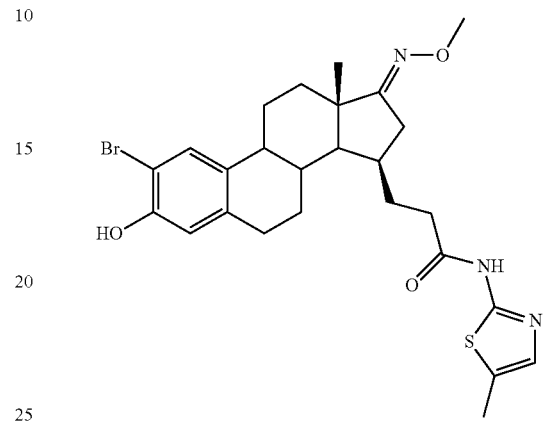

Prepared by the method as described for the compound VIV-1 using the C-2 monobromide VIII-9 as a starting material.

$^1$H-NMR (DMSO-d$_6$): 1.03 (s, 3H), 1.2-3.0 (m, 18H), 2.33 (s, 3H), 3.73 (s, 3H), 6.65 (s, 1H), 7.11 (s, 1H), 7.27 (d, 1H), 9.86 (s, 1H), 11.91 (s, 1H). MS m/z (TOF ES$^+$): 546/548.

Compound VIV-10

3-{(13S,15R)-4-Bromo-3-hydroxy-17-[(E)-methoxyimino]-13-methyl-7,8,9,11,12,13,14,15,16,17-decahydro-6H-cyclopenta[a]phenanthren-15-yl}-N-(5-methylthiazol-2-yl)propanamide

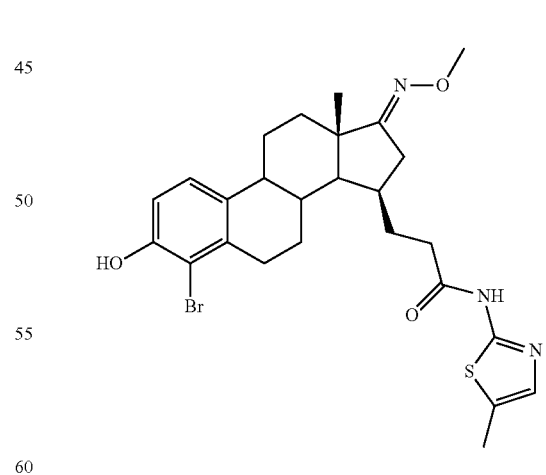

Prepared by the method as described for the compound VIV-1 using the C-4 monobromide VIII-10 as a starting material.

$^1$H-NMR (DMSO-d$_6$): 1.02 (s, 3H), 1.2-2.9 (m, 18H), 2.33 (s, 3H), 3.73 (s, 3H), 6.76 (m, 1H), 7.12 (m, 2H), 9.89 (s, 1H), 11.92 (s, 1H). MS m/z (TOF ES$^+$): 568/570 (M+Na).

Compound VIV-11

3-{(13S,15R)-2,4-Dibromo-3-hydroxy-17-[(E)-methoxyimino]-13-methyl-7,8,9,11,12,13,14,15,16,17-decahydro-6H-cyclopenta[a]phenanthren-15-yl}-N-(5-methylthiazol-2-yl)propanamide

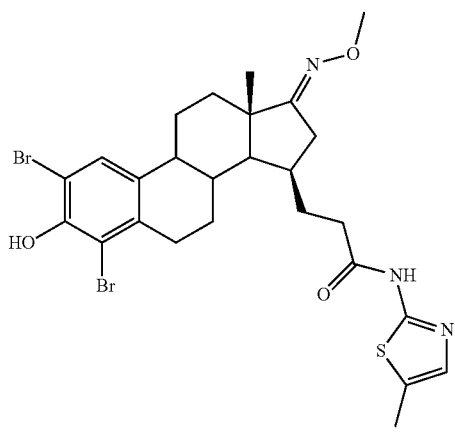 [SMILES: CO/N=C1\C[C@@H](CCC(=O)Nc2ncc(C)s2)C2C3CCc4c(cc(Br)c(O)c4Br)C3CC[C@]12C]

Prepared by the method as described for the compound VIV-1 using the C-2,4-dibromide VIII-11 as a starting material.

$^1$H-NMR (DMSO-d$_6$): 1.01 (s, 3H), 1.10-2.90 (m, 21H), 3.72 (s, 3H), 7.11 (s, 1H), 7.40 (s, 1H), 9.54 (s, 1H), 11.91 (s, 1H). MS m/z (TOF ES$^+$): 648 (M+Na).

Compound VIV-12

3-{(13S,15R)-2-Chloro-3-hydroxy-17-[(E)-methoxyimino]-13-methyl-7,8,9,11,12,13,14,15,16,17-decahydro-6H-cyclopenta[a]phenanthren-15-yl}-N-(5-methylthiazol-2-yl)propanamide

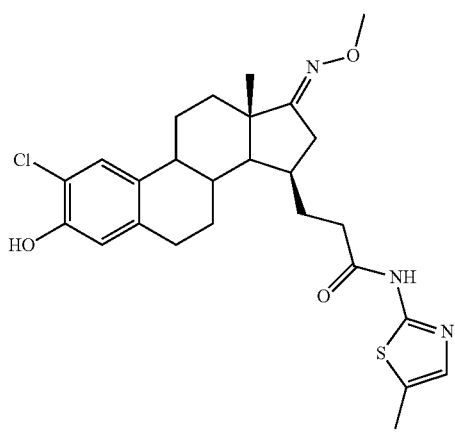 [SMILES: CO/N=C1\C[C@@H](CCC(=O)Nc2ncc(C)s2)C2C3CCc4cc(O)c(Cl)cc4C3CC[C@]12C]

Prepared by the method as described for the compound VIV-1 using the compound VIII-13 as a starting material.

$^1$H-NMR (CDCl$_3$): 1.09 (s, 3H), 1.25-2.92 (m, 21H), 3.84 (s, 3H), 6.73 (s, 1H), 7.07 (s, 1H), 7.19 (s, 1H). MS m/z (TOF ES$^+$): 524/526 (M+Na).

Compound VIV-13

3-{(13S,15R)-4-Chloro-3-hydroxy-17-[(E)-methoxyimino]-13-methyl-7,8,9,11,12,13,14,15,16,17-decahydro-6H-cyclopenta[a]phenanthren-15-yl}-N-(5-methylthiazol-2-yl)propanamide

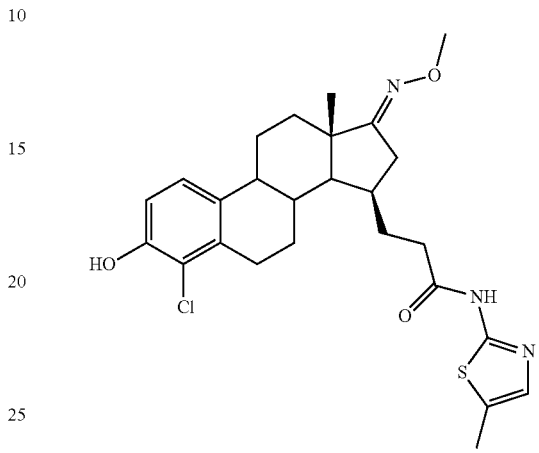

Prepared by the method as described for the compound VIV-1 using the compound VIII-12 as a starting material.

$^1$H-NMR (CDCl$_3$): 1.09 (s, 3H), 1.25-3.05 (m, 21H), 3.84 (s, 3H) 6.84 (d, 1H), 7.07 (s, 1H), 7.12 (d, 1H). MS m/z (TOF ES$^+$): 524/526 (M+Na).

Compound VIV-14

3-{(13S,15R)-2,4-Dichloro-3-hydroxy-17-[(E)-methoxyimino]-13-methyl-7,8,9,11,12,13,14,15,16,17-decahydro-6H-cyclopenta[a]phenanthren-15-yl}-N-(5-methylthiazol-2-yl)propanamide

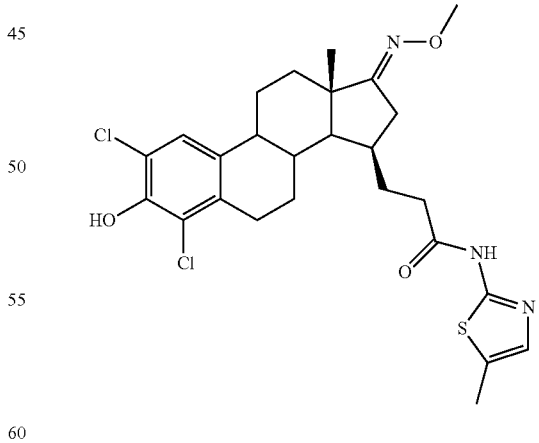

Prepared by the method as described for the compound VIV-1 using the C-2,4 dichloride VIII-14 as a starting material.

$^1$H-NMR (CDCl$_3$): 1.10 (s, 3H), 1.4-3.0 (m, 18H), 2.42 (s, 3H), 3.85 (s, 3H), 7.07 (s, 1H), 7.21 (s, 1H). MS m/z (TOF ES$^+$): 558/560 (M+Na).

Compound VIV-15

3-{(13S,15R)-2-Fluoro-3-hydroxy-17-[(E)-methoxy-imino]-13-methyl-7,8,9,11,12,13,14,15,16,17-deca-hydro-6H-cyclopenta[a]phenanthren-15-yl}-N-(5-methylthiazol-2-yl)propanamide

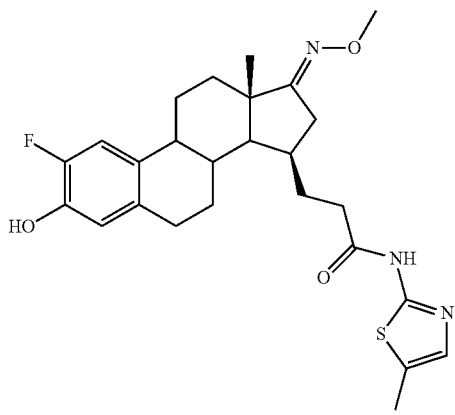 [SMILES: CO/N=C1\C[C@@H](CCC(=O)Nc2ncc(C)s2)C2C3CCc4cc(O)c(F)cc4C3CC[C@]12C]

Prepared by the method as described for the compound VIV-1 using the compound VIII-16 as a starting material.

$^1$H-NMR (CDCl$_3$+MeOH-d$_4$): 1.10 (s, 3H), 1.25-3.0 (m, 21H), 3.84 (s, 3H), 6.66 (d, J=10 Hz, 1H), 6.94 (d, J=12 Hz, 1H), 7.03 (br s, 1H). MS m/z (TOF ES$^+$): 508 (M+Na).

Compound VIV-16

3-{(13S,15R)-4-Fluoro-3-hydroxy-17-[(E)-methoxy-imino]-13-methyl-7,8,9,11,12,13,14,15,16,17-deca-hydro-6H-cyclopenta[a]phenanthren-15-yl}-N-(5-methylthiazol-2-yl)propanamide

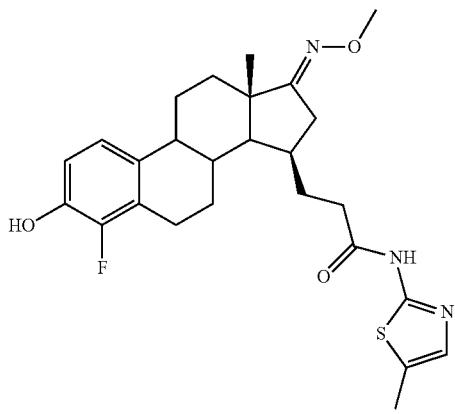

Prepared by the method as described for the compound VIV-1 using the compound VII-18 as a starting material.

$^1$H-NMR (CDCl$_3$): 1.09 (s, 3H), 1.30-2.95 (m, 21H), 3.84 (s, 3H), 6.79 (t, J=4 Hz, 1H), 6.94 (d, J=4 Hz, 1H), 7.07 (br s, 1H). MS m/z (TOF ES$^+$): 508 (M+Na).

Compound VIV-17

3-{(13S,15R)-2-Bromo-4-fluoro-3-hydroxy-17-[(E)-methoxyimino]-13-methyl-7,8,9,11,12,13,14,15,16,17-decahydro-6H-cyclopenta[a]phenanthren-15-yl}-N-(5-methylthiazol-2-yl)propanamide

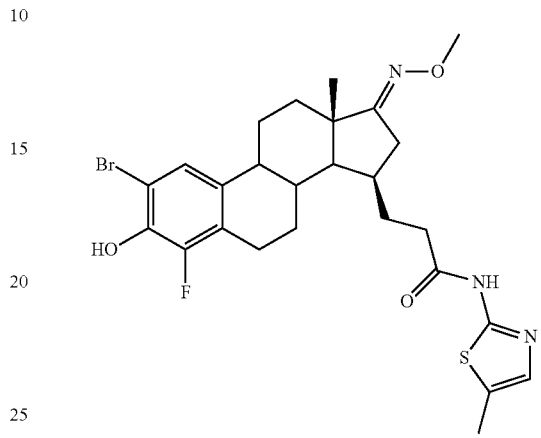

Prepared by the method as described for the compound VIV-1 using the compound VII-21 as a starting material.

$^1$H-NMR (CDCl$_3$): 1.10 (s, 3H), 1.53-2.90 (m, 21H), 3.84 (s, 3H), 7.06 (d, 1H), 7.17 (d, 1H). MS m/z (TOF ES$^+$): 564/566 (M$^+$).

Compound VIV-18

3-{(13S,15R)-4-Bromo-2-fluoro-3-hydroxy-17-[(E)-methoxyimino]-13-methyl-7,8,9,11,12,13,14,15,16,17-decahydro-6H-cyclopenta[a]phenanthren-15-yl}-N-(5-methylthiazol-2-yl)propanamide

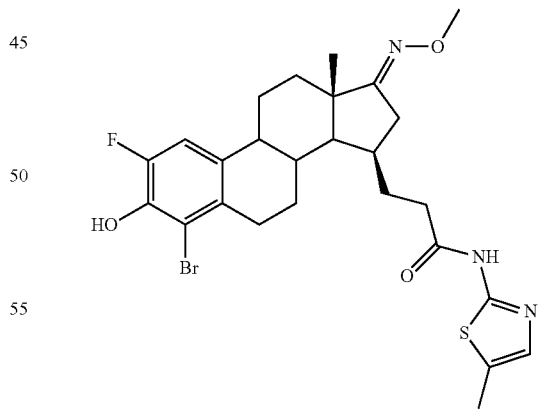

Prepared by the method as described for the compound VIV-1 using the compound VII-22 as a starting material.

$^1$H-NMR (CDCl$_3$): 1.09 (s, 3H), 1.25-2.91 (m, 21H), 3.85 (s, 3H), 7.01 (d, 1H), 7.07 (d, 1H). MS m/z (TOF ES$^+$): 564/566 (M$^+$).

Compound VIV-19

3-{(13S,15R)-3-hydroxy-17-[(E)-methoxyimino]-13-methyl-2-nitrile-7,8,9,11,12,13,14,15,16,17-decahydro-6H-cyclopenta[a]phenanthren-15-yl}-N-(5-methylthiazol-2-yl)propanamide

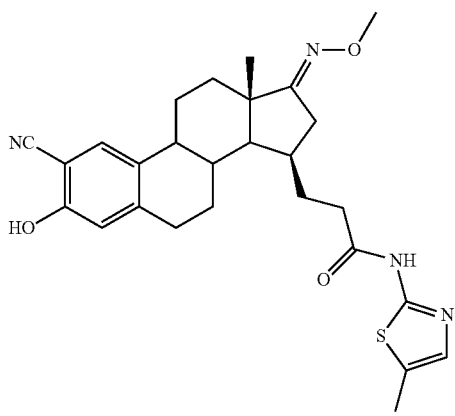

Prepared by the method as described for the compound VIV-1 using the compound VII-27 as a starting material in quantitative yield.

$^1$H-NMR (CDCl$_3$): 1.09 (s, 3H), 1.2-2.43 (m, 19H), 2.87 (m, 2H), 3.85 (s, 3H), 6.70 (s, 1H), 7.37 (s, 1H). MS m/z (TOF ES$^+$): 493 (M+1).

Compound VIV-20

3-{(13S,15R)-3-hydroxy-17-[(E)-methoxyimino]-13-methyl-4-nitrile-7,8,9,11,12,13,14,15,16,17-decahydro-6H-cyclopenta[a]phenanthren-15-yl}-N-(5-methylthiazol-2-yl)propanamide

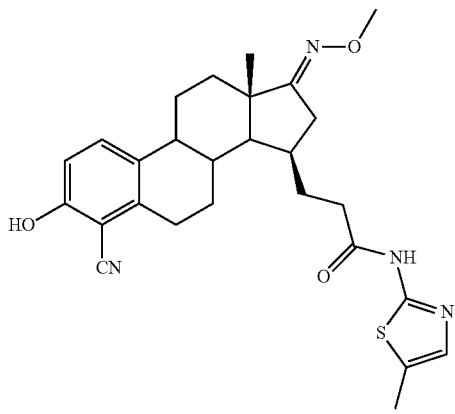 [SMILES: CO/N=C1\C[C@@H](CCC(=O)Nc2ncc(C)s2)C2C3CCc4c(ccc(O)c4C#N)C3CC[C@]12C]

Prepared by the method as described for the compound VIV-1 using the compound VII-28 as a starting material.

$^1$H-NMR (CDCl$_3$): 1.09 (s, 3H), 1.4-2.6 (m, 19H), 3.03 (m, 2H), 3.84 (s, 3H), 6.79 (d, 1H), 7.38 (d, 1H). MS m/z (TOF ES$^+$): 493 (M+1).

Compound VIV-21

3-{(13S,15R)-17-[(E)-Ethoxyimino]-3-hydroxy-13-methyl-7,8,9,11,12,13,14,15,16,17-decahydro-6H-cyclopenta[a]phenanthren-15-yl}-N-(5-methylthiazol-2-yl)propanamide

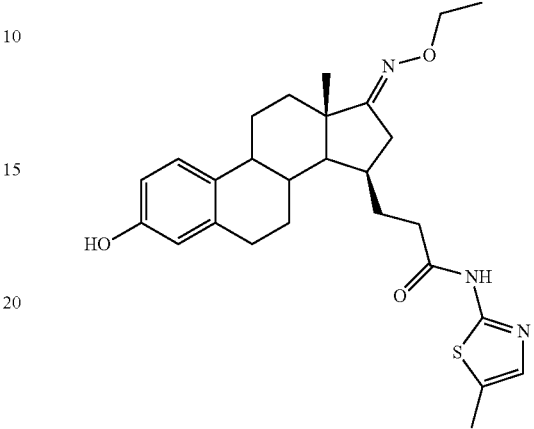

Prepared by the method as described for the compound VIV-1 using the compound VII as a starting material and ethyl hydroxylamine hydrochloride as a reagent, yield 82%.

$^1$H-NMR (DMSO-d$_6$): 1.03 (s, 3H), 1.17 (t, 3H), 1.2-2.9 (m, 18H), 2.33 (s, 3H), 3.98 (q, 2H), 6.50 (m, 2H), 7.04 (d, 1H), 7.11 (s, 1H), 9.04 (s, 1H), 11.91 (s, 1H). MS m/z (TOF ES$^+$): 504 (M+Na), 482 (M+1).

Synthesis of C-17 Oximes

C-17-Oximes were synthesized from C-17 ketones using the method described below:

Ketone (0.3 mmol) was dissolved in a mixture of ethanol (3 ml) and THF (2 ml) under nitrogen atmosphere. Pyridine (1.5 mmol) and hydroxylamine hydrochloride (0.9 mmol) were added to this solution. The reaction mixture was refluxed for 1-2 h. Solvents were evaporated. Water was added and the product was either filtered or extracted with ethyl acetate, washed with dilute hydrochlo-ric acid and finally with water. Oximes were purified further by flash-chromatography if required.

Compound VIV-22

3-{(13S,15R)-3-Hydroxy-17-[(E)-hydroxyimino]-13-methyl-7,8,9,11,12,13,14,15,16,17-decahydro-6H-cyclopenta[a]phenanthren-15-yl}-N-(5-methylthiazol-2-yl)propanamide

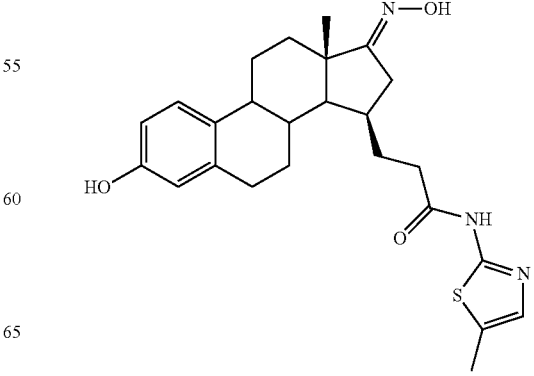

Prepared using the general method above using the compound VII as a starting material.

¹H-NMR (DMSO-d₆): 1.02 (s, 3H), 1.2-2.9 (m, 21H), 6.46 (s, 1H), 6.50 (d, 3H), 7.04 (d, 1H), 7.12 (s, 1H), 9.02 (s, 1H), 10.18 (s, 1H), 11.92 (s, 1H). MS m/z (TOF ES⁺): 476 (M+Na).

Compound VIV-23

3-{(13S,15R)-3-Hydroxy-2-nitro-17-[(E)-hydroxyimino]-13-methyl-7,8,9,11,12,13,14,15,16,17-decahydro-6H-cyclopenta[a]phenanthren-15-yl}-N-(5-methylthiazol-2-yl)propanamide

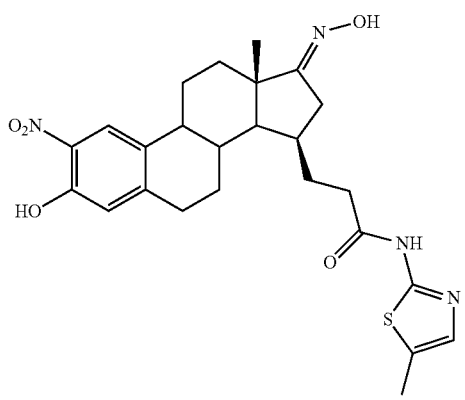 [SMILES: Cc1cnc(NC(=O)CC[C@@H]2C/C(=N\O)[C@@]3(C)CCC4c5cc([N+](=O)[O-])c(O)cc5CCC4C23)s1]

Prepared using the general method above using the compound 5 as a starting material.

¹H-NMR (CDCl₃): 1.15 (s, 3H), 1.30-2.75 (m, 18H), 2.85-3.05 (m, 3H), 6.87 (s, 1H), 7.06 (s, 1H), 7.97 (s, 1H) 8.50 (br s, 1H), 10.55 (br s, 1H). MS m/z (TOF ES⁺): 499 (M+H).

Compound VIV-24

3-{(13S,15R)-3-Hydroxy-4-nitro-17-[(E)-hydroxyimino]-13-methyl-7,8,9,11,12,13,14,15,16,17-decahydro-6H-cyclopenta[a]phenanthren-15-yl}-N-(5-methylthiazol-2-yl)propanamide

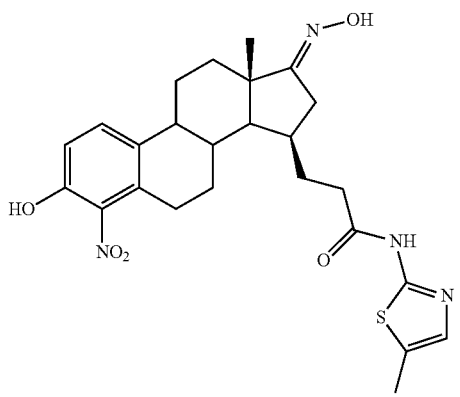 [SMILES: Cc1cnc(NC(=O)CC[C@@H]2C/C(=N\O)[C@@]3(C)CCC4c5ccc(O)c([N+](=O)[O-])c5CCC4C23)s1]

Prepared using the general method above using the compound 6 as a starting material.

1H-NMR (CDCl₃+MeOH-d₄): 1.13 (s, 3H), 1.30-3.30 (m, 21H), 6.91 (d, 1H), 7.04 (s, 1H), 7.39 (d, 1H). MS m/z (TOF ES⁺): 521 (M+Na).

Compound VIV-25

3-{(13S,15R)-2-Bromo-3-hydroxy-17-[(E)-hydroxyimino]-13-methyl-7,8,9,11,12,13,14,15,16,17-decahydro-6H-cyclopenta[a]phenanthren-15-yl}-N-(5-methylthiazol-2-yl)propanamide

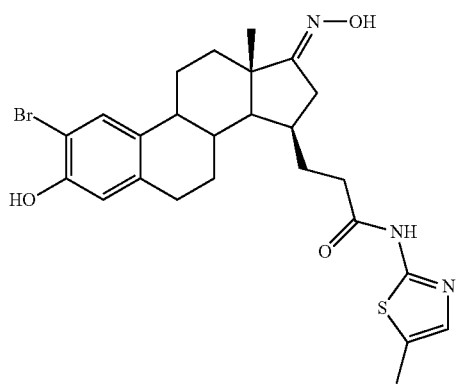 [SMILES: Cc1cnc(NC(=O)CC[C@@H]2C/C(=N\O)[C@@]3(C)CCC4c5cc(Br)c(O)cc5CCC4C23)s1]

Prepared using the general method above using the C-2 monobromide 19 as a starting material.

1H-NMR (CDCl₃+MeOH-d₄): 1.11 (s, 3H), 1.2-3.0 (m, 18H), 2.40 (s, 3H), 6.69 (s, 1H), 7.04 (s, 1H), 7.32 (d, 1H). MS m/z (TOF ES⁺): 532/534.

Compound VIV-26

3-{(13S,15R)-4-Bromo-3-hydroxy-17-[(E)-hydroxyimino]-13-methyl-7,8,9,11,12,13,14,15,16,17-decahydro-6H-cyclopenta[a]phenanthren-15-yl}-N-(5-methylthiazol-2-yl)propanamide

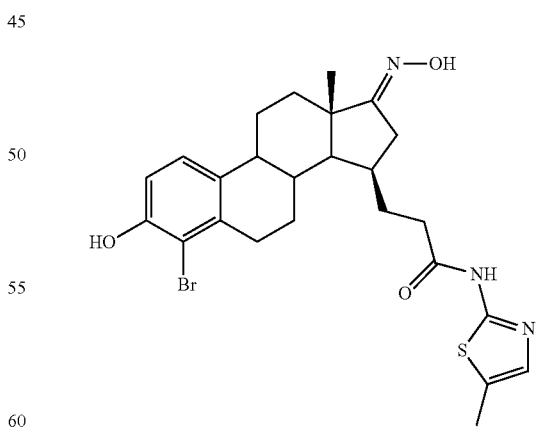

Prepared using the general method above using the C-4 monobromide 20 as a starting material.

1H-NMR (CDCl₃+MeOH-d₄): 1.11 (s, 3H), 1.2-3.0 (m, 18H), 2.41 (s, 3H), 6.82 (d, 1H), 7.06 (s, 1H), 7.14 (d, 1H). MS m/z (TOF ES⁺): 532/534.

Compound VIV-27

3-{(13S,15R)-2,4-Dibromo-3-hydroxy-17-[(E)-hydroxyimino]-13-methyl-7,8,9,11,12,13,14,15,16,17-decahydro-6H-cyclopenta[a]phenanthren-15-yl}-N-(5-methylthiazol-2-yl)propanamide

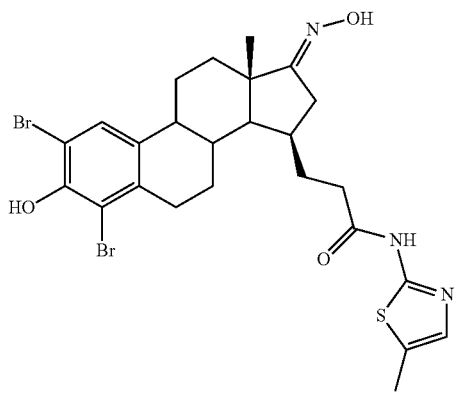 [SMILES: Cc1cnc(NC(=O)CC[C@@H]2C/C(=N\O)[C@@]3(C)CCC4c5cc(Br)c(O)c(Br)c5CCC4C23)s1]

Prepared using the general method above using the dibromide 21 as a starting material.

$^1$H-NMR (DMSO-$d_6$): 1.00 (s, 3H), 1.25-2.95 (m, 21H), 7.11 (s, 1H) 7.40 (s, 1H), 9.54 (s, 1H), 10.20 (s, 1H), 11.93 (s, 1H). MS m/z (TOF ES$^+$): 632/634/636 (M+Na).

Compound VIV-28

3-{(13S,15R)-2-Chloro-3-hydroxy-17-[(E)-hydroxyimino]-13-methyl-7,8,9,11,12,13,14,15,16,17-decahydro-6H-cyclopenta[a]phenanthren-15-yl}-N-(5-methylthiazol-2-yl)propanamide

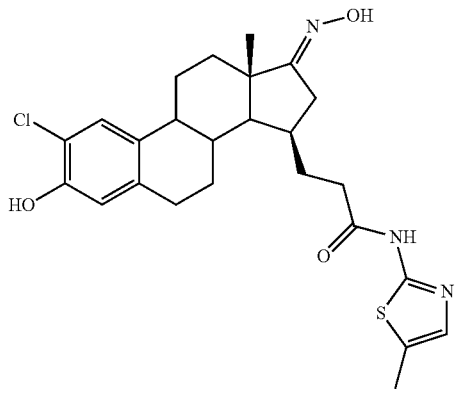 [SMILES: Cc1cnc(NC(=O)CC[C@@H]2C/C(=N\O)[C@@]3(C)CCC4c5cc(Cl)c(O)cc5CCC4C23)s1]

Prepared using the general method above using the C-2 chloride 23 as a starting material.

$^1$H-NMR (CDCl$_3$): 1.10 (s, 3H), 1.30-3.0 (m, 21H), 6.69 (s, 1H), 7.04 (s, 1H), 7.17 (s, 1H). MS m/z (TOF ES$^+$): 510/512 (M+Na).

Compound VIV-29

3-{(13S,15R)-4-Chloro-3-hydroxy-17-[(E)-hydroxyimino]-13-methyl-7,8,9,11,12,13,14,15,16,17-decahydro-6H-cyclopenta[a]phenanthren-15-yl}-N-(5-methylthiazol-2-yl)propanamide

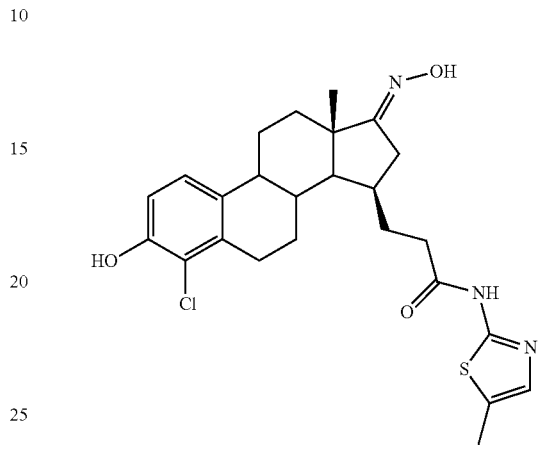

Prepared using the general method using the C-4 chloride 22 as a starting material.

$^1$H-NMR (CDCl$_3$): 1.10 (s, 3H), 1.30-3.05 (m, 21H), 6.80 (d, 1H), 7.05 (s, 1H), 7.08 (d, 1H). MS m/z (TOF ES$^+$): 510/512 (M+Na).

Compound VIV-30

3-{(13S,15R)-2,4-Dichloro-3-hydroxy-17-[(E)-hydroxyimino]-13-methyl-7,8,9,11,12,13,14,15,16,17-decahydro-6H-cyclopenta[a]phenanthren-15-yl}-N-(5-methylthiazol-2-yl)propanamide

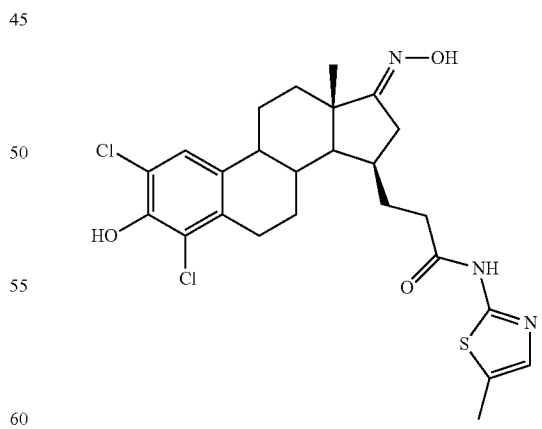

Prepared using the general method above using C-2,4 dichloride 24 as a starting material.

1H-NMR (CDCl$_3$+MeOH-$d_4$): 1.11 (s, 3H), 1.4-3.0 (m, 18H), 2.39 (s, 3H), 7.03 (s, 1H), 7.19 (s, 1H). MS m/z (TOF ES$^+$): 522/524.

Compound VIV-31

3-{(13S,15R)-2-Fluoro-3-hydroxy-17-[(E)-hydroxy-imino]-13-methyl-7,8,9,11,12,13,14,15,16,17-deca-hydro-6H-cyclopenta[a]phenanthren-15-yl}-N-(5-methylthiazol-2-yl)propanamide

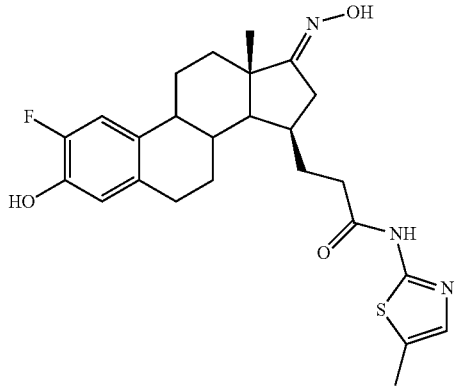 [SMILES: Cc1cnc(NC(=O)CC[C@@H]2C/C(=N\O)[C@@]3(C)CCC4c5cc(F)c(O)cc5CCC4C23)s1]

Prepared using the general method above using the C-2 fluoride 26 as a starting material.

$^1$H-NMR (CDCl$_3$+MeOH-d$_4$): 1.10 (s, 3H), 1.25-3.0 (m, 21H), 6.66 (d, J=10 Hz, 1H), 6.92 (d, J=12 Hz, 1H), 7.04 (br s, 1H). MS m/z (TOF ES$^+$): 472 (M+H).

Compound VIV-1a

Potassium (13S,15R,E)-17-(methoxyimino)-13-methyl-15-(3-((5-methylthiazol-2-yl)amino)-3-oxo-propyl)-7,8,9,11,12,13,14,15,16,17-decahydro-6H-cyclopenta[a]phenanthren-3-olate

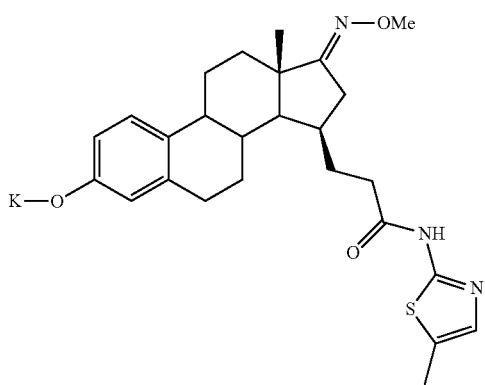

VIV-1 (200 mg, 0.43 mmol) was dissolved in ethanol (1.5 ml) and KOH (36 mg, 0.64 mmol, 150 mol-%) was added in methanol (300 μl). The reaction mixture was stirred at rt for 60 minutes, then solvents were evaporated. The precipitate was triturated with diethylether-ethanol (v/v 2:1) mixture, finally washed with ether and dried carefully yielding 192 mg of the product.

$^1$H-NMR (DMSO-d$_6$): 1.03 (s, 3H), 1.30-2.90 (m, 22H), 3.72 (s, 3H), 6.36-6.43 (m, 2H), 6.71 (s, 1H), 6.92 (d, 1H).

Compound VIV-1b 3-((13S,15R,E)-3-hydroxy-17-(methoxyimino)-13-methyl-7,8,9,11,12,13,14,15,16,17-decahydro-6H-cyclopenta[a]phenanthren-15-yl)-N-(5-methylthiazol-2-yl)propanamide hydrochloride

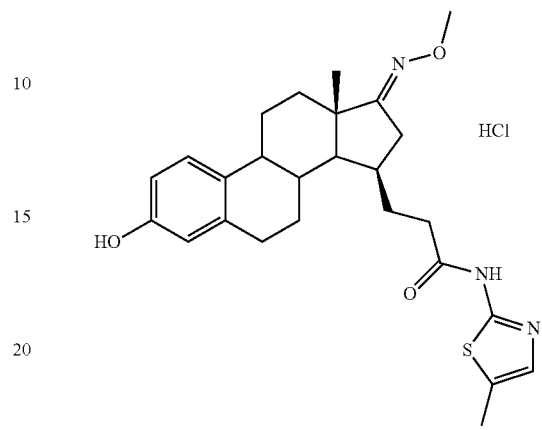

VIV-1 (200 mg, 0.43 mmol) was dissolved in EtOAc (1 ml) and 2N HCl in EtOAc (0.5 ml) was added. The reaction mixture was stirred at rt for 30 minutes, when the product started to precipitate. The solvent was evaporated and the crude product was triturated with EtOAc. The product was filtered and washed several times with EtOAc and dried yielding 154 mg of the product.

$^1$H-NMR (DMSO-d$_6$): 1.03 (s, 3H), 1.25-2.90 (m, 23H), 3.78 (s, 3H), 6.47-6.53 (m, 2H), 7.02 (s, 1H), 7.13 (d, 1H), 12.01 (br s, 1H).

C3 Derivatives

Compound 1

Phosphoric acid mono-{(13S,15R)-17[(E)-methoxy-imino]-13-methyl-15-[2-(5-methylthiazol-2-ylcar-bamoyl)ethyl-7,8,9,11,12,13,14,15,16,17-decahydro-6H-cyclopenta[a]phenanthren-3-yl} ester

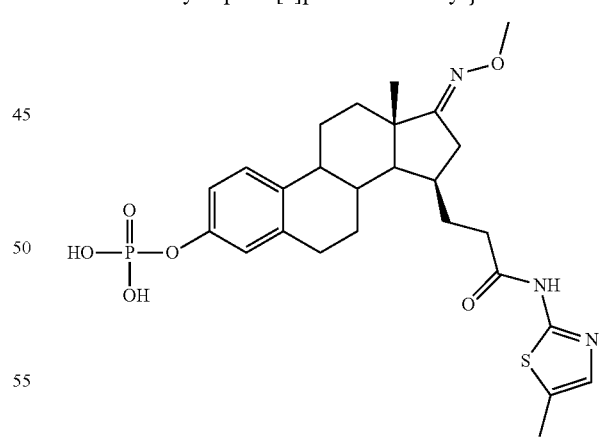

VIV-1 (3.0 g, 6.42 mmol, 100 mol-%) was dissolved in dry THF (40 ml). Pyridine (2.1 ml, 400 mol-%) and phosphorous oxychloride (2.4 ml, 400 mol-%) were added, and the solution was stirred at rt for four hours under nitrogen. The solution cooled and 60 ml of water was carefully added. Stirring was continued overnight. THF was evaporated. The precipitate solution was made basic with 2N NaOH-solution. After washing with EtOAc (3×30 ml), the water phase was acidified with conc. HCl. The product precipitated and then filtered. The solid material was washed several times with water (5×60 ml). The crude product (3.6 g) was co-evaporated with toluene and ethanol.

$^1$H-NMR (DMSO-$d_6$): 1.04 (s, 3H), 1.36-2.90 (m, 23H), 3.73 (s, 3H), 6.88-6.92 (m, 2H), 7.11 (s, 1H), 7.23 (d, 1H), 11.93 (br s, 1H).

Compound 1a

Phosphoric acid mono-{(13S,15R)-17-[(E)-methoxyimino]-13-methyl-15-[2-(5-methylthiazol-2-ylcarbamoyl)ethyl-7,8,9,11,12,13,14,15,16,17-decahydro-6H-cyclopenta[a]phenanthren-3-yl} ester disodium salt

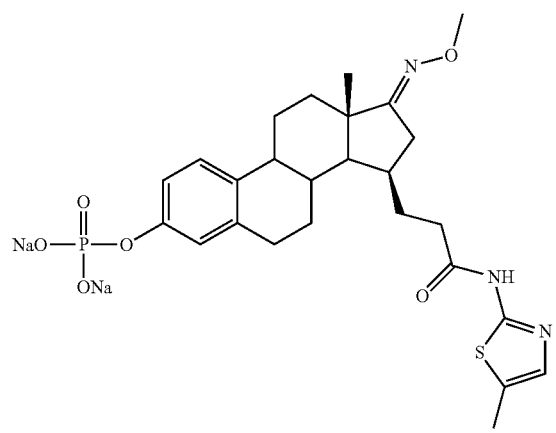

Phosphoric acid crude product (3.6 g) was dissolved in abs. ethanol (35 ml) and then NaOH (1.1 g) dissolved in abs. ethanol was added. After stirring for two hours, solvents were evaporated. The precipitate was washed several times with Et$_2$O and EtzO:EtOH (3:1). The yield of the phosphate disodium salt was 3.7 g.

$^1$H-NMR (MeOH-$d_4$+D20): 1.11 (s, 3H), 1.30-1.63 (m, 6H), 1.98-2.46 (14H), 2.73-2.90 (m, 2H), 3.80 (s, 3H), 7.03-7.15 (m, 4H). $^{31}$P-NMR (MeOH-$d_4$+D20): 0.56. MS m/z (TOF ES+): 592 (M+1), 570 (—PO$_3$H$_2$+Na).

Compound 2 tert-Butoxycarbonylamino-acetic acid (13S,15R)-13-methyl-17[(E)-methoxyimino]-15-[2-(5-methyl-thiazol-2-ylcarbamoyl)-ethyl]-7,8,9,11,12,13,14,15,16,17-decahydro-6H-cyclopenta[a]phenanthren-3-yl ester

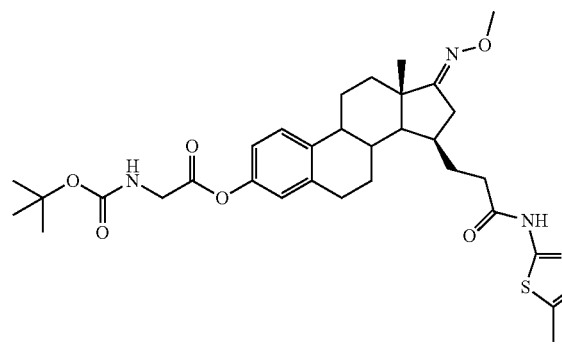

VIV-1 (500 mg, 1.1 mmol, 100 mol-%) was dissolved in DCM (10 ml) and pyridine (173 µl, 200 mol-%), BOC-glycine (225 mg, 120 mol-%) and DCC (330 mg, 150 mol-%) were added to the reaction mixture. Additional amounts of reagents (30% of the original amounts) were added after six hours and then stirring was continued at rt overnight. The precipitated DHU was filtered off, and the filtrate was washed with water and several times with dilute HCl-solution, followed by washing with water and finally with brine. The crude product was purified by chromatography using DCM-MeOH (v/v 99:1) as an eluent. The amount of the product was 599 mg.

$^1$H-NMR (DMSO-$d_6$): 1.04 (s, 3H), 1.39 (s, 9H), 1.45-2.20 (m, 14H), 2.07-2.95 (m, 7H), 3.65 (d, 2H), 3.73 (s, 3H), 3.92 (d, 2H), 6.82-6.86 (m, 2H), 7.11 (s, 1H), 11.90 (br s, 1H).

Compound 3a

Aminoacetic acid (13S,15R)-13-methyl-17[(E)-methoxyimino]-15-[2-(5-methyl-thiazol-2-ylcarbamoyl)-ethyl]-7,8,9,11,12,13,14,15,16,17-decahydro-6H-cyclopenta[a]phenanthren-3-yl ester trifluoroacetate

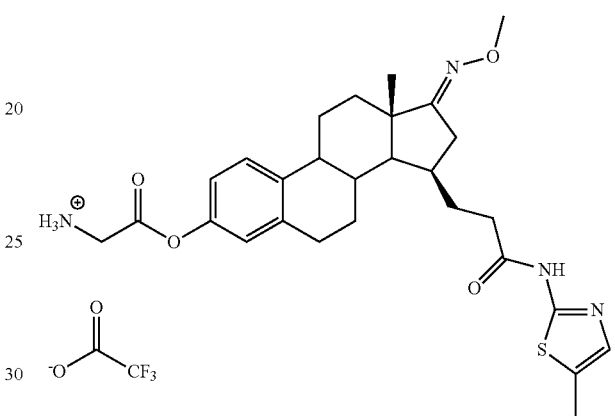

Boc-protected glycine derivative 2 (310 mg, 0.5 mmol) was dissolved in DCM (5 ml) and cooled with ice bath. Trifluoroacetic acid (1 ml) was added dropwise, and then the reaction mixture was stirred at rt for two hours. Solvents were evaporated. The precipitate was triturated with Et$_2$O (5×2 ml) affording the TFA-salt 360 mg.

$^1$H-NMR (DMSO-$d_6$): 1.05 (s, 3H), 1.41-2.25 (m, 13H), 2.33-2.40 (s+m, 4H), 2.60-2.92 (m, 3H), 3.73 (s, 3H), 3.82 (s, 2H), 4.11 (s, 2H), 6.89-6.94 (m, 2H), 7.11 (s, 1H), 7.36 (d, 2H), 11.92 (s, 1H). MS m/z (TOF ES+): 547 (−TFA; M+Na), 525 (−TFA; M+H).

Compound 3b

Aminoacetic acid (13S,15R)-13-methyl-17[(E)-methoxyimino]-15-[2-(5-methyl-thiazol-2-ylcarbamoyl)-ethyl]-7,8,9,11,12,13,14,15,16,17-decahydro-6H-cyclopenta[a]phenanthren-3-yl ester hydrochloride

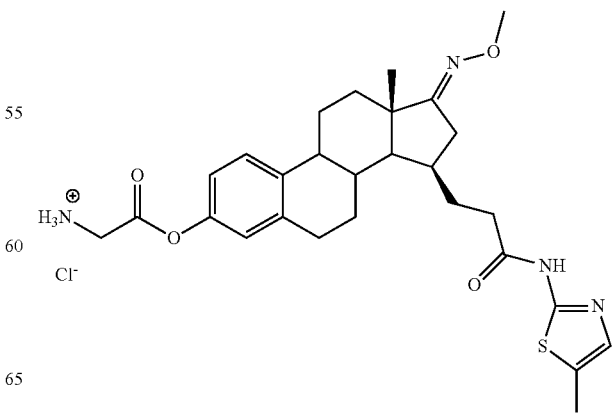

Boc-protected glycine derivative 2 (340 mg, 0.5 mmol) was dissolved in EtOAc (3 ml) and 2N HCl-solution was added. The reaction mixture was stirred at rt for an hour, then the solvent was evaporated, followed by co-evaporation with toluene. Finally EtOAc (2 ml) was added, and the solid material formed was filtered and washed several times with EtOAc affording the HCl-salt (260 mg).

$^1$H-NMR (MeOH-d$_4$): 1.13 (s, 3H), 1.31-1.80 (m, 7H), 2.15-3.10 (m, 17H), 3.80 (s, 3H), 4.12 (s, 2H), 6.92 (m, 2H), 7.28-7.37 (m, 2H). MS m/z (TOF ES+): 547 (—HCl; M+Na), 525 (—HCl; M+H).

Compound 4

Tert-Butoxycarbonyl-methylamino-acetic acid (13S, 15R)-13-methyl-17[(E)-methoxyimino]-15-[2-(5-methyl-thiazol-2-ylcarbamoyl)-ethyl]-7,8,9,11,12,13,14,15,16,17-decahydro-6H-cyclopenta[a]phenanthren-3-yl ester

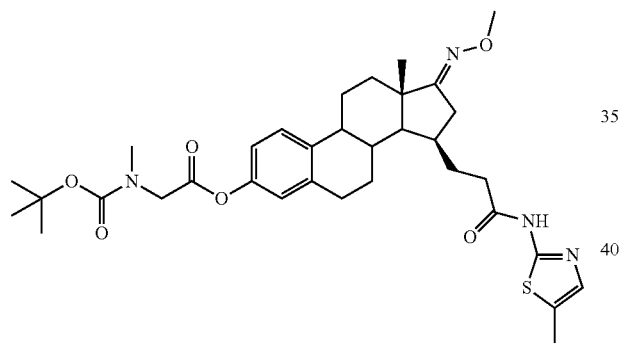

VIV-1 (500 mg, 1.1 mmol, 100 mol-%) was dissolved in DCM (12 ml). Boc-Sar-OH (326 mg, 200 mol-%), N-methylmorpholine (350 µl, 300 mol-%) and 1-hydroxy-1-H-benzotriazole (289 mg, 200 mol-%) were added. The reaction mixture was stirred for 5 minutes and then was cooled with ice-bath. EDCI (451 mg, 220 mmol-%) was added, after stirring for 30 minutes at cold, then overnight at rt. To the reaction mixture was added 1N HCl-solution (10 ml), then the product was extracted with DCM. The crude product was purified by chromatography using DCM-MeOH 98:2 as an eluent affording the product (520 mg; 76%).

$^1$H-NMR (DMSO-d$_6$): 1.05 (s, 3H), 1.34-2.91 (m, 33H), 3.73 (s, 3H), 4.20 (s, 2H), 6.83-6.88 (m, 2H), 7.10 (s, 1H), 7.31-7.35 (m, 1H), 11.90 (br s, 1H). MS m/z (TOF ES+) 661 (M+Na).

Compound 5a

Methylamino-acetic acid (13S,15R)-13-methyl-17[(E)-methoxyimino]-15-[2-(5-methyl-thiazol-2-yl-carbamoyl)-ethyl]-7,8,9,11,12,13,14,15,16,17-decahydro-6H-cyclopenta[a]phenanthren-3-yl ester hydrochloride

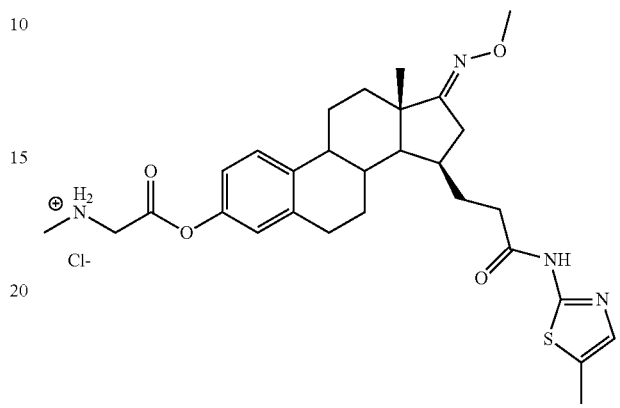

The Boc-protected sarcosine 4 (500 mg, 0.8 mmol) in EtOAc was unprotected by addition of 2N HCl-EtOAc-solution. The reaction mixture was stirred for an hour, followed by evaporation of the solvent. The precipitate was triturated several times with Et$_2$O, heptane and finally with EtOAc. The yield of the product was 453 mg; quant.

$^1$H-NMR (DMSO-d$_6$): 1.05 (s, 3H), 1.40-2.64 (m, 22H), 2.89 (br s, 2H), 3.74 (s, 3H), 4.23 (s, 2H), 6.91-6.97 (m, 2H), 7.12 (s, 1H), 7.36 (d, 1H), 9.52 (br s, 2H), 11.99 (br s, 1H). MS m/z (TOF ES+) 561 (M+Na), 539 (M+1).

Compound VV

Chloroacetic acid (13S,15R)-13-methyl-17[(E)-methoxyimino]-15-[2-(5-methyl-thiazol-2-ylcarbamoyl)-ethyl]-7,8,9,11,12,13,14,15,16,17-decahydro-6H-cyclopenta[a]phenanthren-3-yl ester

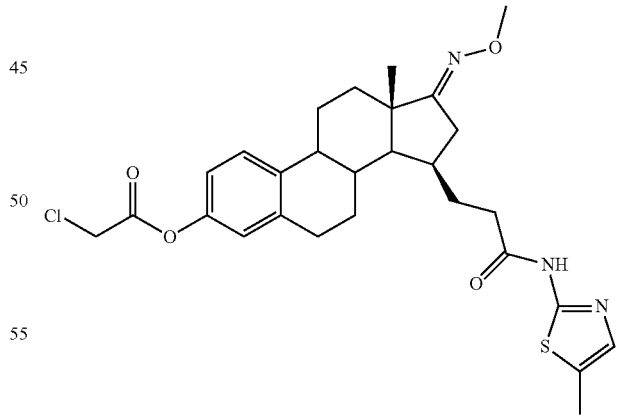

VIV-1 (500 mg, 1.1 mmol, 100 mol-%) was dissolved in DCM (5 ml) under nitrogen atmosphere and pyridine was added (215 µl, 2.7 mmol, 250 mol-%). Reaction was cooled with ice bath and chloroacetyl chloride (215 µl, 2.7 mmol, 250 mol-%) dissolved in DCM (2 ml) was added. Reaction was stirred at 0° C. for 1.5 hours and at rt for 40 min. Water (10 ml) was added and layers separated. Water layer was extracted with DCM (3×5 ml). Combined organic layers were extracted with 1N HCl (1×10 ml), 1N NaOH (1×10 ml), water (3×30 ml), brine (3×15 ml) and dried with Na₂SO₄. The amount of the crude product was 517 mg.

¹H-NMR (DMSO-d₆): 1.04 (s, 3H), 1.40-2.74 (m, 19H), 2.87 (br s, 2H), 3.73 (s, 3H), 4.66 (s, 2H), 6.88-6.92 (m, 2H), 7.11 (s, 1H), 7.33 (d, 1H), 11.90 (br s, 1H).

Compound 6

Morpholin-4-yl-acetic acid (13S,15R)-13-methyl-17 [(E)-methoxyimino]-15-[2-(5-methyl-thiazol-2-yl-carbamoyl)-ethyl]-7,8,9,11,12,13,14,15,16,17-decahydro-6H-cyclopenta[a]phenanthren-3-yl ester

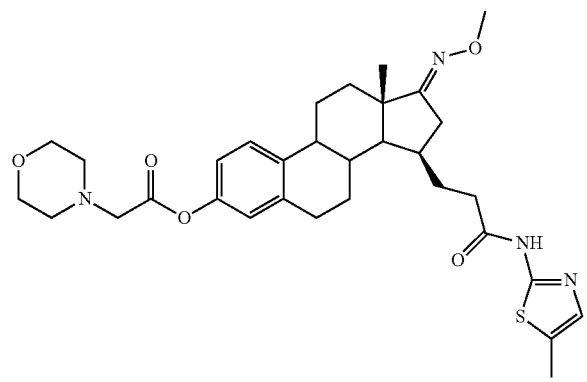 [SMILES: CO/N=C1\C[C@@H](CCC(=O)Nc2ncc(C)s2)C2C3CCc4cc(OC(=O)CN5CCOCC5)ccc4C3CC[C@]12C]

VV (200 mg, 0.37 mmol, 100 mol-%) was dissolved in dry THF (4 ml) and NaI (165 mg, 1.1 mmol, 300 mol-%) was added. Reaction was stirred at rt for 1 hour. Reaction was cooled with ice-bath to 0° C. and morpholine (48 µl, 0.55 mmol, 150 mol-%) dissolved in dry THF (1 ml) was added slowly. Stirring at 0° C. was continued for 1.5 hour, then at rt for 3 hours. Morpholine (24 µl) was added and stirring continued until completed. EtOAc (10 ml) was added and reaction mixture was poured in to ice-cold 0.1 N HCl (10 ml). Layers were separated and water layer was extracted with EtOAc (3×5 ml). Combined organic layers were extracted with water (3×10 ml) and brine (3×10 ml) and dried with MgSO₄. Amount of the crude product was 190 mg; 87%.

¹H-NMR (DMSO-d₆): 1.05 (s, 3H), 1.40-2.39 (m, 18H), 2.58 (m, 4H), 2.86 (br s, 2H), 3.49 (s, 2H), 3.60 (m, 4H), 3.73 (s, 3H), 4.23 (s, 2H), 6.84-6.88 (m, 2H), 7.11 (s, 1H), 7.30 (d, 1H), 11.90 (br s, 1H). MS m/z (TOF ES+) 617 (M+Na), 595 (M+1).

Compound 7

1-(tert-butyl) 2-(13S,15R,E)-17-(methoxyimino)-13-methyl-15-(3-((5-methylthiazol-2-yl)amino)-3-oxopropyl)-7,8,9,11,12,13,14,15,16,17-decahydro-6H-cyclopenta[a]phenanthren-3-yl) pyrrolidine-1,2-dicarboxylate

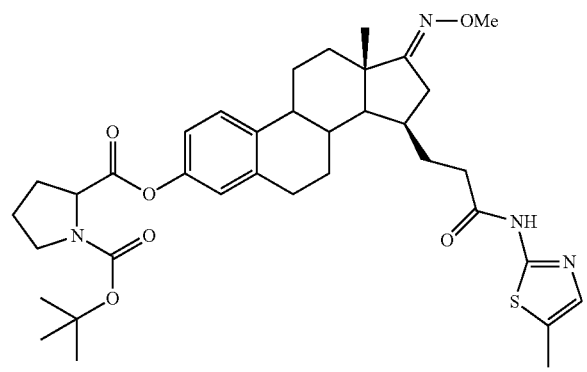 [SMILES: CO/N=C1\C[C@@H](CCC(=O)Nc2ncc(C)s2)C2C3CCc4cc(OC(=O)C5CCCN5C(=O)OC(C)(C)C)ccc4C3CC[C@]12C]

The compound 7 was prepared by using the same method as for the compound 4 using VIV-1 as starting material and Boc-Pro-OH as reagent in 83% yield. Reaction needed higher amount of the reagents to be completed; N-methylmorpholine 380 mol-%, 1-hydroxy-1-H-benzotriazole 220 mol-% and EDCI 290 mol-%.

¹H-NMR (CDCl₃): 1.11 (s, 3H), 1.48 (s, 9H), 1.20-3.10 (m, 25H), 3.38-3.69 (m, 2H), 3.85 (s, 3H), 4.41-4.55 (m, 1H), 6.80-6.87 (m, 2H), 7.06 (s, 1H), 7.24-7.31 (m, 1H), 12.14 (br s, 1H). MS m/z (TOF ES+): 687 (M+Na).

Compound 8a (13S,15R,E)-17-(methoxyimino)-13-methyl-15-(3-((5-methylthiazol-2-yl)amino)-3-oxopropyl)-7,8,9,11,12,13,14,15,16,17-decahydro-6H-cyclopenta[a]phenanthren-3-yl prolinate trifluoroacetate

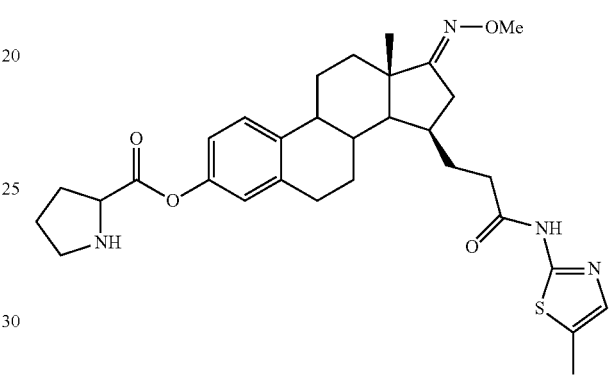

The Boc-protected proline derivative 7 (540 mg, 0.81 mmol) in DCM was unprotected by addition of trifluoroacetic acid (TFA) (1.6 ml). The reaction mixture was stirred first in ice-bath for 3 hours and then at rt for an hour, followed by evaporation of the solvent. The precipitate was triturated several times with Et₂O yielding 350 mg of the product, the yield 69%.

¹H-NMR (CDCl₃): 1.09 (s, 3H), 1.27-2.91 (m, 25H), 3.45-3.52 (m, 2H), 3.84 (s, 3H), 4.60-4.67 (m, 1H), 6.79-6.85 (m, 2H), 7.09 (s, 1H), 7.24-7.29 (m, 1H).

Compound 8b (13S,15R,E)-17-(methoxyimino)-13-methyl-15-(3-((5-methylthiazol-2-yl)amino)-3-oxopropyl)-7,8,9,11,12,13,14,15,16,17-decahydro-6H-cyclopenta-[a]phenanthren-3-yl prolinate hydrochloride

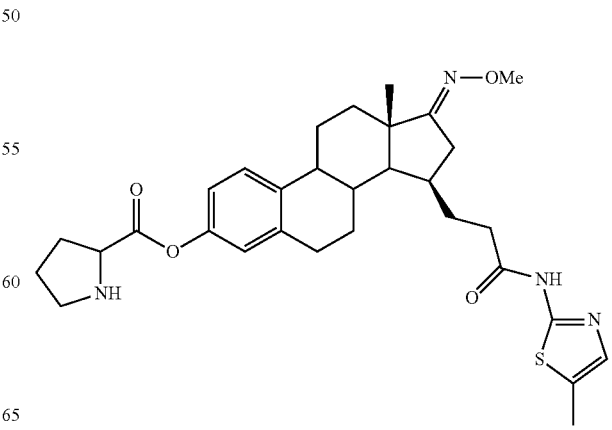

HCl salt of the product 8 was prepared by dissolving TFA salt FP-5683 All (380 mg) in EtOAc (3 ml) and adding 4 M HCl (300 μl). Reaction was stirred for an hour. Trituration several times with Et₂O end EtOAc yielding 222 mg of the product.

¹H-NMR (DMSO-d₆): 1.05 (s, 3H), 1.27-3.05 (m, 27H), 3.10-3.45 (m, 3H), 3.73 (s, 3H), 4.63 (m, 1H), 6.97-7.01 (m, 2H), 7.12 (s, 1H), 7.36 (m, 1H), 9.32 (br s, 1H), 10.36 (br s, 1H), 11.97 (br s, 1H).

Compound 9 di-tert-butyl(((((13S,15R,E)-17-(methoxyimino)-13-methyl-15-(3-((5-methylthiazol-2-yl)amino)-3-oxo-propyl)-7,8,9,11,12,13,14,15,16,17-decahydro-6H-cyclopenta[a]phenanthren-3-yl)oxy)methyl) phosphate

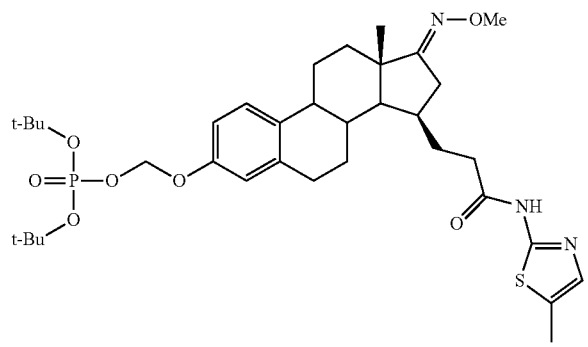 [SMILES: CO/N=C1\C[C@@H](CCC(=O)Nc2ncc(C)s2)C2C3CCc4cc(OCOP(=O)(OC(C)(C)C)OC(C)(C)C)ccc4C3CC[C@]12C]

Starting material VIV-1 (770 mg, 1.65 mmol, 100 mol-%) was dissolved in dry DMF (10 ml). Di-tert-butyl chloromethyl phosphate [85%] (600 mg, 1.97 mmol, 120 mol-%) and tetrabutylammoniumiodide (Bu4NI) (123 mg, 0.33 mmol, 20 mol-%) were added. Reaction was cooled to 0° C. NaH [60%](145 mg, 3.62 mmol, 220 mol-%) was carefully added. Reaction was stirred first at 0° C. for 30 min and then at rt for 5 hours. NaH (35 mg) was added and reaction stirred overnight. Reaction was quenched with 10% citric acid (20 ml) and extracted with EtOAc (3×20 ml). Combined organic layers were extracted with 10% citric acid (1×20 ml), water (2×30 ml) and brine (2×30 ml) and dried with Na₂SO₄. The crude product was triturated with heptane:EtOAc (8:2) yielding 1.03 g (91%) of the product.

¹H-NMR (DMSO-d₆): 1.03 (s, 3H), 1.10-2.90 (m, 21H), 1.39 (s, 18H), 3.73 (s, 3H), 5.51-5.57 (d, 2H), 6.79-6.84 (m, 2H), 7.11 (s, 1H), 7.20-7.24 (m, 1H), 11.90 (br s, 1H)

Compound 10

(((13S,15R,E)-17-(methoxyimino)-13-methyl-15-(3-((5-methylthiazol-2-yl)amino)-3-oxopropyl)-7,8,9,11,12,13,14,15,16,17-decahydro-6H-cyclopenta-[a]phenanthren-3-yl)oxy)methyl dihydrogen phosphate

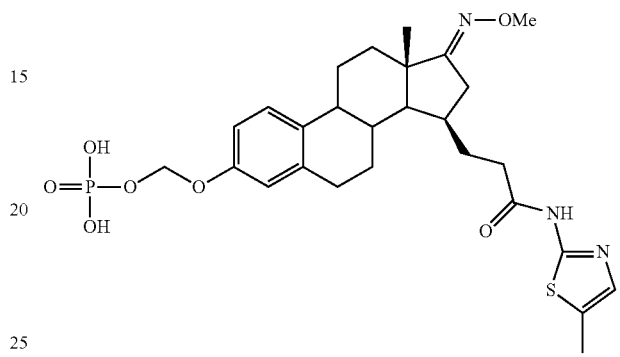

9 (1.0 g, 1.45 mmol, 100 mol-%) was dissolved in dry DCM (7 ml). Reaction was cooled to 0° C. Trifluoroacetic acid (222 μl, 2.90 mmol, 200 mol-%) was dissolved in dry DCM (1 ml) and added in reaction. Reaction was stirred first at 0° C. for few hours and then at rt overnight. TFA (111 μl, 100 mol-%) was added and stirring continued. Total reaction time was three days and additional amount (111 μl, 100 mol-%) of TFA was added. Solvent was evaporated and EtOAc was added (100 ml). Solid material was filtered and washed with EtOAc (5×3 ml) and Et₂O (2×3 ml) to yield 320 mg of the product.

¹H-NMR (DMSO-d₆): 1.04 (s, 3H), 1.10-2.90 (m, 23H), 3.73 (s, 3H), 5.47-5.53 (d, 2H), 6.79-6.84 (m, 2H), 7.11 (s, 1H), 7.19-7.23 (m, 1H), 11.89 (br s, 1H).

Compound 10a (((13S,15R,E)-17-(methoxyimino)-13-methyl-15-(3-((5-methylthiazol-2-yl)amino)-3-oxopropyl)-7,8,9,11,12,13,14,15,16,17-decahydro-6H-cyclopenta[a]phenanthren-3-yl)oxy)methyl dihydrogen phosphate disodium salt Starting material 10 (310 mg, 0.54 mmol, 100 mol-%) was dissolved in EtOH (10-15 ml). NaOH-EtOH-solution (NaOH 86 mg, 2.15 mmol, 400 mol-% and EtOH 2 ml) was added and reaction stirred for 3.5 hours. Precipitate was filtered and washed with EtOH:Et₂O (0.5:3) (3×3 ml) and Et₂O (2×3 ml) yielding 140 mg of the product.

¹H-NMR (D₂O): 1.01 (s, 3H), 1.10-2.90 (m, 21H), 3.76 (s, 3H), 5.40-5.44 (d, 2H), 6.83-6.88 (m, 2H), 7.06 (s, 1H), 7.20-7.31 (m, 1H). ³¹P-NMR (D₂O): 0.86. MS m/z (TOF ES+): 622 (M+1).

Compound 11

(13S,15R,E)-2,4-dibromo-17-(hydroxyimino)-13-methyl-15-(3-((5-methylthiazol-2-yl)amino)-3-oxo-propyl)-7,8,9,11,12,13,14,15,16,17-decahydro-6H-cyclopenta[a]phenanthren-3-yl acetate

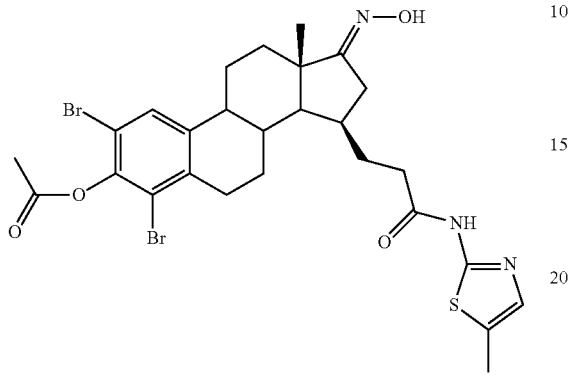

VIII-29 (48 mg, 0.08 mmol, 100 mol-%) was suspended in ethanol (5 ml). Hydroxyamine hydrochloride (26 mg, 0.38 mmol, 500 mol-%) and pyridine (73 µl, 0.90 mmol, 1200 mol-%) were added and the mixture was stirred at rt under nitrogen for 3 h. The solvent was evaporated and EtOAc (5 ml) and water (5 ml) were added into the residue. The mixture was stirred vigorously and the organic layer was washed with 0.25 M HCl, water and brine. The organic layer was dried with $Na_2SO_4$ and evaporated to afford 57 mg of the crude product, con-taining the acetate (67%) with of C-3 hydrolysed C-17 oxime VIV-32 (31%).

$^1$H-NMR (DMSO-$d_6$): 1.02 (s, 3H), 1.10-2.90 (m, 21H), 2.38 (s, 3H), 7.11 (s, 1H), 7.61 (s, 1H), 10.19 (s, 1H), 11.91 (brs, 1H).

VIV-32: C-3 hydrolysed impurity (31% of the crude product):

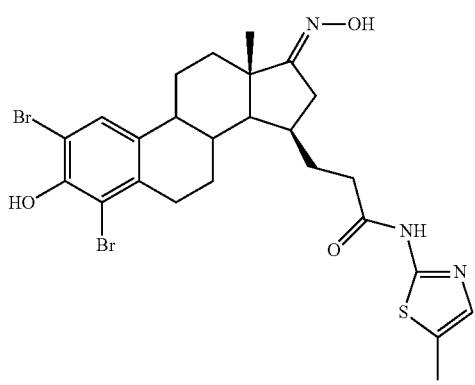 [SMILES: Cc1cnc(NC(=O)CC[C@@H]2C/C(=N\O)[C@@]3(C)CCC4c5cc(Br)c(O)c(Br)c5CCC4C23)s1]

$^1$H-NMR (DMSO-$d_6$): 1.00 (s, 3H), 1.25-2.95 (m, 21H), 7.11 (s, 1H) 7.40 (s, 1H), 9.54 (s, 1H), 10.20 (s, 1H), 11.93 (s, 1H). MS m/z (TOF ES$^+$): 632/634/636 (M+Na).

Compound 12

(13S,15R,E)-2,4-dibromo-17-(methoxyimino)-13-methyl-15-(3-((5-methylthiazol-2-yl)amino)-3-oxo-propyl)-7,8,9,11,12,13,14,15,16,17-decahydro-6H-cyclopenta[a]phenanthren-3-yl acetate

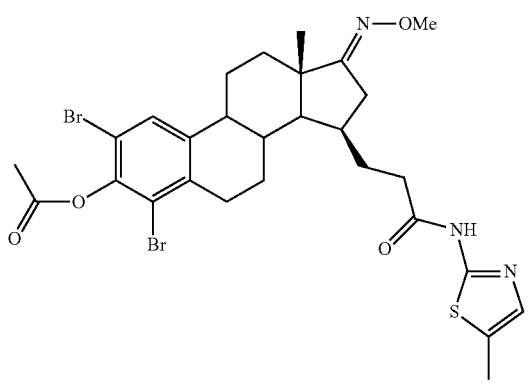 [SMILES: CO/N=C1\C[C@@H](CCC(=O)Nc2ncc(C)s2)C2C3CCc4c(cc(Br)c(OC(C)=O)c4Br)C3CC[C@]12C]

VIV-11 (100 mg, 0.16 mmol, 100 mol-%) and DMAP (6 mg, 0.05 mmol, 30 mol-%) were suspended in dry DCM (3 ml). Pyridine (155 µl, 1.92 mmol, 1200 mol-%) and acetic anhydride (75 µl, 0.80 mmol, 500 mol-%) were added under nitrogen and the mixture was stirred at rt overnight. The mixture was diluted with DCM (3 ml) and washed with water, 2N HCl, water and brine. Drying with $Na_2SO_4$ and evaporating the solvent afforded 86 mg of the product. Yield 80%.

$^1$H-NMR (DMSO-$d_6$): 1.03 (s, 3H), 1.10-2.90 (m, 21H), 2.37 (s, 3H), 3.73 (s, 3H), 7.11 (s, 1H), 7.61 (s, 1H), 11.90 (br s, 1H). MS m/z (TOF ES$^+$): 668 (M+1).

Compound 13

(13S,15R,E)-2,4-dibromo-17-(methoxyimino)-13-methyl-15-(3-((5-methylthiazol-2-yl)amino)-3-oxo-propyl)-7,8,9,11,12,13,14,15,16,17-decahydro-6H-cyclopenta[a]phenanthren-3-yl dihydrogen phosphate

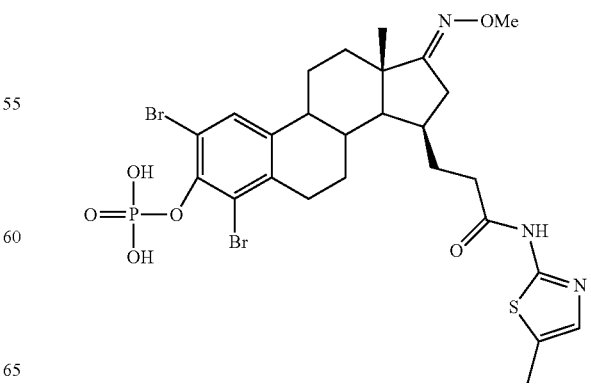

VIV-11 (150 mg, 0.24 mmol, 100 mol-%) was dissolved in dry THF (3 ml) and pyridine (1.5 ml). DMAP (29 mg, 0.24 mmol, 100 mol-%) was added. Phosphorus oxychloride (67 µl, 0.72 mmol, 300 mol-%) was added dropwise under nitrogen and the mixture was stirred overnight at rt. The mixture was cooled with an ice bath, cold water (2 ml) was added and the mixture was stirred at rt for 1.5 h. The solvents were evaporated and water (3 ml) was added. The mixture was left to precipitate over the weekend. The precipitate was filtered and washed with water, 2N HCl and water and dried in a vacuum oven in 50° C. for 3.5 h, affording 125 mg of the product.

$^{1}$H-NMR (DMSO-d$_6$): 1.02 (s, 3H), 1.10-2.90 (m, 21H), 3.73 (s, 3H), 7.11 (s, 1H), 7.51 (s, 1H), 11.89 (br s, 1H). $^{31}$P-NMR (DMSO-d6): −7.43. MS m/z (TOF ES$^+$): 706 (M+1).

Compound 14

(13S,15R,Z)-2,4-dibromo-17-(methoxyimino)-13-methyl-15-(3-((5-methylthiazol-2-yl)amino)-3-oxopropyl)-7,8,9,11,12,13,14,15,16,17-decahydro-6H-cyclopenta[a]phenanthren-3-yl dimethylglycinate

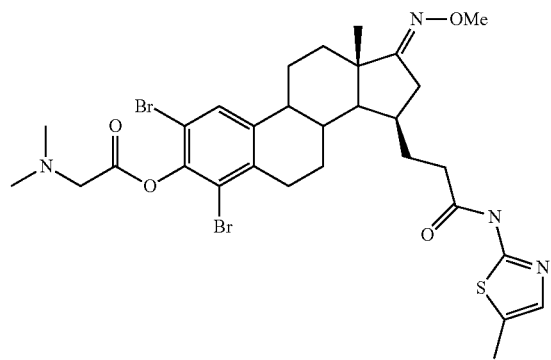 [SMILES: CO/N=C1\C[C@@H](CCC(=O)Nc2ncc(C)s2)C2C3CCc4c(cc(Br)c(OC(=O)CN(C)C)c4Br)C3CC[C@]12C]

VIV-11 (100 mg, 0.16 mmol, 100 mol-%) was suspended in dry DCM (2 ml). Pyridine (85 µl, 1.0 mmol, 650 mol-%), DMAP (6 mg, 0.05 mmol, 30 mol-%), N,N-dimethyl glycine (33 mg, 0.32 mmol, 200 mol-%) and DCC (132 mg, 0.64 mmol, 400 mol-%) were added and the mixture was stirred under nitrogen at 40° C. for 6 h and then left standing in rt overnight. Oxalic acid (58 mg, 0.64 mmol, 400 mol-%) dissolved in methanol (1 ml) was added to the mixture and stirred for 2 h. The mixture was filtered through Celite and evaporated, DCM was added to the residue and the mixture was again filtered through Celite twice. The precipitate was washed with DCM and EtOAc. The solvents were evaporated, DCM (5 ml) and water (5 ml) were added and stirred vigorously. The aqueous layer was washed with DCM, the organic layers were combined and washed with 0.1 N HCl, water and brine. Drying with Na2SO4 and evaporating the solvent afforded 73 mg of the product.

$^{1}$H-NMR (DMSO-d$_6$): 1.03 (s, 3H), 1.10-2.90 (m, 21H), 2.35 (s, 6H), 3.57 (br s, 2H), 3.73 (s, 3H), 7.10 (s, 1H), 7.61 (s, 1H), 11.90 (br s, 1H). MS m/z (TOF ES$^+$): 711 (M+1).

Compound 14a (13S,15R,Z)-2,4-dibromo-17-(methoxyimino)-13-methyl-15-(3-((5-methylthiazol-2-yl)amino)-3-oxopropyl)-7,8,9,11,12,13,14,15,16,17-decahydro-6H-cyclopenta[a]phenanthren-3-yl dimethylglycinate hydrochloride

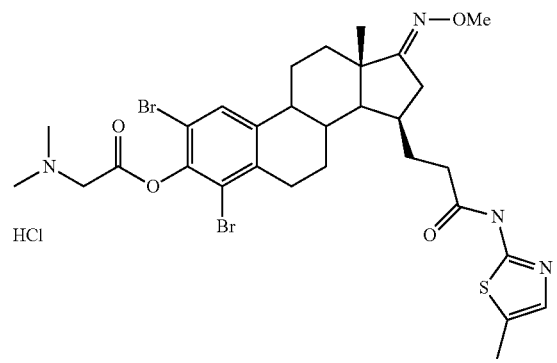 [SMILES: CO/N=C1\C[C@@H](CCC(=O)Nc2ncc(C)s2)C2C3CCc4c(cc(Br)c(OC(=O)CN(C)C)c4Br)C3CC[C@]12C ; Cl]

14 (56 mg, 0.08 mmol, 100 mol-%) was dissolved in dry EtOAc (1 ml). The mixture was filtered. Conc. HCl (24 µl) in EtOAc (0.2 ml) was added dropwise under nitrogen and the mixture was stirred in rt for 20 min. The solvents were evaporated and the residue was co-evaporated twice with toluene. The residue was triturated several times with EtOAc, filtered and washed again with EtOAc. The residue was dried in a vacuum oven in 50° C. for 2.5 h, affording 30 mg of the crude product. HPLC (280 nm) 54%. The product did not purify with HCl salt preparation.

$^{1}$H-NMR (DMSO-d$_6$): 1.03 (s, 3H), 1.10-2.90 (m, 20H), 2.94 (s, 6H), 3.73 (s, 3H), 4.80 (br s, 2H), 7.11 (s, 1H), 7.61 (s, 1H), 10.89 (br s, 1H), 11.90 (br s, 1H).

Compound 15

(13S,15R,E)-2-iodo-17-(methoxyimino)-13-methyl-15-(3-((5-methyl-thiazol-2-yl)amino)-3-oxopropyl)-7,8,9,11,12,13,14,15,16,17-decahydro-6H-cyclopenta[a]phenanthren-3-yl dimethylglycinate

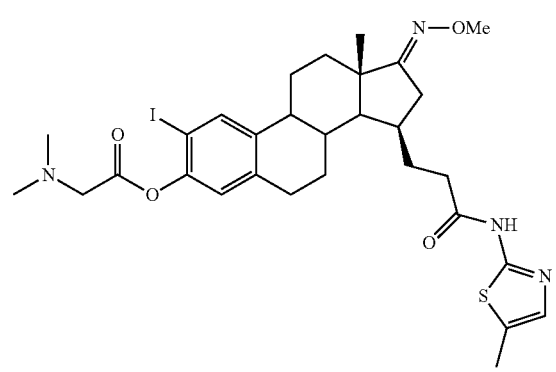 [SMILES: CO/N=C1\C[C@@H](CCC(=O)Nc2ncc(C)s2)C2C3CCc4cc(OC(=O)CN(C)C)c(I)cc4C3CC[C@]12C]

VIV-6 (100 mg, 0.19 mmol, 100 mol-%) was dissolved in DCM (2 ml) under nitrogen atmosphere. Pyridine (97 μl, 1.20 mmol, 650 mol-%), DMAP (7 mg, 0.06 mmol, 30 mol-%), N,N-dimethyl glycine (38 mg, 0.37 mmol, 200 mol-%) and DCC (153 mg, 0.74 mmol, 400 mol-%) were added to the reaction mixture. Reaction was stirred at 40° C. for 3 hours. Oxalic acid (67 mg, 0.74 mmol, 400 mol-%) dissolved in MeOH (0.5 ml) was added and stirring continued for 1 h 40 min. The precipitated DHU was filtered off. Organic layers were washed several times with dilute 0.1 N HCl-solution, followed by washing with water and finally with brine. The amount of the crude product was 110 mg.

$^1$H-NMR (DMSO-d$_6$): 1.04 (s, 3H), 1.10-2.90 (m, 21H), 2.34 (s, 6H), 3.49 (s, 2H), 3.73 (s, 3H), 6.93 (s, 1H), 7.10 (s, 1H), 7.67 (s, 1H), 11.87 (br s, 1H). MS m/z (TOF ES$^+$): 679 (M+1).

Compound 16

(13S,15R,E)-2-iodo-17-(methoxyimino)-13-methyl-15-(3-((5-methyl-thiazol-2-yl)amino)-3-oxopropyl)-7,8,9,11,12,13,14,15,16,17-decahydro-6H-cyclopenta[a]phenanthren-3-yl dihydrogen phosphate

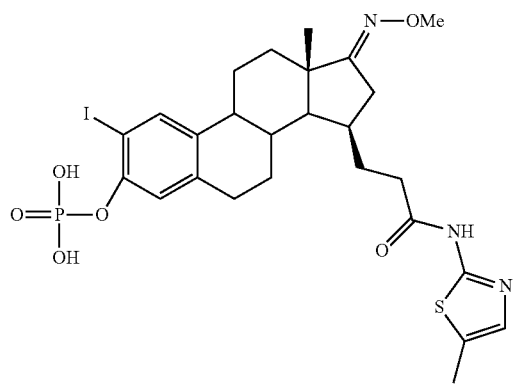 [SMILES: CO/N=C1\C[C@@H](CCC(=O)Nc2ncc(C)s2)C2C3CCc4cc(OP(=O)(O)O)c(I)cc4C3CC[C@]12C]

VIV-6 (50 mg, 0.08 mmol, 100 mol-%) was dissolved in dry THF (1 ml) under nitrogen atmosphere. Pyridine (0.5 ml), DMAP (10 mg, 0.08 mmol, 100 mol-%) and phosphorous oxychloride (24 μl, 0.25 mmol, 300 mol-%) were added. Reaction was stirred at rt for four hours. The solution was cooled and 1 ml of water was carefully added. Stirring was continued for one hour. THF was evaporated and water (2 ml) was added. Precipitated product was filtered and washed with water (2×2 ml), 2N HCl (3×2 ml) and water (3×2 ml). Amount of the product was 38 mg.

$^1$H-NMR (DMSO-d$_6$): 1.03 (s, 3H), 1.10-2.90 (m, 21H), 3.73 (s, 3H), 7.11 (s, 2H), 7.61 (s, 1H), 11.90 (br s, 1H). $^{31}$P-NMR (DMSO-d6): −6.75. MS m/z (TOF ES$^+$): 674 (M+1).

Compound 16a (13S,15R,E)-2-iodo-17-(methoxyimino)-13-methyl-15-(3-((5-methyl-thiazol-2-yl)amino)-3-oxopropyl)-7,8,9,11,12,13,14,15,16,17-decahydro-6H-cyclopenta[a]phenanthren-3-yl dihydrogen phosphate disodium salt

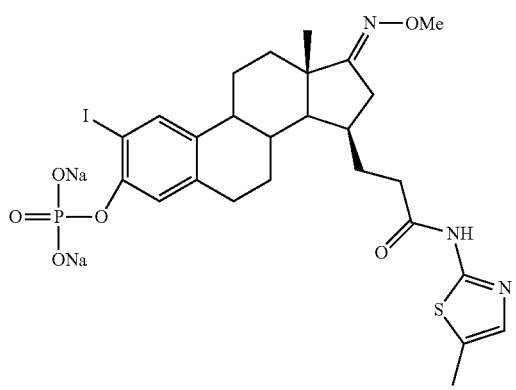

16 (22 mg, 0.03 mmol, 100 mol-%) was dissolved in abs. ethanol (0.2 ml) and then NaOH (4.2 mg, 350 mol-%) dissolved in abs. ethanol (0.1 ml) was added. After stirring for one hour, solvent was evaporated. The precipitate was washed with Et$_2$O (2×0.5 ml) and EtzO:EtOH (1:1) (2×0.5 ml). The amount of the phosphate disodium salt was 17 mg.

$^1$H-NMR (MeOH-d$_4$+D20): 1.12 (s, 3H), 1.10-2.90 (m, 21H), 3.79 (s, 3H), 6.97 (s, 1H), 7.50-7.53 (m, 2H). $^{31}$P-NMR (MeOH-d$_4$+D20): 0.25.

Compound 17

(13S,15R,E)-17-(methoxyimino)-13-methyl-15-(3-((5-methylthiazol-2-yl)amino)-3-oxopropyl)-4-nitro-7,8,9,11,12,13,14,15,16,17-decahydro-6H-cyclopenta[a]phenanthren-3-yl dihydrogen phosphate

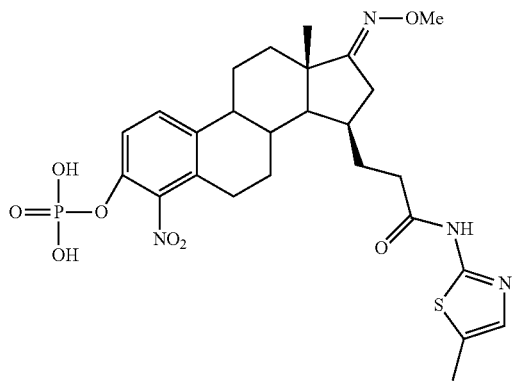

The compound 17 was prepared by the same method as used for 16. Yield 67%.

$^1$H-NMR (DMSO-d$_6$): 1.04 (s, 3H), 1.10-2.90 (m, 21H), 3.73 (s, 3H), 7.10 (s, 1H), 7.40-7.47 (m, 2H), 11.89 (br s, 1H). $^{31}$P-NMR (DMSO-d6): −6.72. MS m/z (TOF ES$^+$): 593 (M+1).

Compound 17a

Disodium (13S,15R,E)-17-(methoxyimino)-13-methyl-15-(3-((5-methylthiazol-2-yl)amino)-3-oxopropyl)-4-nitro-7,8,9,11,12,13,14,15,16,17-decahydro-6H-cyclopenta[a]phenanthren-3-yl dihydrogen phosphate

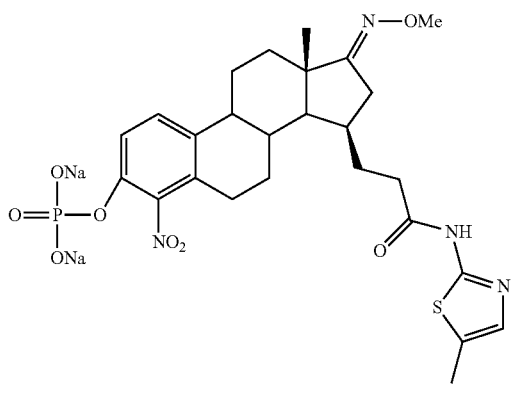

The compound 17a was prepared by the same method as used for 16a. $^1$H-NMR (MeOH-d$_4$): 1.12 (s, 3H), 1.10-2.90 (m, 21H), 3.79 (s, 3H), 6.97 (s, 1H), 7.50-7.53 (m, 2H). $^{31}$P-NMR (DMSO-d6): 0.35.

Compound 18

(13S,15R,E)-17-(hydroxyimino)-13-methyl-15-(3-((5-methylthiazol-2-yl)amino)-3-oxopropyl)-4-nitro-7,8,9,11,12,13,14,15,16,17-decahydro-6H-cyclopenta[a]phenanthren-3-yl dihydrogen phosphate

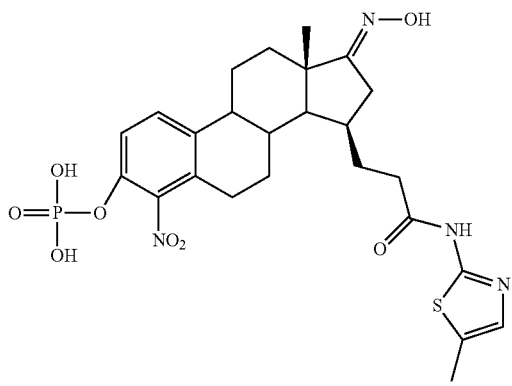 [SMILES: Cc1cnc(NC(=O)CC[C@@H]2C/C(=N\O)[C@@]3(C)CCC4c5ccc(OP(=O)(O)O)c([N+](=O)[O-])c5CCC4C23)s1]

VIV-24 (90 mg, 0.160 mmol, 100 mol-%) was suspended in abs. ethanol (5 ml). Hydroxylamine hydrochloride (56 mg, 0.798 mmol, 500 mol-%) was added. Pyridine (155 μl, 1.916 mmol, 1200 mol-%) was added under nitrogen. The mixture was stirred at rt for 3 h and at 50-60° C. for 2 h. Solvents were evaporated and crude product triturated with EtOAc:0.25 HCl (10 ml:10 ml). Product was filtered and washed with 0.25 M HCl and water. Yield 84 mg, 92%.

$^1$H-NMR (DMSO-d$_6$): 1.02 (s, 3H), 1.10-2.90 (m, 21H), 7.10 (s, 1H), 7.39-7.49 (m, 2H), 10.18 (br s, 1H), 11.91 (br s, 1H). $^{31}$P-NMR (DMSO-d6): −6.87. MS m/z (TOF ES$^+$): 579 (M+1).

Compound 19

(13S,15R,E)-4-bromo-17-(hydroxyimino)-13-methyl-15-(3-((5-methylthiazol-2-yl)amino)-3-oxopropyl)-7,8,9,11,12,13,14,15,16,17-decahydro-6H-cyclopenta[a]phenanthren-3-yl dihydrogen phosphate

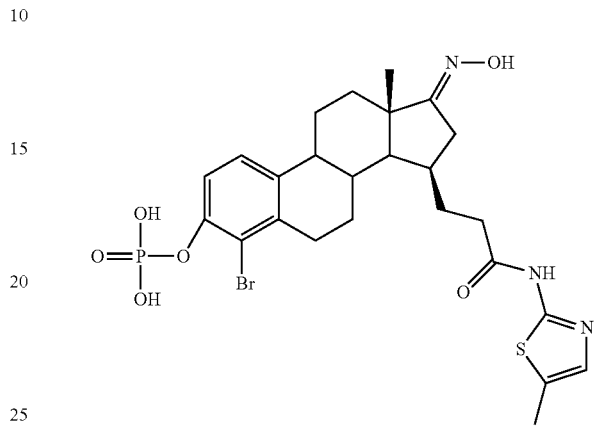

The compound 19 was prepared by the same method as used for 21 using VIII-28 as starting material. Reaction time was 3 h and work-up was modi-fied. Water and 2 N HCl were added and precipitated product was filtered and washed with water and EtOAc. Yield 66 mg, 64%.

$^1$H-NMR (DMSO-d$_6$): 1.01 (s, 3H), 1.10-2.90 (m, 21H), 7.11 (s, 1H), 7.25-7.29 (m, 2H), 10.17 (br s, 1H), 11.92 (br s, 1H). $^{31}$P-NMR (DMSO-d6): −6.77.

Compound 19a

Sodium (13S,15R,E)-4-bromo-17-(hydroxyimino)-13-methyl-15-(3-((5-methylthiazol-2-yl)amino)-3-oxopropyl)-7,8,9,11,12,13,14,15,16,17-decahydro-6H-cyclopenta[a]phenanthren-3-yl phosphate

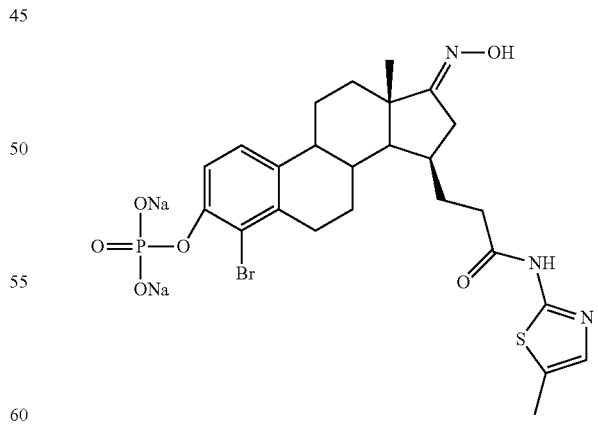

The compound 19a was prepared by the same method as used for 16a. The reaction time was 2 h.

$^1$H-NMR (MeOH-d$_4$): 1.10 (s, 3H), 1.10-3.10 (m, 21H), 7.08 (s, 1H), 7.15-7.20 (d, 1H), 7.56-7.60 (d, 1H). $^{31}$P-NMR (DMSO-d6): 0.06. MS m/z (TOF ES$^+$): 656/658.

Compound 20

(13S,15R,E)-2,4-diiodo-17-(methoxyimino)-13-methyl-15-(3-((5-methylthiazol-2-yl)amino)-3-oxo-propyl)-7,8,9,11,12,13,14,15,16,17-decahydro-6H-cyclopenta[a]phenanthren-3-yl dimethylglycinate

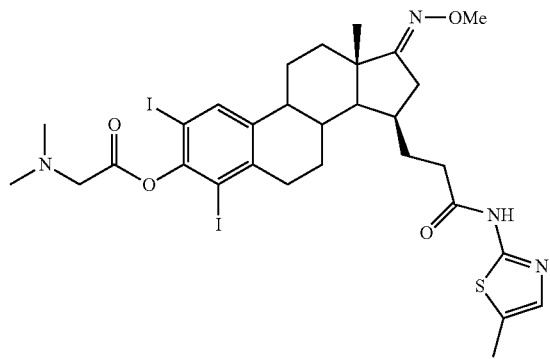 [SMILES: CO/N=C1\C[C@@H](CCC(=O)Nc2ncc(C)s2)C2C3CCc4c(cc(I)c(OC(=O)CN(C)C)c4I)C3CC[C@]12C]

VIV-8 (100 mg, 0.139 mmol, 100 mol-%) was dissolved in dry DCM (2 ml) under nitrogen atmosphere. Pyridine (73 µl, 0.904 mmol, 650 mol-%), DMAP (5 mg, 0.058 mmol, 30 mol-%), N,N-dimethyl glycine (29 mg, 0.278 mmol, 200 mol-%) and DCC (114 mg, 0.556 mmol, 400 mol-%) were added to the reaction mixture. Reaction was stirred at 40° C. for 2 h and left to stand overnight at rt. Oxalic acid (50 mg, 0.556 mmol, 400 mol-%) dissolved in MeOH (0.2 ml) was added and stirring continued for 1.5 h. Solvents were evaporated and residue dissolved in DCM. The precipitated dicyclohexylurea (DCU) was filtered off. Organic layers were washed with 0.1 N HCl (3×5 ml), water (3×10 ml) and brine (2×10 ml). The amount of the crude product was 120 mg.

$^1$H-NMR (DMSO-$d_6$): 1.03 (s, 3H), 1.10-2.90 (m, 21H), 2.38 (s, 6H), 3.55 (s, 2H), 3.73 (s, 3H), 7.11 (s, 1H), 7.75 (s, 1H), 11.90 (br s, 1H). MS m/z (TOF ES$^+$): 805 (M+1).

Compound 21

(13S,15R,E)-2,4-dibromo-17-(hydroxyimino)-13-methyl-15-(3-((5-methylthiazol-2-yl)amino)-3-oxo-propyl)-7,8,9,11,12,13,14,15,16,17-decahydro-6H-cyclopenta[a]phenanthren-3-yl dihydrogen phosphate

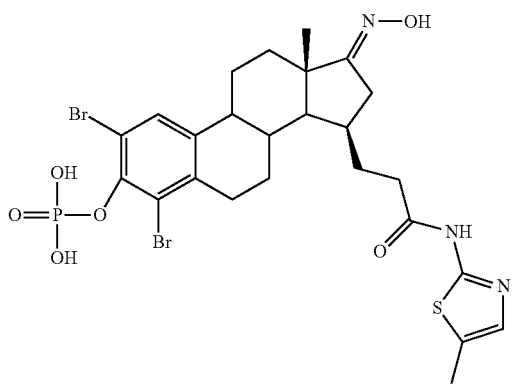 [SMILES: Cc1cnc(NC(=O)CC[C@@H]2C/C(=N\O)[C@@]3(C)CCC4c5cc(Br)c(OP(=O)(O)O)c(Br)c5CCC4C23)s1]

VIII-26 (90 mg, 0.13 mmol, 100 mol-%) was suspended in ethanol (5 ml). Hydroxylamine hydrochloride (46 mg, 0.67 mmol, 500 mol-%) was added. Pyridine (130 µl, 1.60 mmol, 1200 mol-%) was added under nitrogen. The mixture was stirred at rt for 5 h. Additional amounts of reagents (50% of the original amounts) were added and the stirring was continued at rt overnight. The mixture was heated to 40° C. and stirred for 3.5 h, then heated to 60° C. and stirred for 1.5 h and left to stand over the weekend at rt. The solvent was evaporated and EtOAc (10 ml) and water (15 ml) were added. The precipitate was filtered, washed with water and EtOAc. After drying and combining the precipitate with the additional amount of the product received from EtOAc-phase, the yield of the product was 38 mg.

$^1$H-NMR (DMSO-$d_6$): 1.01 (s, 3H), 1.10-2.90 (m, 24H), 7.11 (s, 1H), 7.50 (s, 1H), 10.20 (br s, 1H), 11.92 (br s, 1H). $^{31}$P-NMR (DMSO-d6): −7.35. MS m/z (TOF ES$^+$): 692 (M+1).

Compound 22

(13S,15R,E)-2,4-diiodo-17-(methoxyimino)-13-methyl-15-(3-((5-methylthiazol-2-yl)amino)-3-oxo-propyl)-7,8,9,11,12,13,14,15,16,17-decahydro-6H-cyclopenta[a]phenanthren-3-yl dihydrogen phosphate

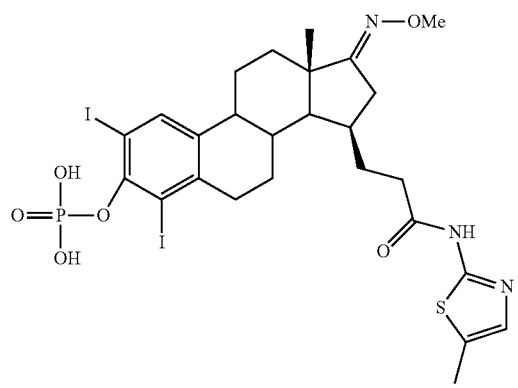 [SMILES: CO/N=C1\C[C@@H](CCC(=O)Nc2ncc(C)s2)C2C3CCc4c(cc(I)c(OP(=O)(O)O)c4I)C3CC[C@]12C]

The compound 22 was prepared by the same method as used for 18 in 4 hours reaction time. Yield 78 mg, 70%.

$^1$H-NMR (DMSO-$d_6$): 1.01 (s, 3H), 1.10-3.00 (m, 21H), 3.72 (s, 3H), 7.11 (s, 1H), 7.68 (s, 1H), 11.91 (br s, 1H). $^{31}$P-NMR (DMSO-d6): −7.55. MS m/z (TOF ES$^+$): 800 (M+1).

Pharmacological Tests

The following tests are provided to demonstrate the present invention in illustrative way and should not be considered as limiting in the scope of invention. Further, the concentrations of the compounds in the assays are exemplary and should not be taken as limiting. A person skilled in the art may define pharmaceutically relevant concentrations with method known in the art.

Inhibition of 17β-Hydroxysteroid Dehydrogenase Type 1 Enzyme

17β-HSD1 production and isolation: Recombinant baculovirus was generated by the "Bac to Bac Expression System" (Invitrogen). Recombinant bacmid was transfected to Sd9 insect cells using "Cellfectin Reagent" (Invitrogen). 60 h later cells were harvested; the microsomal fraction was isolated as described by Puranen, T. J., Poutanen, M. H., Peltoketo, H. E., Vihko, P. T. and Vihko, R. K. (1994)

Site-directed mutagenesis of the putative active site of human 17 β-hydroxysteroid dehydrogenase type 1. Biochem. J. 304: 289-293. Aliquots were stored frozen until determination of enzymatic activity.

Assay—Inhibition of recombinant human 17β-HSD1: Protein homogenate (0.1 µg/ml) was incubated in 20 mM KH2PO4 pH 7.4 with 30 nM estrone (including 800 000 cpm/ml of $^3$H-estrone) and 1 mM NADPH for 30 min at RT, in the presence of the potential inhibitor at concentrations 1 µM or 0.1 µM. Inhibitor stock solutions were prepared in DMSO. Final concentration of DMSO was adjusted to 1% in all samples. The enzyme reaction was stopped by addition of 10% trichloroacetic acid (final concentration). Samples were centrifuged in a microtiter plate at 4000 rpm for 10 min. Supernatants were applied to reverse phase HPLC on a Waters Symmetry C18 column, equipped with a Waters Sentry Guard column. Isocratic HPLC runs were performed at RT at a flow rate of 1 ml/min in acetonitrile:water 48:52 as running solvent. Radioactivity was monitored in the eluate by a Packard Flow Scintillation Analyzer. Total radioactivity for estrone and estradiol were determined in each sample and percent conversion of estrone to estradiol was calculated according to the following formula:

$$\% \text{ conversion} = 100 \times \frac{\{(cpm \text{ estradiol in sample with inhibitor})/[(cpm \text{ estrone in sample with inhibitor}) + (cpm \text{ estradiol in sample with inhibitor})]\}}{[(cpm \text{ estradiol in sample without inhibitor})/[(cpm \text{ estrone in sample without inhibitor}) + (cpm \text{ estradiol in sample without inhibitor})]\}}.$$

Percent inhibition was calculated flowingly: % inhibition=100–% conversion

The values % inhibition were determined for the parent compounds and the results are summarized in Table 3.

Inhibition of the 17β-Hydroxysteroid Dehydrogenase Type 2 Enzyme

17β-HSD2 production and isolation: Similarly to 17β-HSD1 the Recombinant baculovirus was generated by the "Bac to Bac Expression System" (Invitrogen). Recombinant bacmid was transfected to Sd9 insect cells using "Cellfectin Reagent" (Invitrogen). 60 h later cells were harvested and supernatant were fractionated by the following protocol:

- cells were dissolved into 40 ml of A-buffer (40 mM TRIS, pH8.0, 20% glycerol, 20 µM NAD, 0.4 mM PMSF, 150 mM NaCl, 0.5% dodecyl-β-maltoside+protease inhibitor cocktail)
- cells were sonicated
- lysate was incubated on ice for 15 min
- lysate was centrifuged 5000 rpm 15 min, +4° C.
- centrifugation of the supernatant 180 000 g 30 min, +4° C.
- pellet was dissolved into 8 ml of A-buffer
- not resuspended material was removed by centrifugation 5000 rpm 15 min, +4° C.
- the clear supernatant was divided into 100 µl aliquots and were stored frozen until determination of enzymatic activity.

The amount of 17β-HSD2 was analysed by immunoblotting and total protein concentration of each extract batch was determined.

Assay—Inhibition of recombinant human 17β-HSD2: Protein homogenate (4 µg/ml) was incubated in 20 mM KH2PO4 pH 8.5 with 50 nM estradiol (including 800 000 cpm/ml of $^3$H-estradiol) and 1 mM NADH for 30 min at RT, in the presence of the potential inhibitor at concentrations 1 µM or 0.1 µM. Inhibitor stock solutions were prepared in DMSO. Final concentration of DMSO was adjusted to 1% in all samples. The enzyme reaction was stopped by addition of 10% trichloroacetic acid (final concentration). Samples were centrifuged in a microtiter plate at 4000 rpm for 10 min. Supernatants were applied to reverse phase HPLC on a Waters Symmetry C18 column, equipped with a Waters Sentry Guard column. Isocratic HPLC runs were performed at RT at a flow rate of1 ml/min in acetonitrile:water 48:52 as running solvent. Radioactivity was monitored in the eluate by a Packard Flow Scintillation Analyzer. Total radioactivity for estrone and estradiol were determined in each sample and percent conversion of estradiol to estrone was calculated according to the following formula:

$$\% \text{ conversion} = 100 \times \frac{\{(cpm \text{ estrone in sample with inhibitor})/[(cpm \text{ estradiol in sample with inhibitor}) + (cpm \text{ estrone in sample with inhibitor})]\}}{[(cpm \text{ estrone in sample without inhibitor})/[(cpm \text{ estradiol in sample without inhibitor}) + (cpm \text{ estrone in sample without inhibitor})]\}}.$$

Percent inhibition was calculated flowingly: % inhibition=100–% conversion

The values % inhibition were determined for the active entities and the results are summarized in Table 3.

TABLE 3

Pharmacological activity of the active entities

| # | 17β-HDS1 Inhibition % at 1 µM | 17β-HSD2 Inhibition % at 1 µM |
|---|---|---|
| VIV-1 | 95 | 4 |
| VIV-2 | 64 | 3 |
| VIV-4 | 90 | 16 |
| VIV-6 | 90 | 0 |
| VIV-7 | 81 | 0 |
| VIV-8 | 61 | 2 |
| VIV-9 | 81 | 1 |
| VIV-10 | 78 | 6 |
| VIV-11 | 78 | 3 |
| VIV-12 | 95 | 3 |
| VIV-13 | 86 | 5 |
| VIV-15 | 94 | 5 |
| VIV-16 | 90 | 7 |
| VIV-17 | 83 | 2 |
| VIV-18 | 55 | 1 |
| VIV-19 | 93 | 2 |
| VIV-20 | 73 | 0 |
| VIV-22 | 81 | 4 |
| VIV-23 | 95 | 6 |
| VIV-24 | 96 | 33 |
| VIV-25 | 77 | 25 |
| VIV-26 | 89 | 15 |
| VIV-27 | 98 | 28 |
| VIV-28 | 98 | 21 |
| VIV-29 | 98 | 21 |
| VIV-30 | 87 | 23 |
| VIV-31 | 97 | 14 |

Estrogen Receptor Binding Assay

The binding affinity of the parent compounds to the estrogen receptor a (ERα) may be determined according to the in vitro ER binding assay described by Koffmann et al REF. Alternatively, an estrogen receptor binding assay may be performed according to international patent application WO2000/07996.

Estrogen Receptor Transactivation Assays

The parent compounds showing binding affinity towards the estrogen receptor may be further tested with regard to their individual estrogenic or anti-estrogenic potential (Agonistic or antagonistic binding to the ERα or ERβ. The determination of the estrogen receptor antagonistic activity may be performed according to an in vitro assay system using the MMTV-ERE-LUC reporter system for example described in US patent application US2003/0170292.

Metabolic Stability Assay

The in vitro metabolic stability of the parent compounds was determined for exemplified compounds using human liver microsome and homogenate incubations. The incubation time points used with or without appropriate cofactors were 0 min and 60 min. Samples were collected at both time points and substrates were detected using LC/PDA/TOF-MS. In vitro metabolic stability (% remaining after 60 min in human liver homogenate or microsomes) of the compounds were calculated and the results are summarized in Table 4.

TABLE 4

| # | Metabolic stability |
|---|---|
|   | In vitro metabolic stability, % remaining after 60 min |
| VII | 13 |
| VIV-1 | 73 |
| VIV-9 | 34 |
| VIV-12 | 94 |
| VIV-15 | 92 |
| VIV-16 | 68 |

Enzymatic Hydrolysis of Compounds of Invention

Hydrolysis of the compounds according to Examples 1a, 3b, 5a, and 7 to their parent compound VIV was tested. The unit amounts of alkaline phospha-tase type VIIS from bovine intestinal mucosa were used as defined by a supplier (SigmaAldrich). An appropriate amount of the compound (final concentration typically 50 μM) was dissolved in preheated buffer solution (pH 7.4) and the solutions were placed in a thermostatically controlled water bath at 37° C. The enzymatic reaction was started by adding enzyme to the solution. In blank solutions, enzyme was replaced with the same volume of water to ensure that the hydrolysis was clearly enzymatic. At predetermined time intervals, 200 μl samples were removed and 200 μl icecold acetonitrile was added to each sample to stop the enzymatic hydrolysis. The samples were kept on ice, centrifuged for 10 min at 14000 rpm, and the supernatant was analyzed by the HPLC. Pseudo-first order halflives (t1/2) for the hydrolysis of the compounds were calculated from the slope of the linear portion of the plotted logarithm of the remaining compound versus time.

All tested compounds hydrolyzed to their corresponding parent molecules within about 3 to 8 min.

Aqueous Solubility Test

The aqueous solubility of the parent compound VIV-1 and the compound of Examples 1a and 3 was determined at rt in an appropriate buffer solution (0.16 M phosphate buffer or 0.05 mM Tris-HCl buffer at pH 7.4, 0.05 M acetate buffer at pH 5.0, 50 mM (ionic strength 0.15) HCl buffer at pH 1.0). The pH of the mixtures was held constant during the study. Excess amounts or a known amount of each component are added to 1 or 0.5 ml of buffer solution and the mixtures were stirred at rt for 48 hours or less, filtered (0.45 μm Millipore) and analyzed by HPLC. The results are presented in Table 5.

TABLE 5

| Solubility data | |
|---|---|
| Compound | Aqueous solubility, buffer at pH 7.4 |
| VIV-1 | under quantification limit (0.52 μg/ml) |
| 1a | over 35 mg/ml |
| 3 | 2.37 μg/ml |

It will be seen from Table 5 that Examples 1a and 3 exhibited improved aqueous solubility.

Determination of Bioavailability

This study was performed in order to determine bioavailability of the present compounds in vivo. All animal experiments are performed in accordance with standards of ethical conduct and appropriate institutional animal care and use policies.

The pharmacokinetic studies of the compounds of the invention were assessed in Cynomolgus monkeys. The study compounds were administrated orally at a dose level corresponding to 10 mg/kg of parent drug. The common aqueous formulation, 0.5% Carboxymethyl cellulose in water, was used as a vehicle. The blood samples were obtained by direct venipuncture at pre-dose, and ten sequential time points after oral administration.

The quantitative bioanalysis of plasma samples were performed in accordance with the guidance Bioanalytical Method Validation (FDA, 2001) and the Guideline on Bioanalytical Method Validation (European Medicines Agency, 2011). Analytical method was optimized for suitable chromatographic (peak shape, retention) and mass spectrometric (ionization efficiency) properties.

A non-compartmental pharmacokinetic analysis was carried out with individual plasma concentration-time curves using WinNonlin® Professional Version 6.3 (Pharsight Corporation):

$C_{max}$ (maximum observed concentration) and tmax (time taken to reach maximum observed concentration) values The area under the concentration-time curve from 0 to the last measurable concentration ($AUC_t$) was calculated using the linear-log trapezoidal rule.

The obtained $C_{max}$ and $AUC_t$ values of study compounds are shown in the Table 6.

TABLE 6

| Compound | Cmax (ng/mL) | AUCt (ng · h/mL) |
|---|---|---|
| 1a | 286 | 3170 |
| 3b | 304 | 4037 |
| 5a | 408 | 4583 |
| 7 | 433 | 4773 |

It can be seen from Table 6 that that all tested compounds of the invention provide good bioavailability.

Utility of the Invention

Compounds of the invention when metabolized to their parent compounds and/or as such show selective inhibitory potential of the 17β-HSD1 enzyme and little or no inhibitory activity to the 17β-HSD2 enzyme and therefor, and may be useful for the treatment of a steroid hormone dependent malign or benign disease or disorder, in particular for treatment and prevention of several estrogen dependent diseases and disorders. Further, compounds of the present invention may be useful for the treatment of diseases and disorders associated with increased levels of estradiol and which may be prevented, treated, and/or ameliorated by an inhibitor of 17β-HSD1 enzyme.

Examples of inflammatory diseases and conditions include, but are not limited to, breast cancer, prostate carcinoma, ovarian cancer, uterine cancer, endometrial cancer, endometrial hyperplasia, endometriosis, uterine fibroids, uterine leiomyoma, adenomyosis, dysmenorrhea, menorrhagia, metrorrhagia, prostadynia, benign prostatic hyperplasia, urinary dysfunction, polycystic ovarian syndrome, lower urinary tract syndrome, multiple sclerosis, obesity, rheumatoid arthritis, colon cancer, tissue wounds, skin wrinkles and cataracts.

"Treatment or prevention" as used herein includes prophylaxis, or prevention of, as well as lowering the individual's risk of falling ill with the named disorder or condition, or alleviation, amelioration, elimination, or cure of the said disorder once it has been established.

Thus the compounds of the present invention may be useful as active ingredients in pharmaceutical composition for treatment or prevention of a disease or disorder requiring the inhibition of 17β-HSD enzyme.

Compounds of the present invention may be administered in an effective amount within the dosage range of about 0.1 g/kg to about 300 mg/kg, preferably between 1.0 g/kg to 10 mg/kg body weight. Compounds of the present invention may be administered in a single daily dose, or the total daily dosage may be administered in divided doses of two, three or four times daily.

"An effective amount" refers to an amount of a compound that confers a therapeutic effect on the treated subject. The therapeutic effect may be objective (i.e. measurable by some test or marker) or subjective (i.e. subject gives an indication of or feels an effect). Such treatment need not necessarily completely ameliorate the condition of disease. Further, such treatment or prevention can be used in conjunction with other traditional treatments for reducing the condition known to those skilled in the art.

Compounds of the invention are most preferably used alone or in other active ingredients. Compounds of the invention may be administered by various routes, for example, parenteral, subcutaneous, intravenous, intraarticular, intrathecal, intramuscular, intraperitoneal, and by intradermal injections, and via transdermal, rectal, buccal, oromucosal, nasal, ocular routes and via inhalation and via implant. The pharmaceutical compositions including the compound of the present invention as active ingredients may further include pharmaceutically acceptable additives.

Compounds may be formulated into a suitable composition; suitable administration forms include, for example, solutions, dispersions, suspensions, powders, capsules, tablet, pills, controlled release capsules, controlled release tablets and controlled release pills. In addition to the pharmacologically active compounds, the pharmaceutical compositions of the compounds can contain suitable pharmaceutically acceptable carriers comprising excipients and auxiliaries that facilitate processing of the active compounds into preparations that can be used pharmaceutically.

Furthermore, compounds of formula (I) can be used as synthesis in-termediates for the preparation of other compounds, in particular of other pharmaceutically active ingredients, which are obtainable from compounds of formula (I), for example by introduction of substituents or modification of functional groups.

It will be obvious to a person skilled in the art that, as the technology advances, the inventive concept can be implemented in various ways. The invention and its embodiments are not limited to the examples described above but may vary within the scope of the claims.

The invention claimed is:

1. A compound having formula (I)

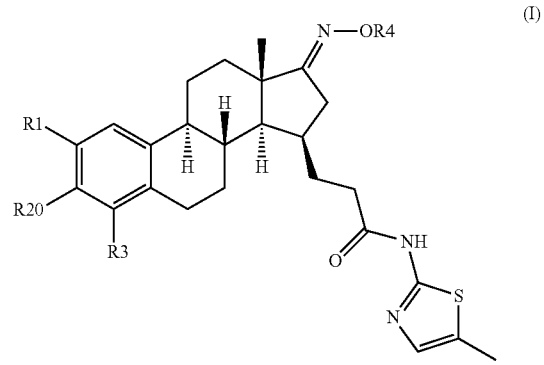

wherein

R1 and R3 are each independently selected from the group consisting of H, halogen, $C_{1-3}$-haloalkyl, $C_{1-3}$-perhaloalkyl, CN, $NO_2$, $N(R')_2$, $(CH_2)_nN(R')_2$, OR', $(CH_2)_nOR'$;

R2 is selected from the group consisting of $SO_2OH$, $SO_2R''$, $SO_2N(R')_2$, $(CH_2O)_mPO(OR')_2$, COOR''', C(O)N(R')_2$, $C(O)(CH_2)_nN(R')_2$, $C(O)CH_2NR'C(O)R'$, $C(O)CH_2NR'C(O)OR''$ and $C(O)R'''$; and R4 is H or $C_{1-3}$-alkyl;

whereby

R' is H, $C_{1-6}$ alkyl, $C_{1-3}$-haloalkyl, or $C_{1-3}$-perhaloalkyl, or when part of any $N(R')_2$ both R's together with the nitrogen they are attached to may form a 5 to 6 membered aliphatic or aromatic heterocyclic ring comprising 1 or 2 heteroatoms each independently selected from N and O or a charged $N(R')_3^+$ group wherein R' is as defined above;

R'' is $C_{1-6}$-alkyl, $C_{1-3}$-haloalkyl, or $C_{1-3}$-perhaloalkyl;

R''' is $C_{1-6}$-alkyl, $C_{2-6}$-alkenyl, —$(CH_2)_n$—$C_{3-6}$-cycloalkyl, an optionally substituted phenyl, or a 5 to 6 membered aliphatic or aromatic heterocyclic ring comprising 1 or 2 heteroatoms each independently selected from N and O, optionally substituted at any N atom by C(O)R' wherein R' is as defined above;

m is 0, 1 or 2; and n is 1 or 2;

provided that when R1 is H and R4 is methyl, R2 is not C(O)Me, $C(O)CH_2NMe_2$, $S(O)_2NH_2$, $S(O)_2NMe_2$, or $S(O)_2Me$.

2. A compound of formula (I) as claimed in claim 1, wherein R1 and R3 are each independently selected from H, halogen, $C_{1-3}$-haloalkyl, $C_{1-3}$-perhaloalkyl, CN, and $NO_2$, preferably from H, halogen, $NO_2$, and CN.

3. A compound of formula (I) as claimed in claim 1, wherein R1 and R3 are each independently H or halogen.

4. A compound of formula (I) as claimed in in claim 1, wherein R1 and R3 are both H.

5. A compound of formula (I) as claimed in claim 1, wherein R4 is methyl.

6. A compound of formula (I) as claimed in claim 1, wherein R2 is selected from the group consisting of $CH_2O)_m PO(OR')_2$, $C(O)(CH_2)_nN(R')_2$, $C(O)CH_2NR'C(O)R'$, and $C(O)CH_2NR'C(O)OR''$.

7. A compound of formula (I) as claimed in claim 1, wherein R2 is $C(O)(CH_2)_nN(R')_2$.

8. A compound of formula (I) as claimed claim 1, wherein R2 is $(CH_2O)_mPO(OR')_2$, wherein R' is H, $C_{1-6}$-alkyl, $C_{1-3}$-haloalkyl, or $C_{1-3}$-perhaloalkyl, and m is 0 or 1.

9. A compound of formula (I) as claimed in claim 8, wherein m is 1.

10. A compound of formula (I) selected from the group consisting of:

Compound 1 Phosphoric acid mono-{(13S,15R)-17-[(E)-methoxyimino]-13-methyl-15-[2-(5-methylthiazol-2-ylcarbamoyl)ethyl-7,8,9,11,12,13,14,15,16,17-decahydro-6H-cyclopenta[a]phenanthren-3-yl} ester;

Compound 2 tert-Butoxycarbonylamino-acetic acid (13S, 15R)-13-methyl-17[(E)-methoxyimino]-15-[2-(5-methyl-thiazol-2-ylcarbamoyl)-ethyl]-7,8,9,11,12,13, 14,15,16,17-decahydro-6H-cyclopenta[a]phenanthren-3-yl ester;

Compound 3 Aminoacetic acid (13S, 15R)-13-methyl-17 [(E)-meth-oxyimino]-15-[2-(5-methyl-thiazol-2-ylcarbamoyl)-ethyl]-7,8,9,11,12,13,14,15,16,17-decahydro-6H-cyclopenta[a]phenanthren-3-yl ester;

Compound 4 Tert-Butoxycarbonyl-methylamino-acetic acid (13S,15R)-13-methyl-17[(E)-methoxyimino]-15 [2-(5-methyl-thiazol-2-ylcarbamoyl)-ethyl]-7,8,9,11, 12,13,14,15,16,17-decahydro-6H-cyclopenta[a] phenanthren-3-yl ester;

Compound 5 Methylamino-acetic acid (13S,15R)-13-methyl-17[(E)-methoxyimino]-15-[2-(5-methyl-thiazol-2-ylcarbamoyl)-ethyl]-7,8,9,11,12,13,14,15,16, 17-decahydro-6H-cyclopenta[a]phenanthren-3-yl ester;

Compound 6 Morpholin-4-yl-acetic acid (13S,15R)-13-methyl-17[(E)-methoxyimino]-15-[2-(5-methyl-thiazol-2-ylcarbamoyl)-ethyl]-7,8,9,11,12,13,14,15,16, 17-decahydro-6H-cyclopenta[a]phenanthren-3-yl ester;

Compound 7 1-(tert-butyl)2-(13S,15R,E)-17-(methoxyimino)-13-methyl-15-(3-((5-methylthiazol-2-yl) amino)-3-oxopropyl)-7,8,9,11,12,13,14,15,16,17-decahydro-6H-cyclopenta[a]phenanthren-3-yl) pyrrolidine-1,2-dicarboxylate;

Compound 8 (13S,15R,E)-17-(methoxyimino)-13-methyl-15-(3-((5-methylthiazol-2-yl)amino)-3-oxopropyl)-7,8,9,11,12,13,14,15,16,17-decahydro-6H-cyclopenta[a]phenanthren-3-yl prolinate;

Compound 9 di-tert-butyl((((13S,15R,E)-17-(methoxyimino)-13-methyl-15-(3-((5-methylthiazol-2-yl) amino)-3-oxopropyl)-7,8,9,11,12,13,14,15,16,17-decahydro-6H-cyclopenta[a]phenanthren-3-yl)oxy)methyl) phosphate;

Compound 10 (((13S,15R,E)-17-(methoxyimino)-13-methyl-15-(3-((5-methylthiazol-2-yl)amino)-3-oxopropyl)-7,8,9,11,12,13,14,15,16,17-decahydro-6H-cyclopenta[a]phenanthren-3-yl)oxy)methyl dihydrogen phosphate;

Compound 11 (13S,15R,E)-2,4-dibromo-17-(hydroxyimino)-13-methyl-15-(3-((5-methylthiazol-2-yl) amino)-3-oxopropyl)-7,8,9,11,12,13,14,15,16,17-decahydro-6H-cyclopenta[a]phenanthren-3-yl acetate;

Compound 12 (13S,15R,E)-2,4-dibromo-17-(methoxyimino)-13-methyl-15-(3-((5-methylthiazol-2-yl) amino)-3-oxopropyl)-7,8,9,11,12,13,14,15,16,17-decahydro-6H-cyclopenta[a]phenanthren-3-yldihydrogen phosphate;

Compound 13 (13S,15R,Z)-2,4-dibromo-17-(methoxyimino)-13-methyl-15-(3-((5-methylthiazol-2-yl) amino)-3-oxopropyl)-7,8,9,11,12,13,14,15,16,17-decahydro-6H-cyclopenta[a]phenanthren-3-yl dimethylglycinate;

Compound 14 (13S,15R,E)-2-iodo-17-(methoxyimino)-13-methyl-15-(3-((5-methylthiazol-2-yl)amino)-3-oxopropyl)-7,8,9,11,12,13,14,15,16,17-decahydro-6H-cyclopenta[a]phenanthren-3-yl dimethylglycinate;

Compound 15 (13S,15R,E)-2-iodo-17-(methoxyimino)-13-methyl-15-(3-((5-methylthiazol-2-yl)amino)-3-oxopropyl)-7,8,9,11,12,13,14,15,16,17-decahydro-6H-cyclopenta[a]phenanthren-3-yl dimethylglycinate;

Compound 16 (13S,15R,E)-2-iodo-17-(methoxyimino)-13-methyl-15-(3-((5-methylthiazol-2-yl)amino)-3-oxopropyl)-7,8,9,11,12,13,14,15,16,17-decahydro-6H-cyclopenta[a]phenanthren-3-yl dihydrogen phosphate;

Compound 17 (13S,15R,E)-17-(methoxyimino)-13-methyl-15-(3-((5-methylthiazol-2-yl)amino)-3-oxopropyl)-4-nitro-7,8,9,11,12,13,14,15,16,17-decahydro-6H-cyclopenta[a]phenanthren-3-yl dihydrogen phosphate;

Compound 18 (13S,15R,E)-17-(hydroxyimino)-13-methyl-15-(3-((5-methylthiazol-2-yl)amino)-3-oxopropyl)-4-nitro-7,8,9,11,12,13,14,15,16,17-decahydro-6H-cyclopenta[a]phenanthren-3-yl dihydrogen phosphate;

Compound 19 (13S,15R,E)-4-bromo-17-(hydroxyimino)-13-methyl-15-(3((5-methylthiazol-2-yl)amino)-3-oxopropyl)-7,8,9,11,12,13,14,15,16,17-decahydro-6H-cyclopenta[a]phenanthren-3-yl dihydrogen phosphate;

Compound 20 (13S,15R,E)-2,4-diiodo-17-(methoxyimino)-13-methyl-15-(3-((5-methylthiazol-2-yl) amino)-3-oxopropyl)-7,8,9,11,12,13,14,15,16,17-decahydro-6H-cyclopenta[a]phenanthren-3-yl dimethylglycinate;

Compound 21 (13S,15R,E)-2,4-dibromo-17-(hydroxyimino)-13-methyl-15-(3-((5-methylthiazol-2-yl) amino)-3-oxopropyl)-7,8,9,11,12,13,14,15,16,17-decahydro-6H-cyclopenta[a]phenanthren-3-yl dihydrogen phosphate;

Compound 22 (13S,15R,E)-2,4-diiodo-17-(methoxyimino)-13-methyl-15-(3-((5-methylthiazol-2-yl) amino)-3-oxopropyl)-7,8,9,11,12,13,14,15,16,17-decahydro-6H-cyclopenta[a]phenanthren-3-yl dihydrogen phosphate;

and pharmaceutically acceptable salts thereof.

11. A pharmaceutical composition comprising an effective amount of one or more compounds as claimed in claim 1, together with one or more pharmaceutically acceptable excipient(s).

12. A pharmaceutical composition as claimed in claim 11 further comprising one or more other active ingredients.

* * * * *